(12) United States Patent
Doll et al.

(10) Patent No.: US 6,576,639 B1
(45) Date of Patent: Jun. 10, 2003

(54) COMPOUNDS FOR THE INHIBITION OF FARNESYL PROTEIN TRANSFERASE

(75) Inventors: Ronald J. Doll, Maplewood; Joseph M. Kelly, Parlin; Alan K. Mallams, Hackettstown; F. George Njoroge, Union; Stacy W. Remiszewski, Washington Township; Arthur G. Taveras, Rockaway, all of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/520,449

(22) Filed: Mar. 8, 2000

Related U.S. Application Data

(62) Division of application No. 09/094,721, filed on Jun. 15, 1998, now abandoned.
(60) Provisional application No. 60/049,860, filed on Jun. 17, 1997.
(51) Int. Cl.$^7$ .................. A61K 31/44; A61K 31/4353; C07D 401/14; C07D 401/06
(52) U.S. Cl. .................. 514/290; 546/93; 544/361
(58) Field of Search .................. 514/290; 546/93

(56) References Cited

U.S. PATENT DOCUMENTS 4,826,853 A    5/1989   Piwinski et al. ............ 514/290

(List continued on next page.)

FOREIGN PATENT DOCUMENTS

EP    0 270 818    5/1989 ......... C07D/401/04

(List continued on next page.)

OTHER PUBLICATIONS

Bishop et al., *The Jouranl of Biological Chemistry*, vol. 270, No. 15, pp. 30611–30618 (1995).

(List continued on next page.)

*Primary Examiner*—Alan L. Rotman
(74) *Attorney, Agent, or Firm*—Robert L. Bernstein; Henry C. Jeanette

(57) ABSTRACT

Novel compounds, such as:

are disclosed.
Also disclosed are methods for inhibiting the abnormal growth of cells, for inhibiting farnesyl protein transferase and for treating cancers using the novel compounds.

19 Claims, No Drawings

U.S. PATENT DOCUMENTS

| | | | |
|---|---|---|---|
| 5,089,496 A | 2/1992 | Piwinski et al. | 514/253 |
| 5,151,423 A | 9/1992 | Piwinski et al. | 514/254 |
| 5,393,890 A | 2/1995 | Syoji et al. | 546/80 |
| 5,661,152 A | 8/1997 | Bishop et al. | 514/254 |
| 5,672,611 A | 9/1997 | Doll et al. | 514/325 |
| 5,684,013 A | 11/1997 | Afonso et al. | 514/290 |
| 5,696,121 A | 12/1997 | Bishop et al. | 514/254 |
| 5,700,806 A | 12/1997 | Doll et al. | 514/290 |
| 5,703,090 A | 12/1997 | Afonso et al. | 514/290 |
| 5,712,280 A | 1/1998 | Doll et al. | 514/253 |
| 5,714,609 A | 2/1998 | Bishop et al. | 546/93 |
| 5,719,148 A | 2/1998 | Bishop et al. | 514/228.2 |
| 5,721,236 A | 2/1998 | Bishop et al. | 514/225 |
| 5,728,703 A | 3/1998 | Bishop et al. | 514/254 |
| 5,807,853 A | 9/1998 | Bishop | 514/228.2 |
| 5,925,757 A | 6/1999 | Mallams | 544/361 |
| 6,228,856 B1 * | 5/2001 | Njoroge et al. | 514/228.2 |
| 6,228,865 B1 * | 5/2001 | Doll | 514/290 |
| 6,239,140 B1 * | 5/2001 | Cooper et al. | 514/290 |
| 6,242,458 B1 * | 6/2001 | Bishop et al. | 514/290 |

FOREIGN PATENT DOCUMENTS

| | | | |
|---|---|---|---|
| EP | 0 396 083 | 11/1990 | C07D/401/14 |
| EP | 0 495 484 | 7/1992 | C07D/401/04 |
| WO | WO95/10515 | 4/1995 | C07D/401/04 |
| WO | WO95/10516 | 4/1995 | C07D/401/04 |
| WO | WO95/15949 | 6/1995 | C07D/211/70 |
| WO | WO96/30018 | 10/1996 | A61K/31/495 |
| WO | WO96/30362 | 10/1996 | C07D/401/04 |
| WO | WO96/30363 | 10/1996 | C07D/401/04 |
| WO | WO96/31477 | 10/1996 | C07D/221/16 |
| WO | WO96/31478 | 10/1996 | C07D/221/16 |
| WO | WO97/23478 | 7/1997 | C07D/401/04 |

OTHER PUBLICATIONS

Njoroge et al., *Bioorganic & Medicinal Chemistry Letters*, vol. 6, No. 24, pp. 2977–2982 (1996).

* cited by examiner

COMPOUNDS FOR THE INHIBITION OF FARNESYL PROTEIN TRANSFERASE

"REFERENCE TO RELATED APPLICATIONS

This is a divisional application of application Ser. No. 09/094,721 filed Jun. 15, 1998 (now abandoned) which in turn claims the benefit of U.S. Provisional Application No. 60/049,860 filed Jun. 17, 1997.

BACKGROUND

The biological significance of the Ras oncogene, and the role of both Ras and the enzyme known as farnesyl protein transferase in the conversion of normal cells to cancer cells, are described in PCT International Publication Nos. WO95/00497 and WO95/10516. Each of those publications also describes a distinct class of compounds which inhibit the activity of the enzyme farnesyl protein transferase, and thereby the farnesylation of the Ras protein.

PCT International Publication No. WO95/10516 relates to tricyclic amide and urea compounds of the general formula (1.0)

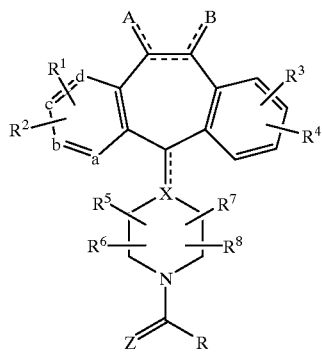

(1.0)

and their use in a method for inhibiting Ras function and the abnormal growth of cells. A number of sub-generic classes of compounds of formula (1.0) are described, which include compounds of the formulae (5.0c), (5.1c) and (5.2a)

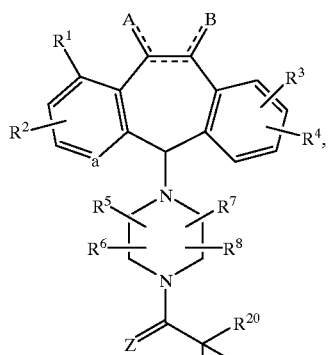

(5.0c)

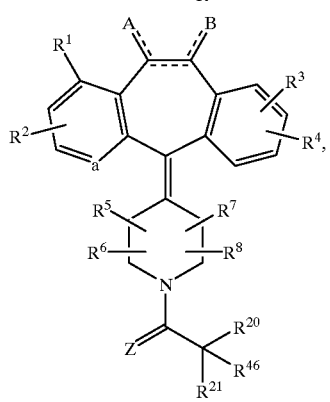

(5.1c)

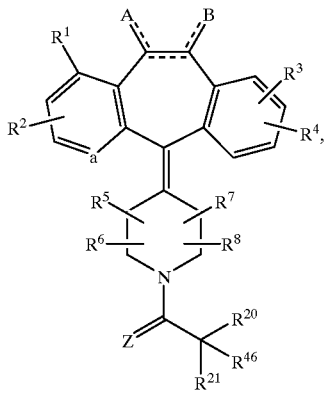

(5.2a)

as well as the 11-R-isomer and 11-S-isomers of compounds (5.0c) and (5.1c). A number of specific compounds within each such sub-genus are also described therein, as is the biological activity of those compounds.

SUMMARY OF THE INVENTION

The present invention provides novel tricyclic amide compounds selected from the group consisting of:

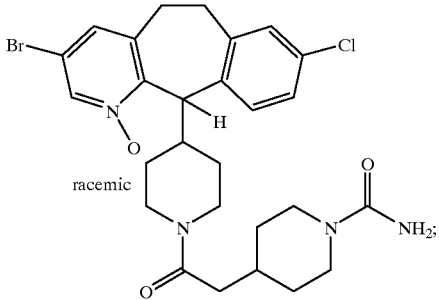

(1.0)

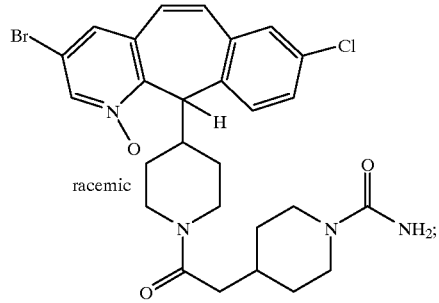

(2.0)

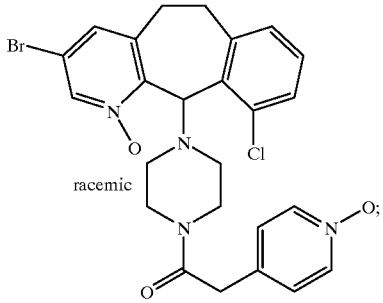

(3.0)

-continued
(4.0)
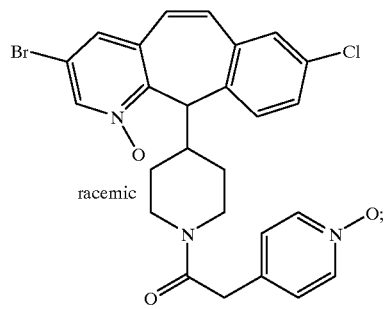
(5.0)
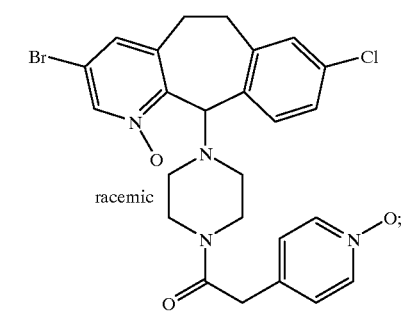
(6.0)
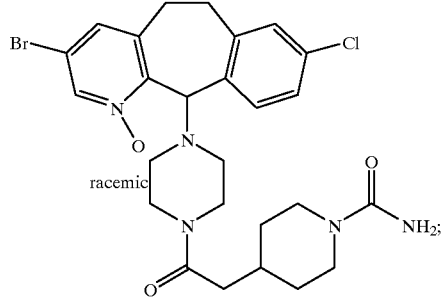
(7.0)
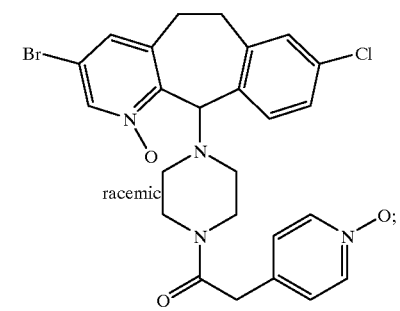
(8.0)
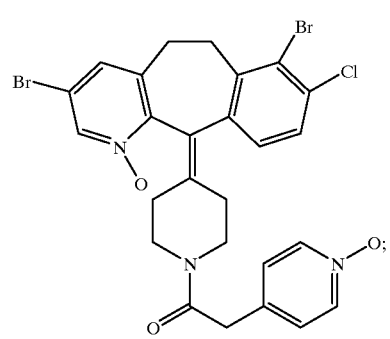
-continued
(9.0)
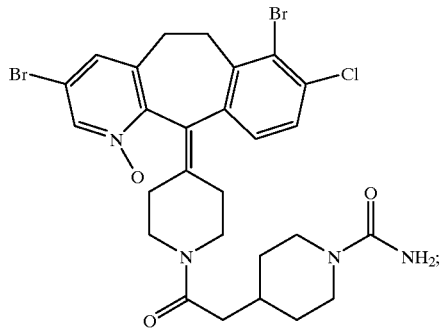
(10.0)
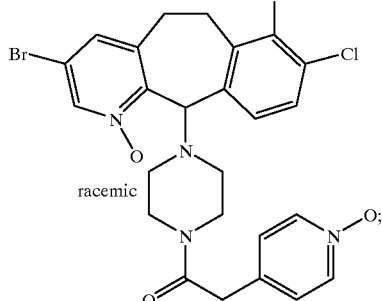
(11.0)
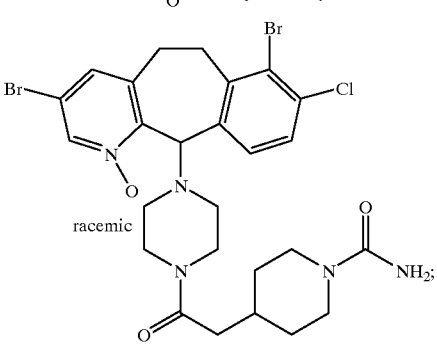
(12.0)
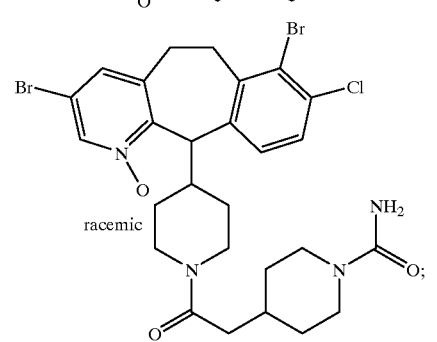
(13.0)
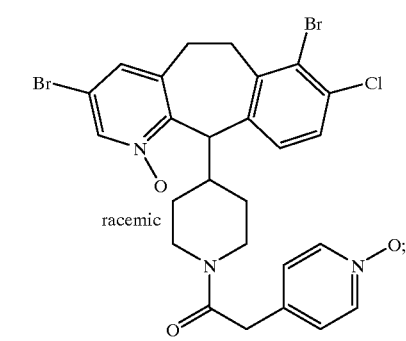

-continued (23.0A)
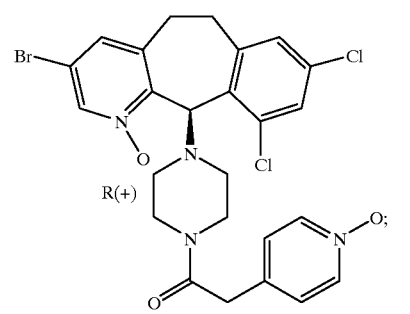
(24.0)
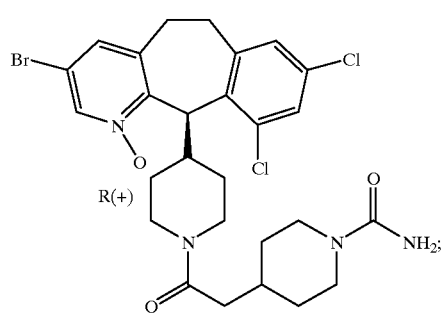
(25.0)
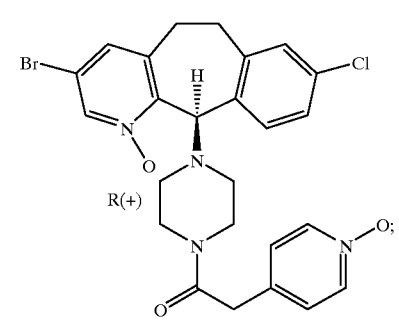
(26.0)
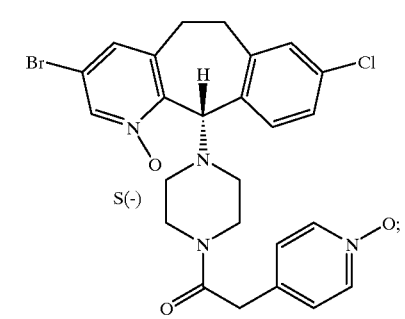
(27.0)
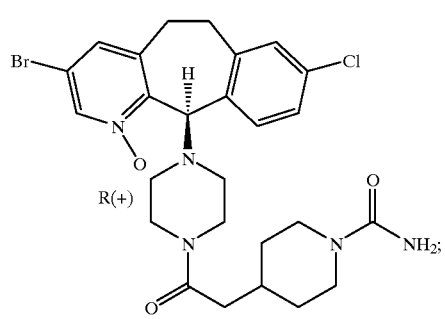
(28.0)
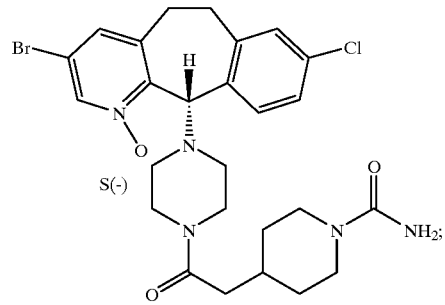
(29.0)
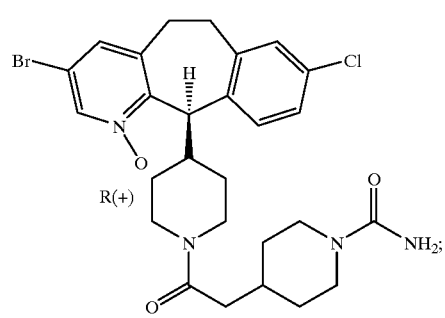
(30.0)
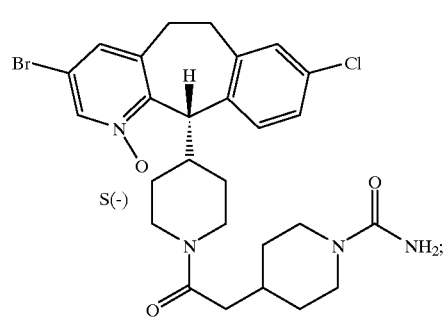
(31.0)
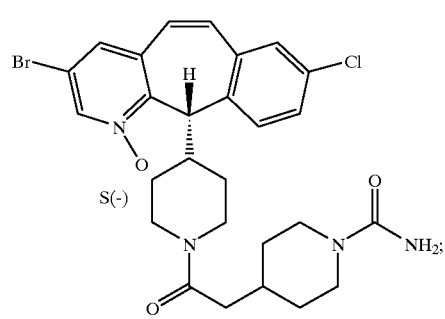
(32.0)
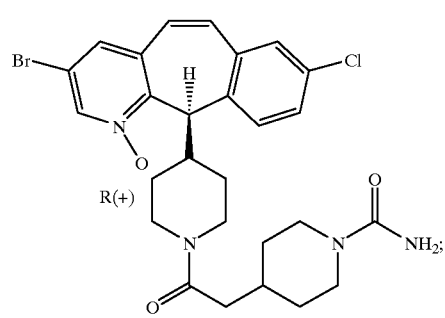

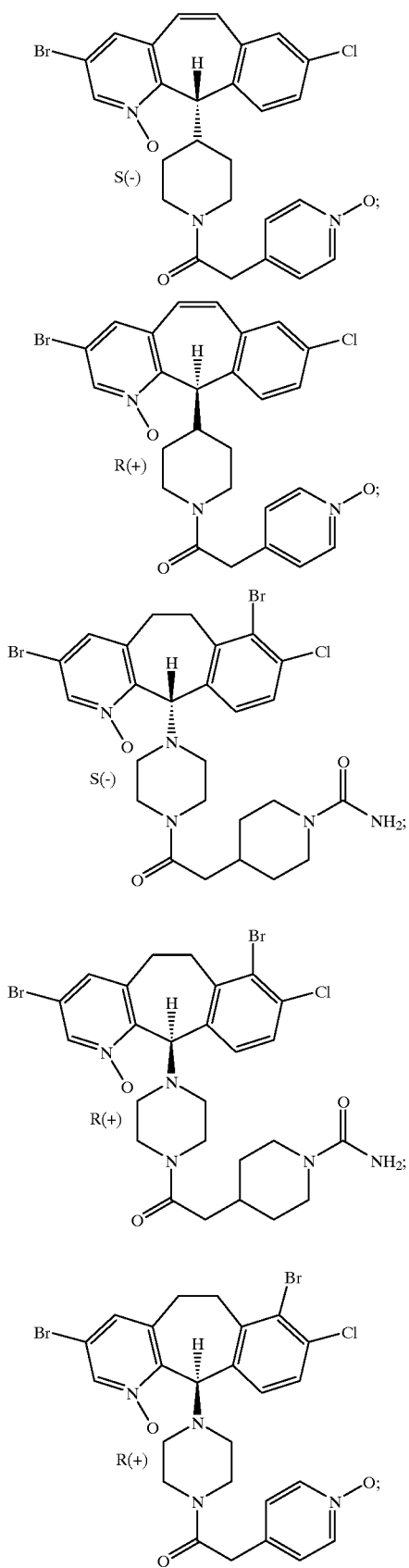
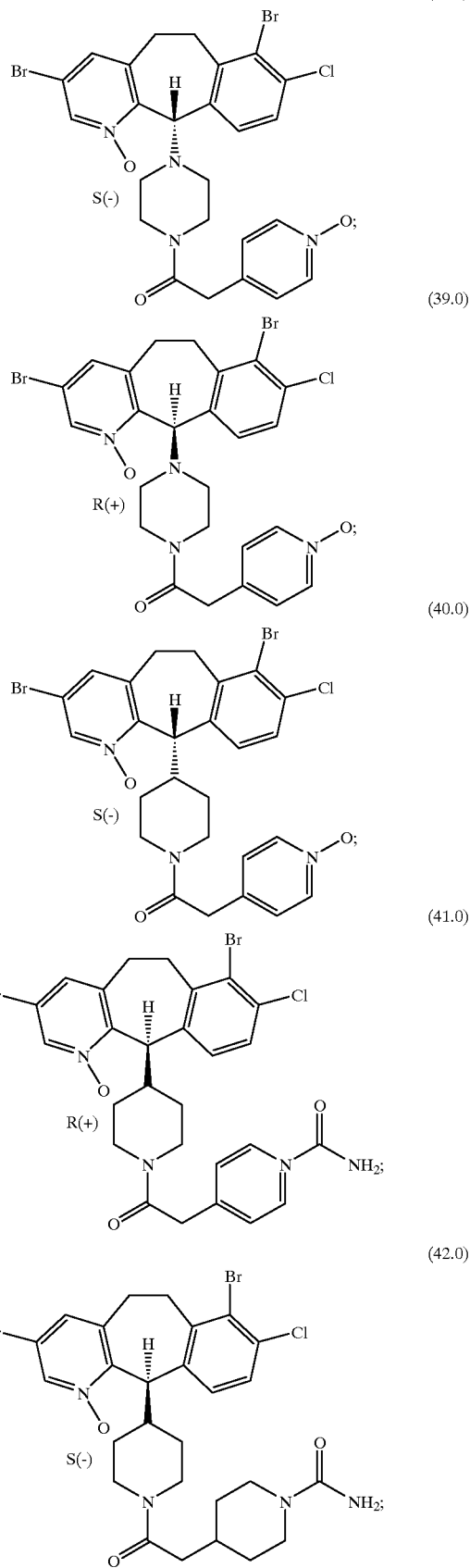

(43.0)
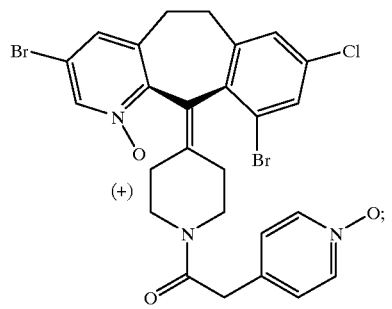
(44.0)
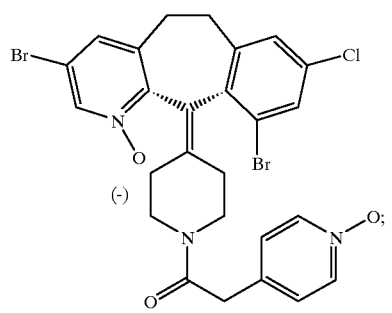
(45.0)
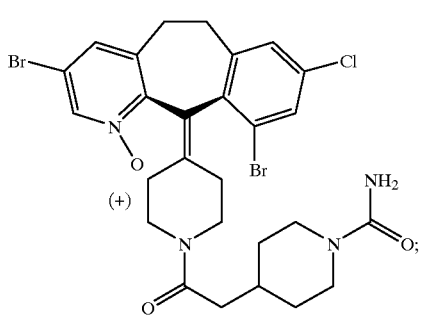
(46.0)
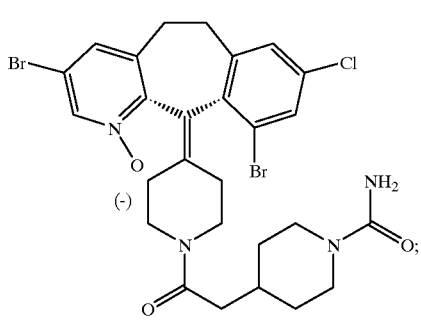
(47.0)
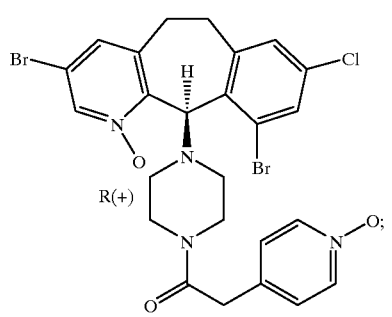
(48.0)
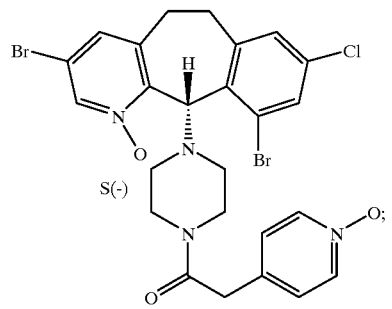
(49.0)
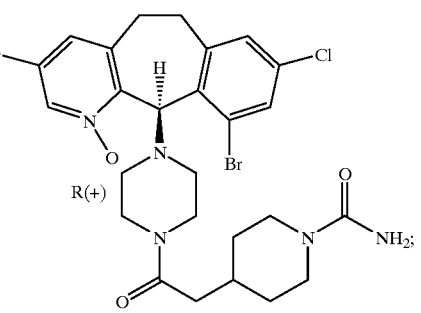
(50.0)
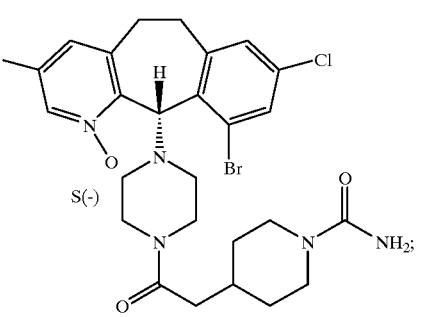
(51.0)
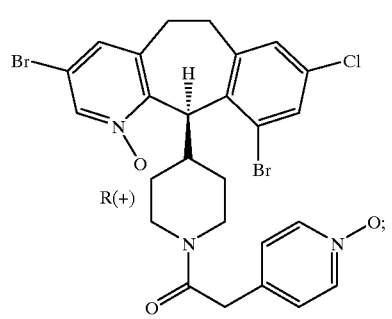
(52.0)
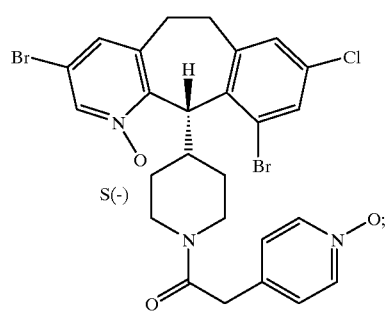

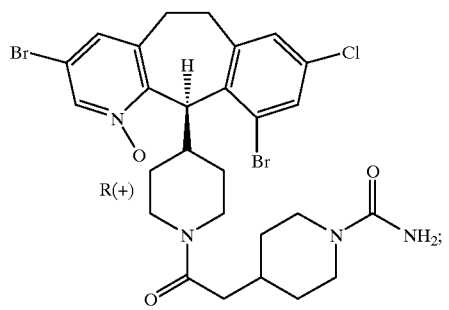 (53.0)
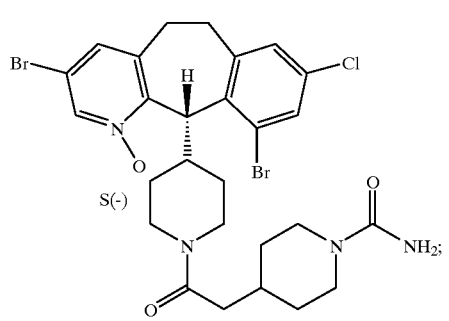 (54.0)
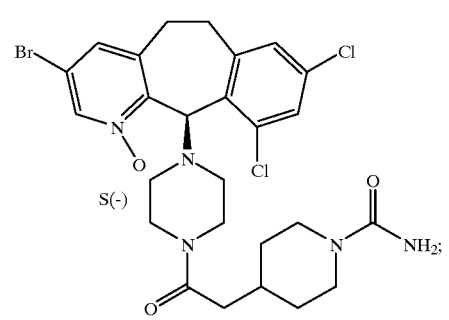 (55.0)
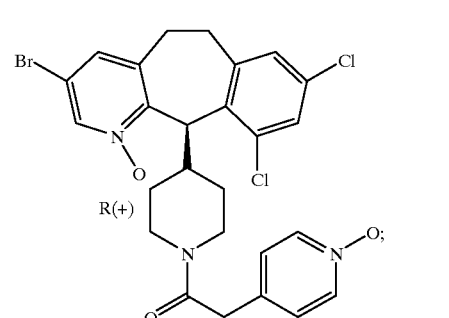 (56.0)
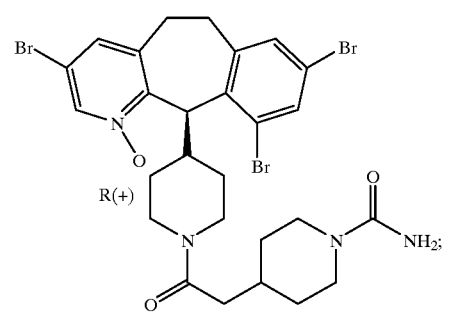 (57.0)
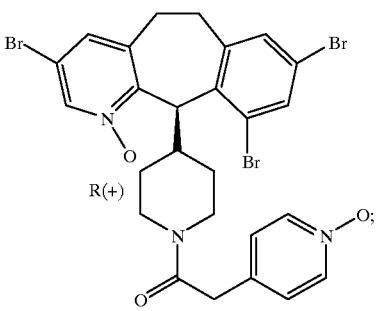 (58.0)
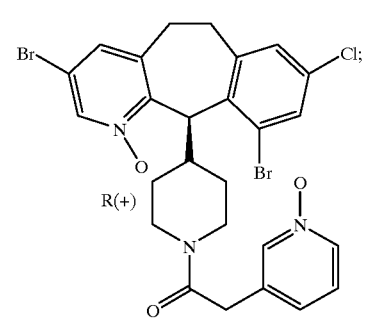 (59.0)
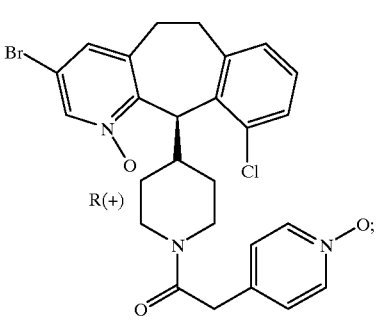 (60.0)
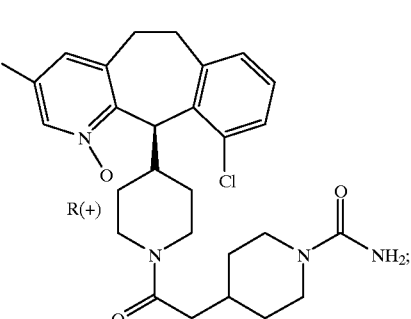 (61.0)
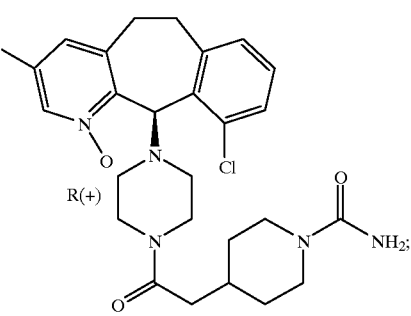 (62.0)

-continued (63.0)
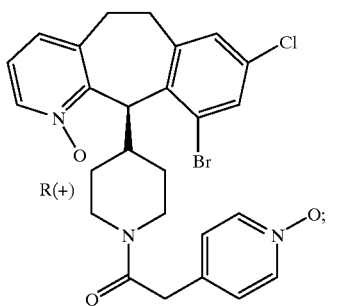

(64.0)
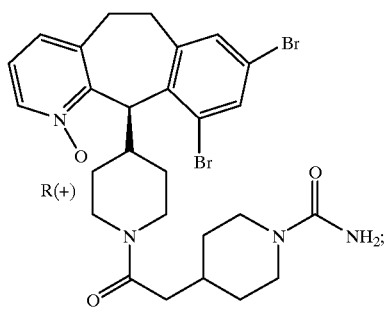

(65.0)
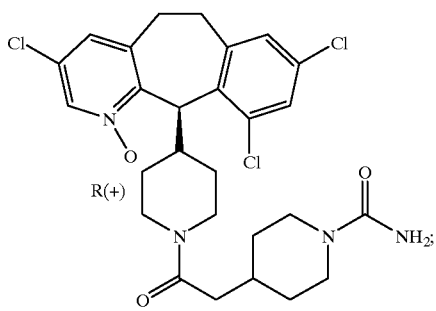

or pharmaceutically acceptable salts or solvates thereof.

Optical rotation of the compounds ((+)-or n(−)-) are measured in methanol or ethanol at 25° C.

This invention includes the above compounds in the amorphous state or in the cyrstalline state.

Thus, compounds of this invention include compounds selected from the group consisting of: Compounds 1.0, 2.0, 3.0, 4.0, 5.0, 7.0 and 6.0, or pharmaceutically acceptable salts thereof, wherein said compounds are as defined above.

Compounds of this invention also include compounds selected from the group consisting of: Compounds 10.0, 11.0, 12.0, 13.0, 16.0, 17.0, 18.0, 19.0, 20.0, 21.0, and 22.0, or pharmaceutically acceptable salts thereof, and wherein said compounds are as defined above.

Compounds of this invention also include compounds selected from the group consisting of: Compounds 8.0, 9.0, 14.0, and 15.0, or pharmaceutically acceptable salts thereof, and wherein said compounds are as defined above.

Compounds of this invention also include compounds selected from the group consisting of: Compounds 23.0, 25.0, 26.0, 27.0, 28.0, 29.0, 30.0, 31.0, 32.0, 33.0, 34.0, 60.0, 61.0, 62.0, 63.0, and 64.0, or pharmaceutically acceptable salts thereof, and wherein said compounds are as defined above.

Compounds of this invention also include compounds selected from the group consisting of: Compounds 23.0A, 24.0, 35.0, 36.0, 37.0, 38.0, 39.0, 40.0, 41.0, 42.0, 47.0, 48.0, 49.0, 50.0, 51.0, 52.0, 53.0, 54.0, 55.0, 56.0, 57.0, 58.0, 59.0, and 65.0, or pharmaceutically acceptable salts thereof, and wherein said compounds are as defined above.

Compounds of this invention also include compounds selected from the group consisting of: Compounds 43.0, 44.0, 45.0 and 46.0, or pharmaceutically acceptable salts thereof, and wherein said compounds are as defined above.

The preferred compounds include Compounds 5.0, 7.0, 25.0, 27.0, 29.0, and 34.0.

The preferred compounds also include Compounds 51.0 and 53.0

The preferred compounds also include Compounds 40.0 and 42.0.

More preferred compounds are Compounds 25.0, 27.0, 51.0 and 53.0.

Those skilled in the art will appreciate that the tricyclic ring system is numbered:

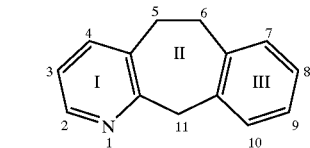

Those skilled in the art will also appreciate that the S and R stereochemistry at the C-11 bond are:

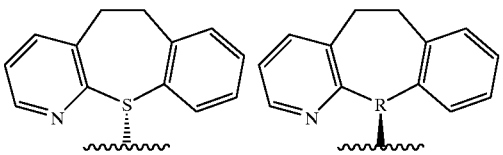

Inhibition of farnesyl protein transferase by the tricyclic compounds of this invention has not been reported previously. Thus, this invention provides a method for inhibiting farnesyl protein transferase using tricyclic compounds of this invention which: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras.

This invention provides a method for inhibiting or treating the abnormal growth of cells, including transformed cells, by administering an effective amount of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

This invention also provides a method for inhibiting or treating tumor growth (cancer) by administering an effective amount of the tricyclic compounds, described herein, to a mammal (e.g., a human) in need of such treatment. In particular, this invention provides a method for inhibiting or treating the growth of tumors expressing an activated Ras oncogene by the administration of an effective amount of the above described compounds. Examples of tumors which may be inhibited or treated include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma, epidermal carcinoma, breast cancers and prostate cancers.

It is believed that this invention also provides a method for inhibiting proliferative diseases, both benign and malignant, wherein Ras proteins are aberrantly activated as a result of oncogenic mutation in other genes—i.e., the Ras gene itself is not activated by mutation to an oncogenic form—with said inhibition being accomplished by the administration of an effective amount of the tricyclic compounds described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited by the tricyclic compounds described herein.

The compounds of this invention inhibit farnesyl protein transferase and the farnesylation of the oncogene protein Ras. This invention further provides a method of inhibiting ras farnesyl protein transferase, in mammals, especially humans, by the administration of an effective amount of the tricyclic compounds described above. The administration of the compounds of this invention to patients, to inhibit farnesyl protein transferase, is useful in the treatment of the cancers described above.

The tricyclic compounds useful in the methods of this invention inhibit the abnormal growth of cells. Without wishing to be bound by theory, it is believed that these compounds may function through the inhibition of G-protein function, such as ras p21, by blocking G-protein isoprenylation, thus making them useful in the treatment of proliferative diseases such as tumor growth and cancer. Without wishing to be bound by theory, it is believed that these compounds inhibit ras farnesyl protein transferase, and thus show antiproliferative activity against ras transformed cells.

DETAILED DESCRIPTION OF THE INVENTION

As used herein, the following terms are used as defined below unless otherwise indicated:

$M^+$-represents the molecular ion of the molecule in the mass spectrum;

$MH^+$-represents the molecular ion plus hydrogen of the molecule in the mass spectrum;

Pyridyl N-oxides are herein represented by the group

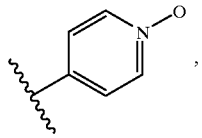

The following solvents and reagents are referred to herein by the abbreviations indicated: tetrahydrofuran (THF); ethanol (EtOH); methanol (MeOH); acetic acid (HOAc or AcOH); ethyl acetate (EtOAc); N,N-dimethylformamide (DMF); trifluoroacetic acid (TFA); trifluoroacetic anhydride (TFAA); 1-hydroxy-benzotriazole (HOBT); m-chloroperbenzoic acid (MCPBA); triethylamine (Et$_3$N); diethyl ether (Et$_2$O); ethyl chloroformate ClCO$_2$Et); 1-(3-dimethylaminopropyl)-3-ethyl carbodiimde hydrochloride (DEC); diisobutylaluminum hydride (DIBAL); isopropanol (iPrOH); dimethylsulfoxide (DMSO)

Certain compounds of the present invention may exist in different isomeric forms (e.g., enantiomers or diastereoisomers) including atropisomers (i.e., compounds wherein the 7-membered ring is in a fixed conformation such that the 11-carbon atom is positioned above or below the plane of the fused beznene rings due to the presence of a 10-bromo substituent). The invention contemplates all such isomers both in pure form and in admixture, including racemic mixtures. Enol forms are also included.

Certain basic tricyclic compounds also form pharmaceutically acceptable salts, e.g., acid addition salts. For example, the pyrido-nitrogen atoms may form salts with strong acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such salts are intended to be pharmaceutically acceptable salts within the scope of the invention and all are considered equivalent to the free forms of the corresponding compounds for purposes of the invention.

The compounds of the present invention can be prepared by the procedures described below.

Preparation of Piperidine Compounds

The compounds of the invention having a piperidine ring (Ring IV):

(I)

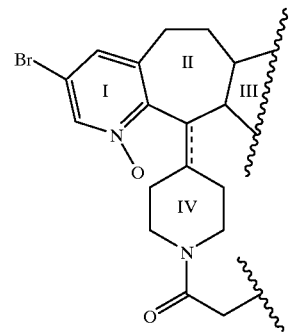

can be prepared, by techniques well known in the art, from the corresponding unoxidized pyridyl compounds:

(II)

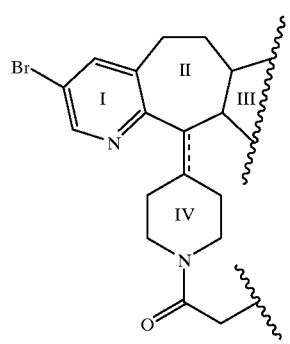

Thus, the compounds of the invention can be prepared from:
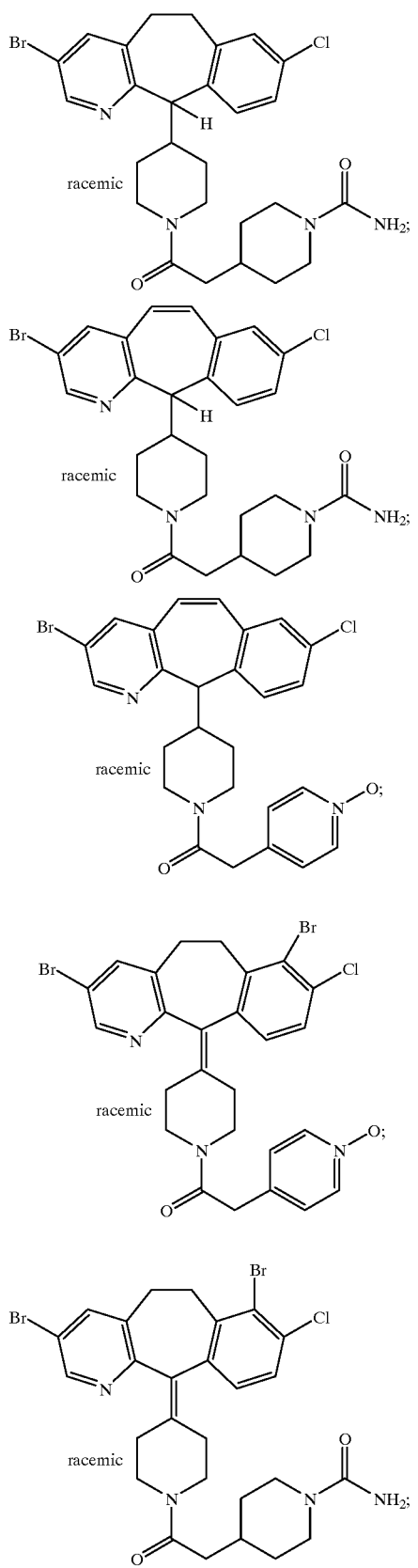
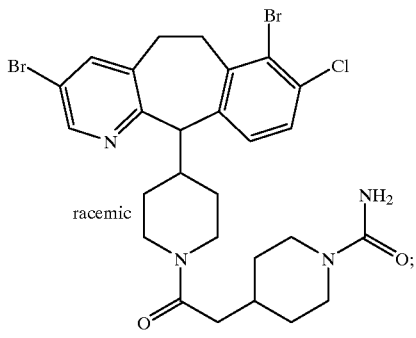
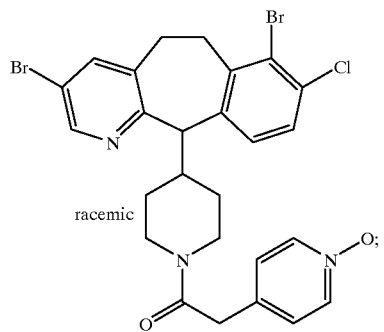
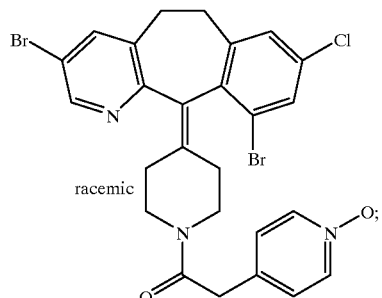
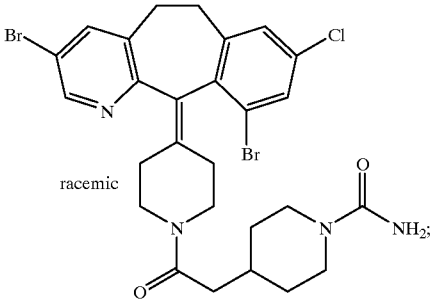
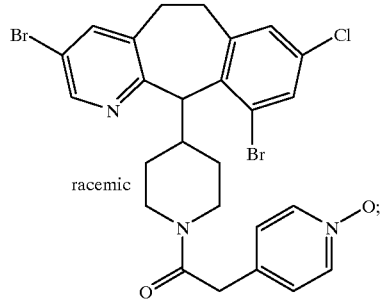

-continued
(21.1)
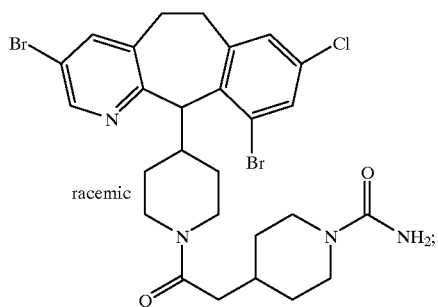
racemic
(22.1)
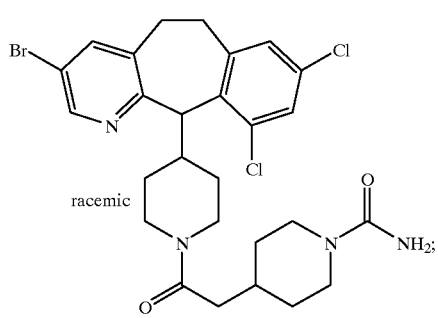
racemic
(24.1)
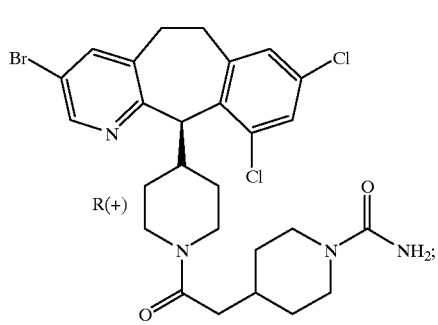
R(+)
(29.1)
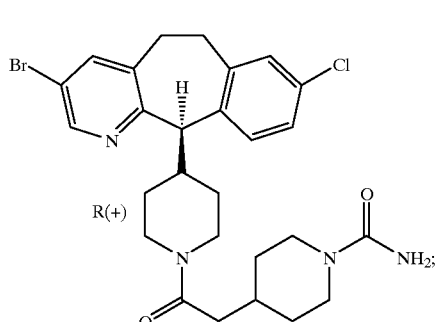
R(+)
(30.1)
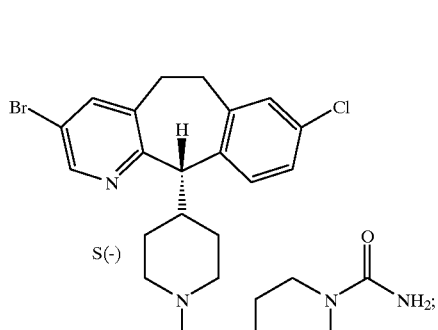
S(-)
(31.1)
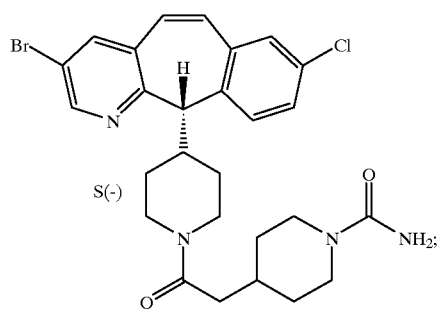
S(-)
(32.1)
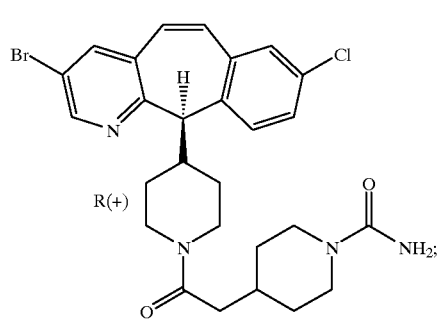
R(+)
(33.1)
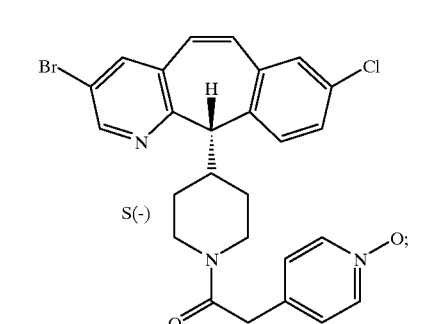
S(-)
(34.1)
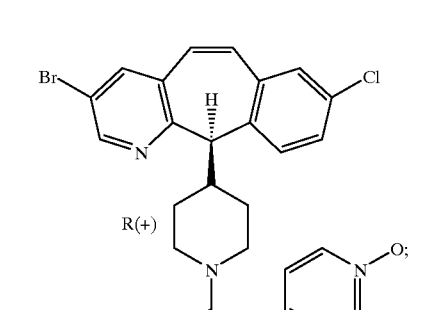
R(+)
(39.1)
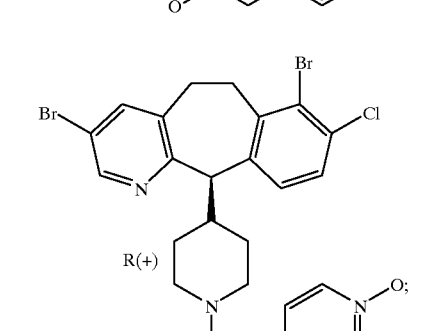
R(+)

(40.1)
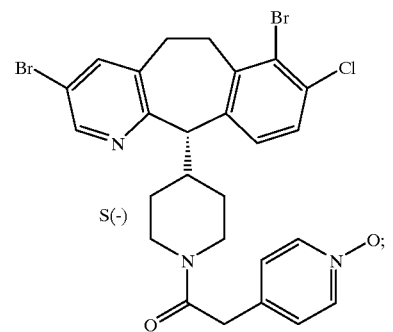
S(-)
(41.1)
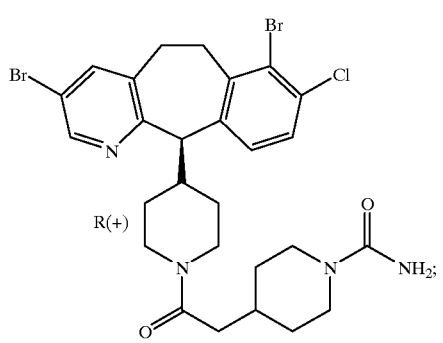
R(+)
(42.1)
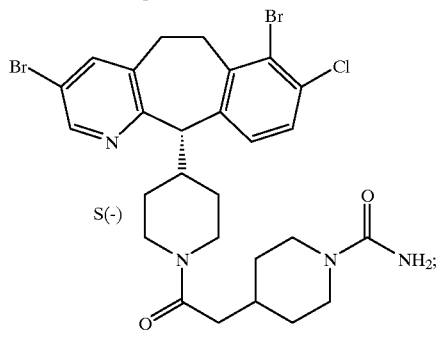
S(-)
(43.1)
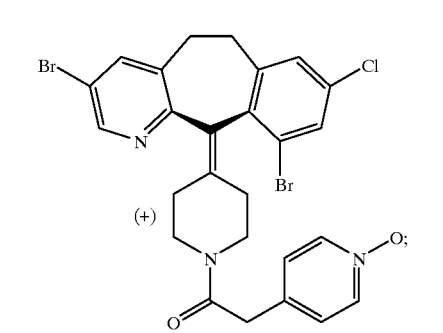
(+)
(44.1)
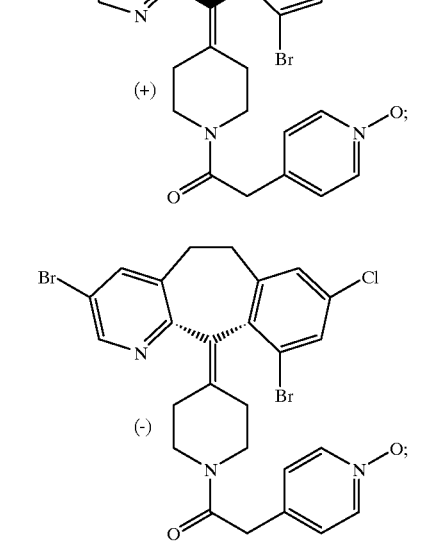
(-)
(45.1)
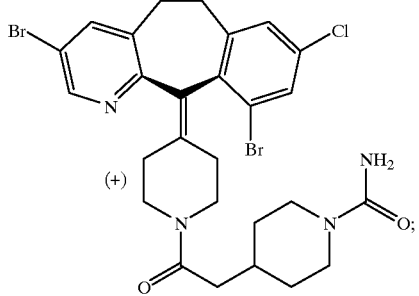
(+)
(46.1)
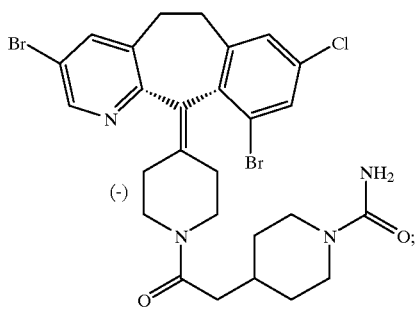
(-)
(51.1)
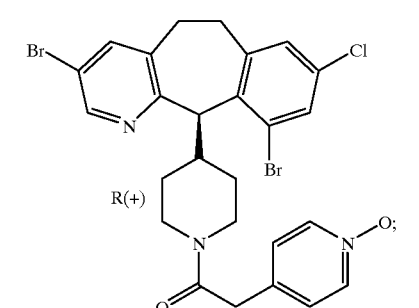
R(+)
(52.1)
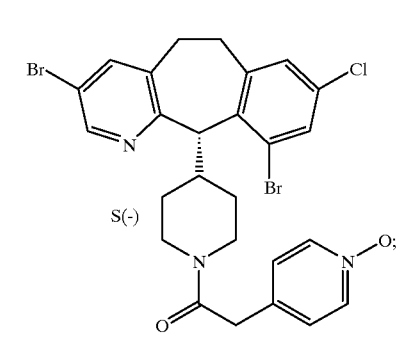
S(-)
(53.1)
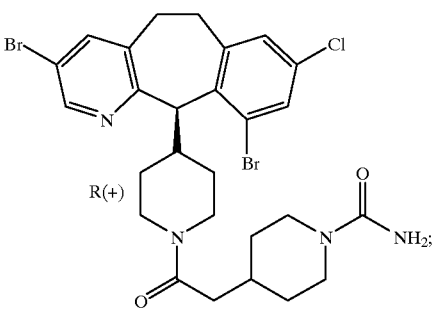
R(+)

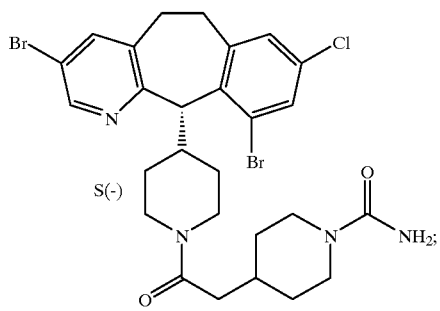
(54.1)
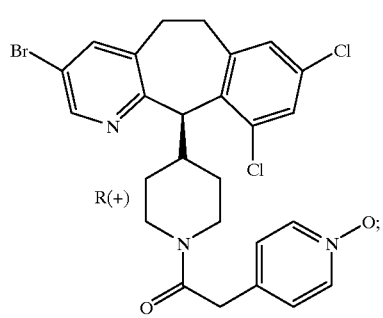
(56.1)
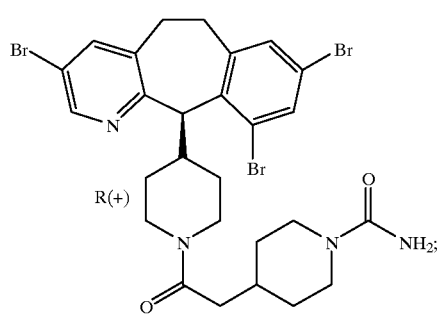
(57.1)
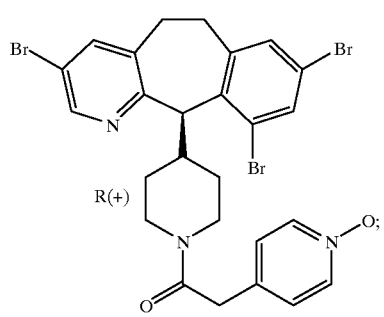
(58.1)
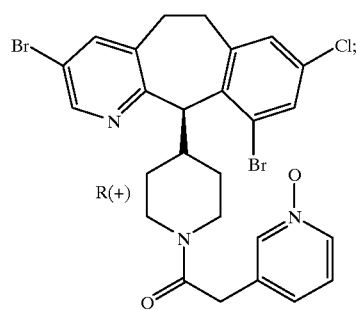
(59.1)
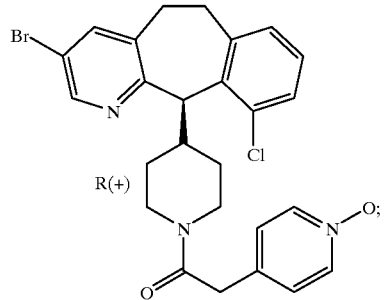
(60.1)
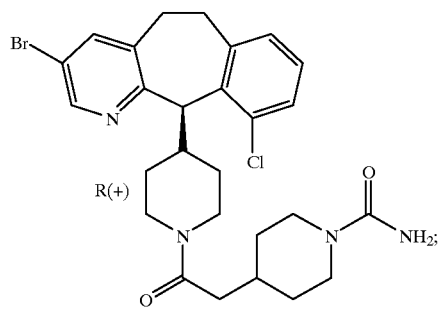
(61.1)
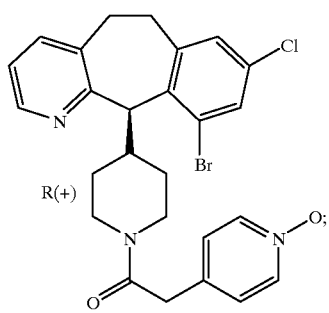
(63.1)
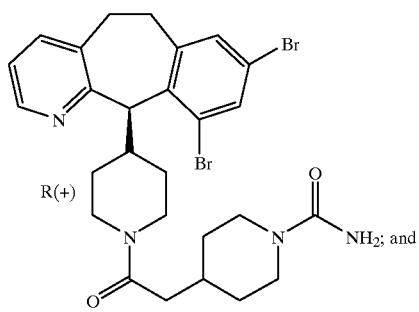
(64.1)
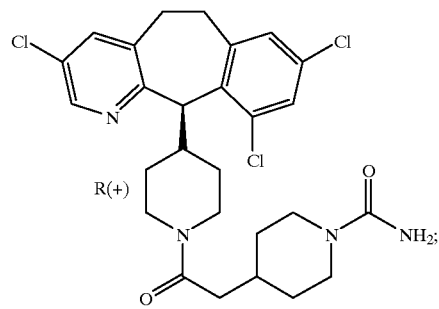
(65.1)

The piperidine compounds (Formula I) of the invention can be prepared from the above pyridyl compounds by oxidation with meta-chloroperoxybenzoic acid. This reaction is conducted in a suitable organic solvent, e.g., dichloromethane (usually anhydrous) or methylene chloride, at a suitable temperature, to produce the compounds of the invention having the N—O substituent at position 1 of Ring I of the tricyclic ring system.

Generally, the organic solvent solution of the starting tricyclic reactant is cooled to about 0° C. before the m-chloro-peroxybenzoic acid is added. The reaction is then allowed to warm to room temperature during the reaction period. The desired product can be recovered by standard separation means. For example, the reaction mixture can be washed with an aqueous solution of a suitable base, e.g., saturated sodium bicarbonate or NaOH (e.g., 1N NaOH), and then dried over anhydrous magnesium sulfate. The solution containing the product can be concentrated in vacuo. The product can be purified by standard means, e.g., by chromatography using silica gel (e.g., flash column chromatography).

Alternatively, the piperidine compounds (Formula I) of the invention can be made from intermediate compounds of Formulas 1.1 to 65.1 using the oxidation procedure with m-chloroperoxybenzoic acid. The oxidized intermediate compounds are then reacted to produce the compounds of the invention by methods known in the art. For example, the 3,8-dihalo compounds can be produced from the intermediate:

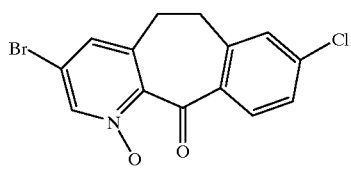

which is made by oxidizing the pyridyl compound

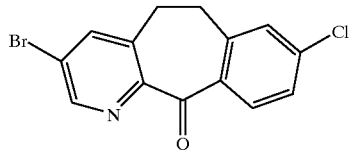

with m-chloroperoxybenzoic acid.

The 3,7,8-trihalo compounds, 3,8,10-trihalo compounds, 3,8-dihalo compounds and the 3,10-dihalo compounds can be produced from the intermediates

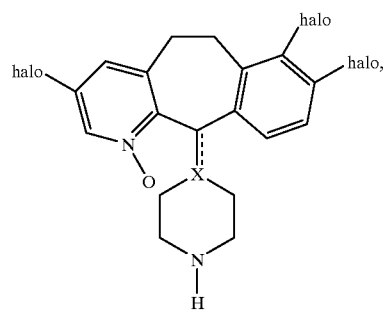 (III)

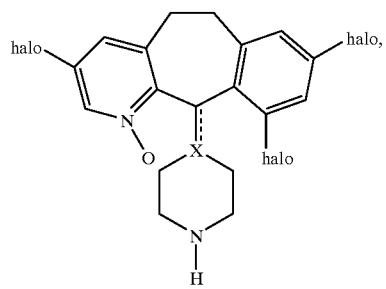 (IV)

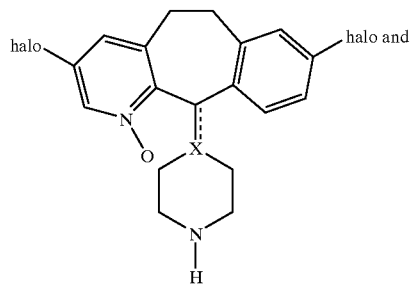 (V)

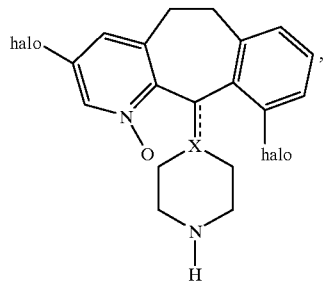 (VI)

respectively.

Compounds III to VI can be prepared using the above oxidation procedure with m-chloro-peroxybenzoic acid and the pyridyl compounds

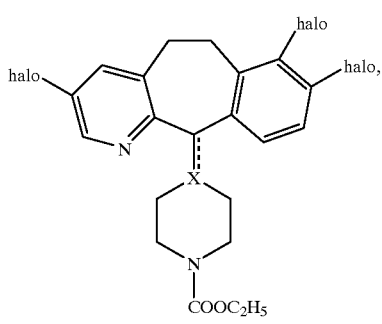 (VII)

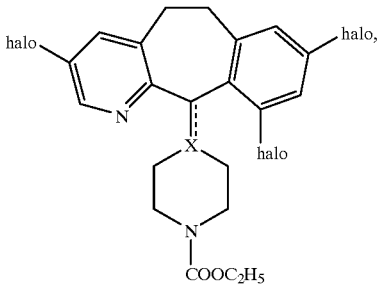 (VIII)

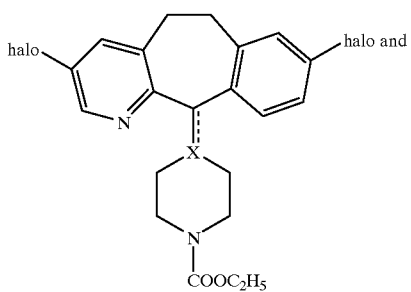

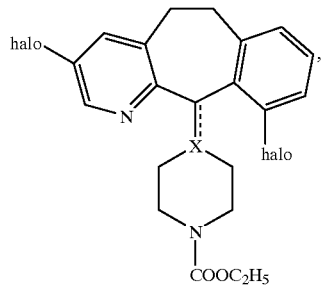

respectively, to produce the compounds

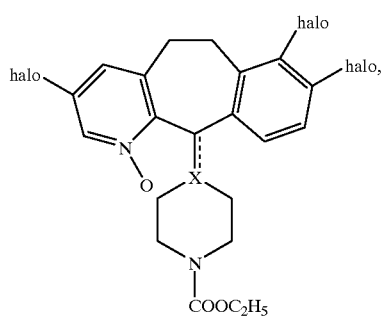

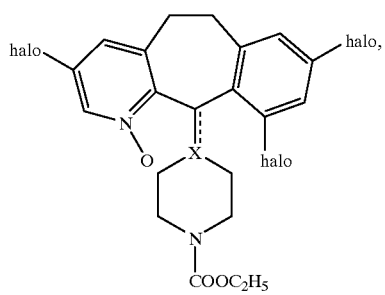

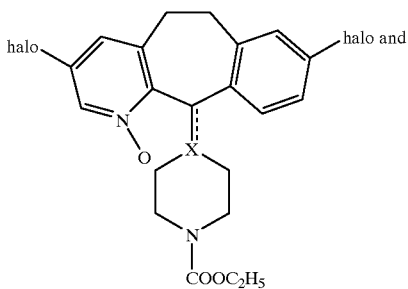

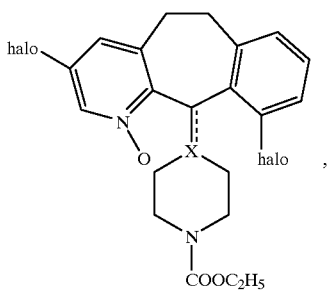

respectively. Compounds XI to XIV can then be converted to Compounds III to VI, respectively, by methods well known in the art.

In the above compounds the dotted line ( - - - ) represents an optional bond, and X represents CH when the optional bond is absent, and when the optional bond is present X represents C. The N—O intermediates are then reacted further to produce the compounds of the invention.

Those skilled in the art will appreciate that the oxidation reaction can be conducted on racemic mixtures and the isomers can then be separated by know techniques, or the isomers can be separated first and then oxidized to the corresponding N-oxide.

Those skilled in the art will appreciate that it is preferable to avoid an excess of m-chloroperoxybenzoic acid when the oxidation reaction is carried out on the compounds having a C-11 double bond to piperidine Ring IV (e.g., compounds 5.1, 6.1, 9.1, and the like). In these reactions an excess of m-chloro-peroxybenzoic acid can cause epoxidation of the C-11 double bond.

Intermediate compounds VII, VIII, IX and X are prepared by methods known in the art, for example by methods disclosed in WO 95/10516, in U.S. Pat. No. 5,151,423 and those described below. For example, Compounds VII to X can be prepared by reacting compounds

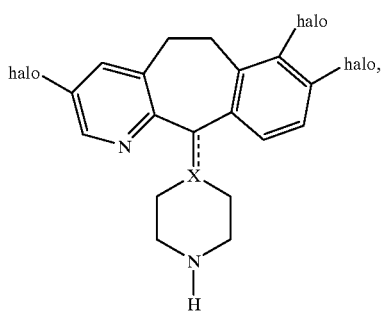

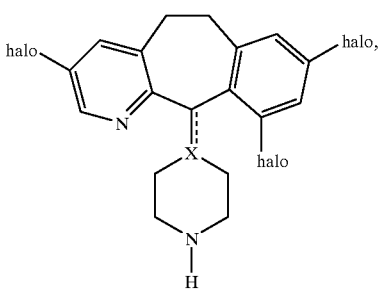

-continued (XVII)

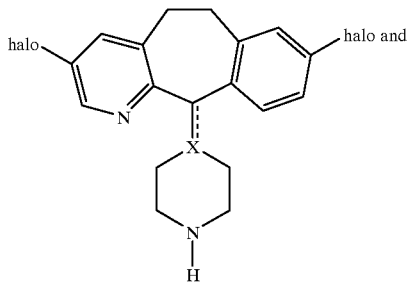

(XVIII)

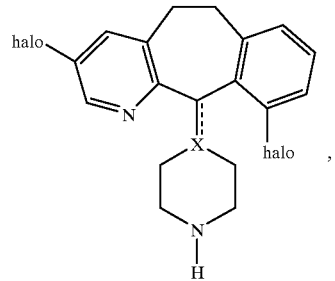

respectively, with $C_2H_5OCOCl$ and $Et_3N$ in an inert solvent (e.g., $CH_2Cl_2$).

Intermediate Compounds XV, XVI, XVII and XVIII wherein the C-3 postion of the pyridine ring in the tricyclic structure is substituted by bromo can also be prepared by a procedure comprising the following steps:

(a) reacting an amide of the formula

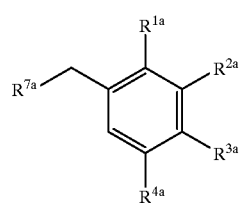

wherein $R^{11a}$ is Br, $R^{5a}$ is hydrogen and $R^{6a}$ is $C_1$–$C_6$ alkyl, aryl or heteroaryl; $R^{5a}$ is $C_1$–$C_6$ alkyl, aryl or heteroaryl and $R^{6a}$ is hydrogen; $R^{5a}$ and $R^{6a}$ are independently selected from the group consisting of $C_{1-6}$ alkyl and aryl; or $R^{5a}$ and $R^{6a}$, together with the nitrogen to which they are attached, form a ring comprising 4 to 6 carbon atoms or comprising 3 to 5 carbon atoms and one hetero moiety selected from the group consisting of —O— and —$NR^{9a}$—, wherein $R^{9a}$ is H, $C_1$–$C_6$ alkyl or phenyl;

with a compound of the formula

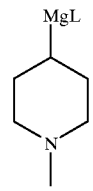

wherein $R^{1a}$, $R^{2a}$, $R^{3a}$ and $R^{4a}$ are are independently selected from the group consisting of hydrogen and halo and $R^{7a}$ is Cl or Br, in the presence of a strong base to obtain a compound of the formula

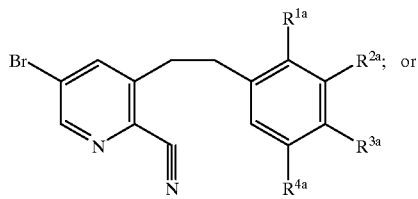

(b) reacting a compound of step (a) with (i) $POCl_3$ to obtain a cyano compound of the formula

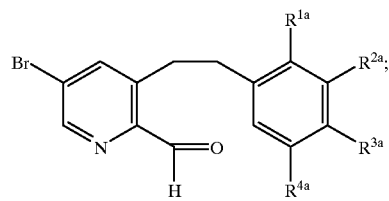

(ii) DIBALH to obtain an aldehyde of the formula

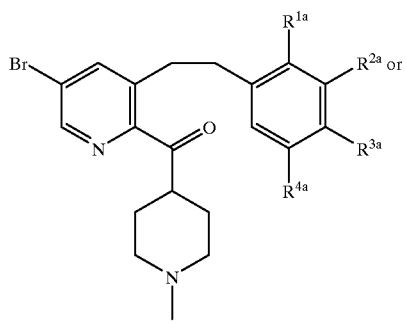

(c) reacting the cyano compound or the aldehyde with a piperidine derivative of the formula wherein L is a leaving group selected from the group consisting of Cl and Br, to obtain a ketone or an alcohol of the formula below, respectively:

-continued

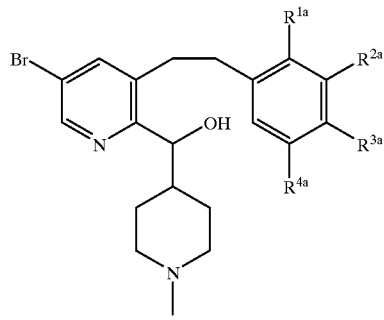

(d)(i) cyclizing the ketone with $CF_3SO_3H$ to obtain a compound of the formula:

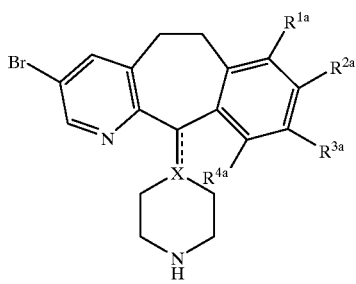

wherein the dotted line represents a double bond; or (d)(ii) cyclizing the alcohol with polyphosphoric acid to obtain an Intermediate compound wherein the dotted line represents a single bond.

Methods for preparing the Intermediate compounds disclosed in WO 95/10516, U.S. Pat. No. 5,151,423 and described below employ a tricyclic ketone intermediate. Such intermediates of the formula

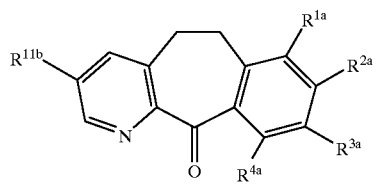

wherein $R^{11b}$, $R^{1a}$, $R^{2a}$, $R^{3a}$ and $R^{4a}$ are independently selected from the group consisting of hydrogen and halo, can be prepared by the following process comprising:

(a) reacting a compound of the formula

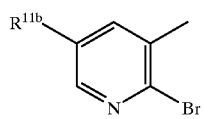

(i) with an amine of the formula $NHR^{5a}R^{6a}$, wherein $R^{5a}$ and $R^{6a}$ are as defined in the process above; in the presence of a palladium catalyst and carbon monoxide to obtain an amide of the formula:

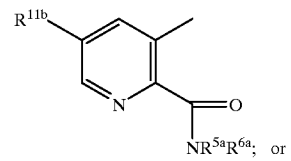

(ii) with an alcohol of the formula $R^{10a}OH$, wherein $R^{10a}$ is $C_1$–$C_6$ lower alkyl or $C_3$–$C_6$ cycloalkyl, in the presence of a palladium catalyst and carbon monoxide to obtain the ester of the formula

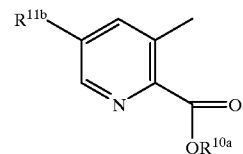

followed by reacting the ester with an amine of formula $NHR^{5a}R^{6a}$ to obtain the amide;

(b) reacting the amide with an iodo-substituted benzyl compound of the formula

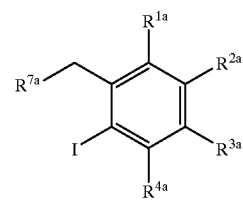

wherein $R^{1a}$, $R^{2a}$, $R^{3a}$, $R^{4a}$ and $R^{7a}$ are as defined above, in the presence of a strong base to obtain a compound of the formula

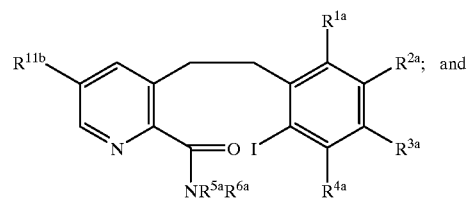

(c) cyclizing a compound of step (b) with a reagent of the formula $R^{8a}MgL$, wherein $R^{8a}$ is $C_1$–$C_8$ alkyl, aryl or heteroaryl and L is Br or Cl, provided that prior to cyclization, compounds wherein $R^{5a}$ or $R^{6a}$ is hydrogen are reacted with a suitable N-protecting group.

(+)-Isomers of compounds of Formula XVI (XVI)

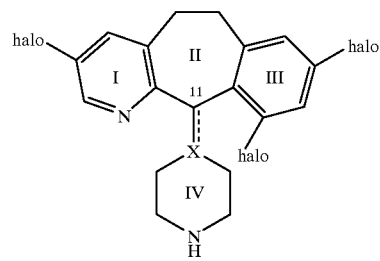

wherein X is CH can be prepared with high enantioselectivity by using a process comprising enzyme catalyzed transesterification. Preferably, a racemic compound of Formula XVI, wherein X is C and the double bond is present, is reacted with an enzyme such as Toyobo LIP-300 and an acylating agent such as trifluoroethly isobutyrate; the resultant (+)-amide is then hydrolyzed, for example by refluxing with an acid such as H$_2$SO$_4$, to obtain the corresponding optically enriched (+)-isomer wherein X is CH. Alternatively, a racemic compound of Formula XVI, wherein X is C and the double bond is present, is first reduced to the corresponding racemic compound of Formula XVI wherein X is CH and then treated with the enzyme (Toyobo LIP-300) and acylating agent as described above to obtain the (+)-amide, which is hydrolyzed to obtain the optically enriched (+)-isomer.

The compound of Preparative Example 21 is obtained in the crystalline state. Those skilled in the art will appreciate that compounds obtained in the amorphous state can be obtained in the crystalline state by crystallizing the amorphous materials from solvents or solvent mixtures such as acetone, diethyl ether, ethyl acetate, ethanol, 2-propanol, tert-butyl ether, water and the like according to procedures well known in the art.

Those skilled in the art will also appreciate that the racemic mixture of Compound 11.0 can be made according to the procedures described below. For Example, the intermediate of Preparative Example 6 can be used to prepare Compound 11.0.

Preparation of Piperazine Compounds

Compounds of the invention having a piperazine ring

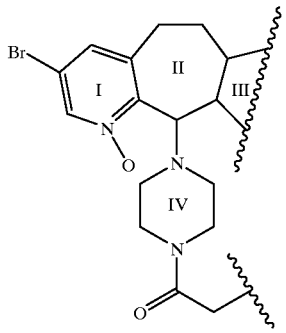

(XIX)

can be prepared from the tricyclic ketone:

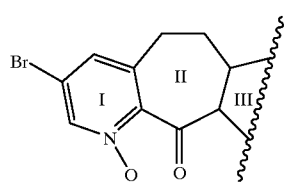

(XX)

Ketone XX can be prepared by oxidation of the corresponding pyridyl compound:

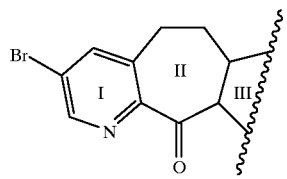

(XXI)

with m-chloroperoxybenzoic acid.

Ketone XX can be converted to the corresponding C-11 hydroxy compound which in turn can be converted to the corresponding C-11 chloro compound

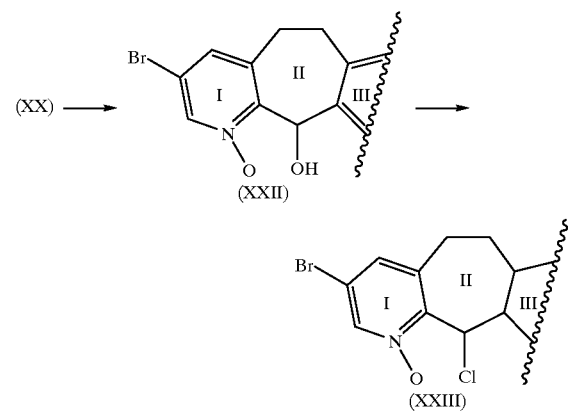

Compound XXIII can then be reacted with piperazine to produce the intermediate:

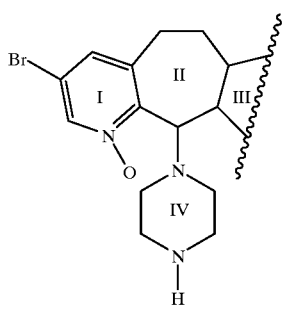

(XXIV)

Intermediate XXIV can then be reacted with the reagents which will provide the desired final product.

The above reactions are well known in the art and are illustrated in the examples below.

The examples that follow are intended to exemplify the claimed invention, and such examples should not be construed as limiting the disclosure or the claimed invention.

Preparative Example 1

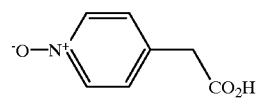

Step A

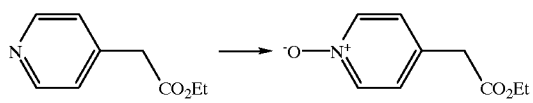

Combine 10 g (60.5 mmol) of ethyl 4-pyridylacetate and 120 mL of dry $CH_2Cl_2$ at $-20°$ C., add 10.45 g (60.5 mmol) of MCPBA and stir at $-20°$ C. for 1 hour and then at $25°$ C. for 67 hours. Add an additional 3.48 g (20.2 mmoles) of MCPBA and stir at $25°$ C. for 24 hours. Dilute with $CH_2Cl_2$ and wash with saturated $NaHCO_3$ (aqueous) and then water. Dry over $MgSO_4$, concentrate in vacuo to a residue, and chromatograph (silica gel, 2%–5.5% (10% $NH_4OH$ in MeOH)/$CH_2Cl_2$)to give 8.12 g of the product compound. Mass Spec.: $MH^+$=182.15

Step B

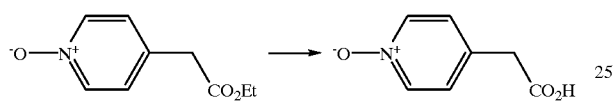

Combine 3.5 g (19.3 mmol) of the product of Step A, 17.5 mL of EtOH and 96.6 mL of 10% NaOH (aqueous) and heat the mixture at $67°$ C. for 2 hours. Add 2 N HCl (aqueous) to adjust to pH=2.37 and concentrate in vacuo to a residue. Add 200 mL of dry EtOH, filter through celite® and wash the filter cake with dry EtOH (2×50 ml). Concentrate the combined filtrates in vacuo to give 2.43 g of the title compound.

Preparative Example 2

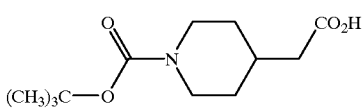

The title compound is prepared via the process disclosed in PCT International Publication No. WO95/10516.

Preparative Example 3

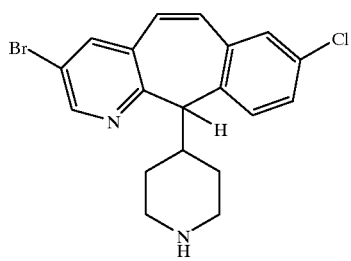

Step A

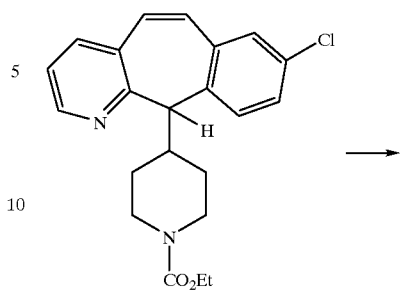

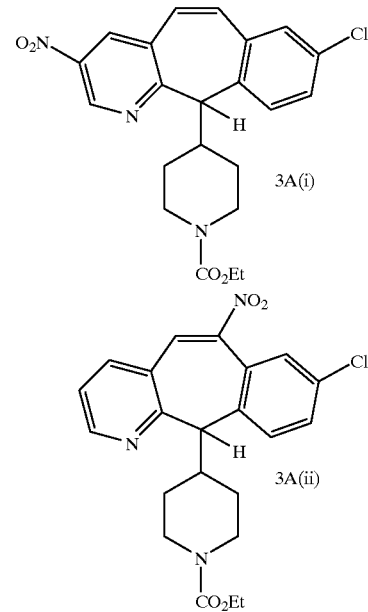

Combine 14.95 g (39 mmol) of 8-chloro-11-(1-ethoxycarbonyl-4-piperidinyl)-11H-benzo[5,6]cyclohepta[1,2-b]pyridine and 150 mL of $CH_2Cl_2$, then add 13.07 g (42.9 mmol) of $(nBu)_4NNO_3$ and cool the mixture to $0°$ C. Slowly add (dropwise) a solution of 6.09 mL (42.9 mmol) of TFAA in 20 mL of $CH_2Cl_2$ over 1.5 hours. Keep the mixture at $0°$ C. overnight, then wash successively with saturated $NaHCO_3$ (aqueous), water and brine. Dry the organic solution over $Na_2SO_4$, concentrate in vacuo to a residue and chromatograph the residue (silica gel, EtOAc/hexane gradient) to give 4.32 g and 1.90 g of the two product compounds 3A(i) and 3A(ii), respectively.

Mass Spec. for compound 3A(i): $MH^+$=428.2.

Mass Spec. for compound 3A(ii): $MH^+$=428.3.

Step B

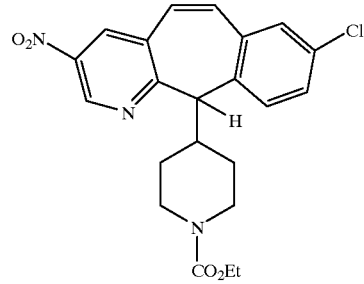

-continued

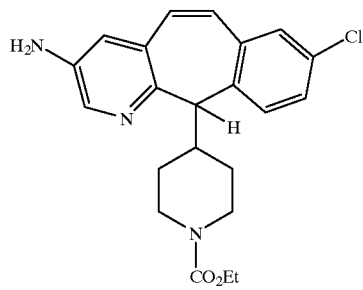

Combine 22.0 g (51.4 mmol) of the product 3A(i) from Step A, 150 mL of 85% EtOH (aqueous), 25.85 g (0.463 mole) of Fe powder and 2.42 g (21.8 mmol) of CaCl$_2$, and heat at reflux overnight. Add 12.4 g (0.222 mole) of Fe powder and 1.2 g (10.8 mmol) of CaCl$_2$ and heat at reflux for 2 hours. Add another 12.4 g (0.222 mole) of Fe powder and 1.2 g (10.8 mmol) of CaCl$_2$ and heat at reflux for 2 hours more. Filter the hot mixture through celite®, wash the celite® with 50 mL of hot EtOH and concentrate the filtrate in vacuo to a residue. Add 100 mL of anhydrous EtOH, concentrate to a residue and chromatograph the residue (silica gel, MeOH/CH$_2$Cl$_2$ gradient) to give 16.47 g of the product compound. MH$^+$=398.

Step C

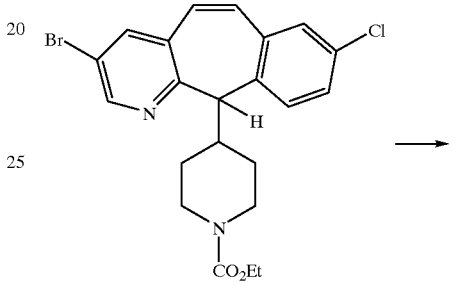

3C(i)

3C(ii)

Combine 16.47 g (41.4 mmol) of the product from Step B, and 150 mL of 48% HBr (aqueous) and cool to −3° C. Slowly add (dropwise) 18 mL of bromine, then slowly add (dropwise) a solution of 8.55 g (0.124 mole) of NaNO$_2$ in 85 mL of water. Stir for 45 minutes at −3° to 0° C., then adjust to pH=10 by adding 50% NaOH (aqueous). Extract with EtOAc, wash the extracts with brine and dry the extracts over Na$_2$SO$_4$. Concentrate to a residue and chromatograph (silica gel, EtOAc/hexane gradient) to give 10.6 g and 3.28 g of the two product compounds 3C(i) and 3C(ii), respectively.

Mass Spec. for compound 3C(i): MH$^+$=461.2.

Mass Spec. for compound 3C(ii): MH$^+$=539.

Step D

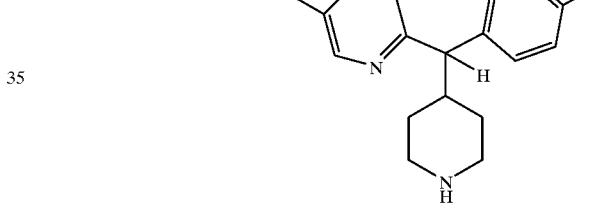

Hydrolyze the product 3C(i) of Step C by dissolving in concentrated HCl and heating to about 100° C. for 16 hours. Cool the mixture, then neutralize with 1 M NaOH (aqueous). Extract with CH$_2$Cl$_2$, dry the extracts over MgSO$_4$, filter and concentrate in vacuo to the title compound. Mass Spec.: MH$^+$=466.9.

Preparative Example 4

Step A

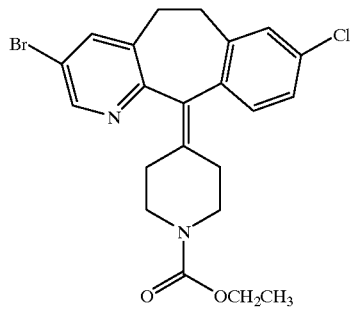

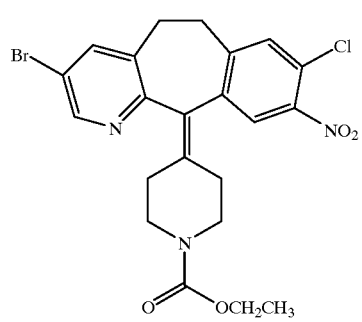

Combine 25.86 g (55.9 mmol) of 4-(8-chloro-3-bromo-5,6-dihydro-11H-benzo[5,6]cyclohepta[1,2-b]pyridin-11-ylidene)-1-piperidine-1-carboxylic acid ethyl ester and 250 mL of concentrated $H_2SO_4$ at −5° C., then add 4.8 g (56.4 mmol) of $NaNO_3$ and stir for 2 hours. Pour the mixture into 600 g of ice and basify with concentrated $NH_4OH$ (aqueous). Filter the mixture, wash with 300 mL of water, then extract with 500 mL of $CH_2Cl_2$. Wash the extract with 200 mL of water, dry over $MgSO_4$, then filter and concentrate in vacuo to a residue. Chromatograph the residue (silica gel, 10% EtOAc/$CH_2Cl_2$) to give 24.4 g (86% yield) of the product. m.p.=165–167° C., Mass Spec.: $MH^+$=506 (CI).

Elemental analysis:

calculated—C, 52.13; H, 4.17; N, 8.29
found—C, 52.18; H, 4.51; N, 8.16.

Step B

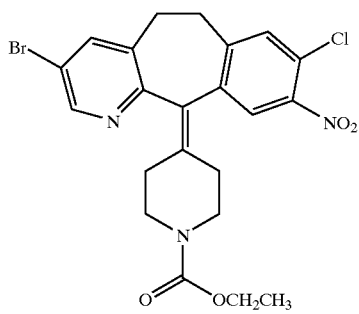

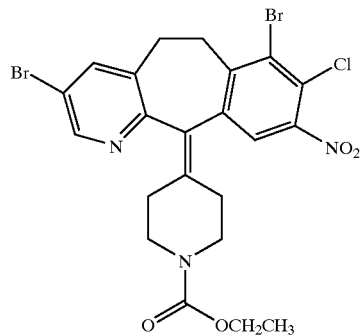

Combine 20 g (40.5 mmol) of the product of Step A and 200 mL of concentrated $H_2SO_4$ at 20° C., then cool the mixture to 0° C. Add 7.12 g (24.89 mmol) of 1,3-dibromo-5,5-dimethylhydantoin to the mixture and stir for 3 hours at 20° C. Cool to 0° C., add an additional 1.0 g (3.5 mmol) of the dibromohydantoin and stir at 20° C. for 2 hours. Pour the mixture into 400 g of ice, basify with concentrated $NH_4OH$ (aqueous) at 0° C., and collect the resulting solid by filtration. Wash the solid with 300 mL of water, slurry in 200 mL of acetone and filter to provide 19.79 g (85.6% yield) of the product. m.p.=236–237° C., Mass Spec.: $MH^+$=584 (CI).

Elemental analysis:

calculated—C, 45.11; H, 3.44; N, 7.17
found—C, 44.95; H, 3.57; N, 7.16.

Step C

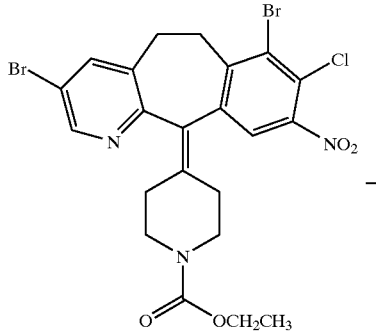

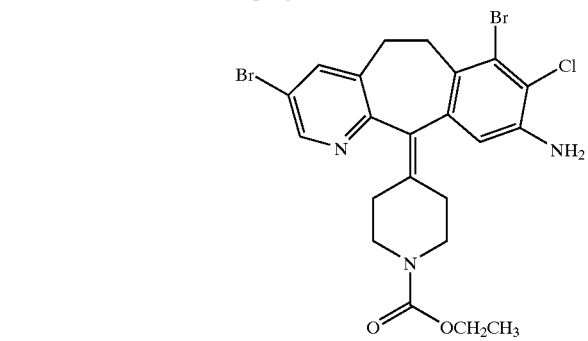

Combine 25 g (447 mmol) of Fe filings, 10 g (90 mmol) of $CaCl_2$ and a suspension of 20 g (34.19 mmol) of the product of Step B in 700 mL of 90:10 EtOH/water at 50° C. Heat the mixture at reflux overnight, filter through Celite® and wash the filter cake with 2×200 mL of hot EtOH. Combine the filtrate and washes, and concentrate in vacuo to a residue. Extract the residue with 600 mL of $CH_2Cl_2$, wash with 300 mL of water and dry over MgSO4. Filter and concentrate in vacuo to a residue, then chromatograph (silica gel, 30% EtOAc/CH₂Cl₂) to give 11.4 g (60% yield) of the product. m.p.=211–212° C., Mass Spec.: MH⁺=554 (CI).

Elemental analysis:
calculated—C, 47.55; H, 3.99; N, 7.56
found—C, 47.45; H, 4.31; N, 7.49.

Step D

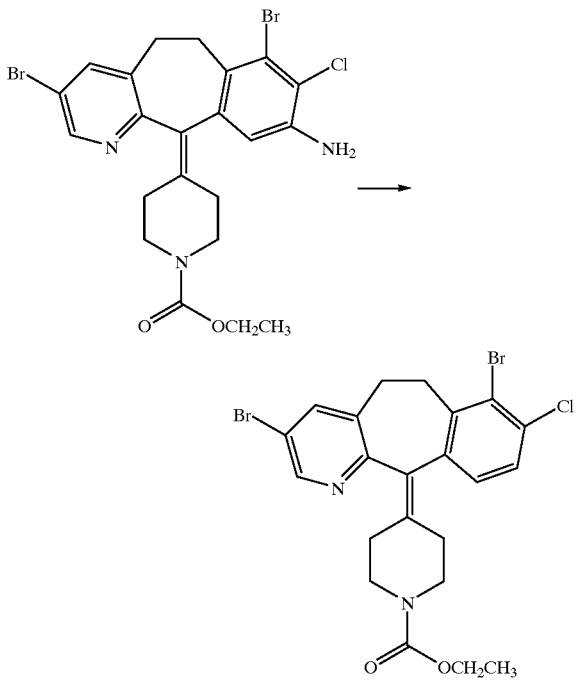

Slowly add (in portions) 20 g (35.9 mmol) of the product of Step C to a solution of 8 g (116 mmol) of NaNO₂ in 120 mL of concentrated HCl (aqueous) at −10 ° C. Stir the resulting mixture at 0° C. for 2 hours, then slowly add (dropwise) 150 mL (1.44 mole) of 50% H₃PO₂ at 0° C. for 3 hours, then pour into 600 g of ice and basify with concentrated NH₄OH (aqueous). Extract with 2×300 mL of CH₂Cl₂, dry the extracts over MgSO₄, then filter and concentrate in vacuo to a residue. Chromatograph the residue (silica gel, 25% EtOAc/hexanes) to give 13.67 g (70% yield) of the product. m.p.=163–165° C., Mass Spec.: MH⁺=539 (CI).

Elemental analysis:
calculated—C, 48.97; H, 4.05; N, 5.22
found—C, 48.86; H, 3.91; N, 5.18.

Step E

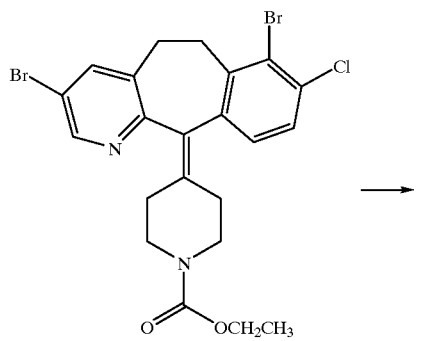

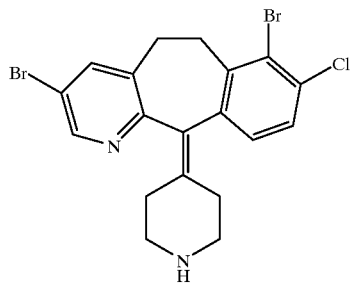

Combine 6.8 g (12.59 mmol) of the product of Step D and 100 mL of concentrated HCl (aqueous) and stir at 85° C. overnight. Cool the mixture, pour it into 300 g of ice and basify with concentrated NH₄OH (aqueous). Extract with 2×300 mL of CH₂Cl₂, then dry the extracts over MgSO₄. Filter, concentrate in vacuo to a residue, then chromatograph (silica gel, 10% MeOH/EtOAc+2% NH₄OH (aqueous)) to give 5.4 g (92% yield) of the title compound. m.p.=172–174° C., Mass Spec.: MH⁺=467.

Elemental analysis:
calculated—C, 48.69; H, 3.65; N, 5.97
found—C, 48.83; H, 3.80; N, 5.97.

Preparative Example 5

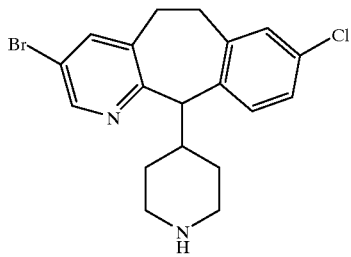

Step A

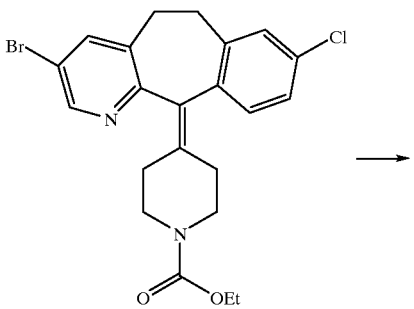

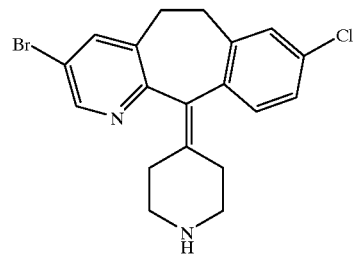

Hydrolyze 2.42 g of 4-(8-chloro-3-bromo-5,6-dihydro-11H-benzo[5,6]cyclohepta[1,2-b]pyridin-11-ylidene)-1-piperidine-1-carboxylic acid ethyl ester via substantially the same procedure as described in Preparative Example 3, Step D, to give 1.39 g (69% yield) of the product. MH+=389.

Step B

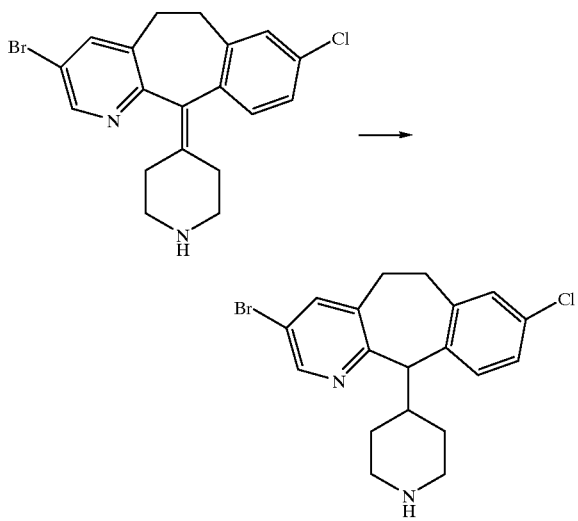

Combine 1 g (2.48 mmol) of the product of Step A and 25 mL of dry toluene, add 2.5 mL of 1 M DIBAL in toluene and heat the mixture at reflux. After 0.5 hours, add another 2.5 mL of 1 M DIBAL in toluene and heat at reflux for 1 hour. (The reaction is monitored by TLC using 50% MeOH/ CH$_2$Cl$_2$ +NH$_4$OH (aqueous).) Cool the mixture to room temperature, add 50 mL of 1 N HCl (aqueous) and stir for 5 min. Add 100 mL of 1 N NaOH (aqueous), then extract with EtOAc (3×150 mL). Dry the extracts over MgSO$_4$, filter and concentrate in vacuo to give 1.1 g of the title compound. MH+=391.

Preparative Example 6

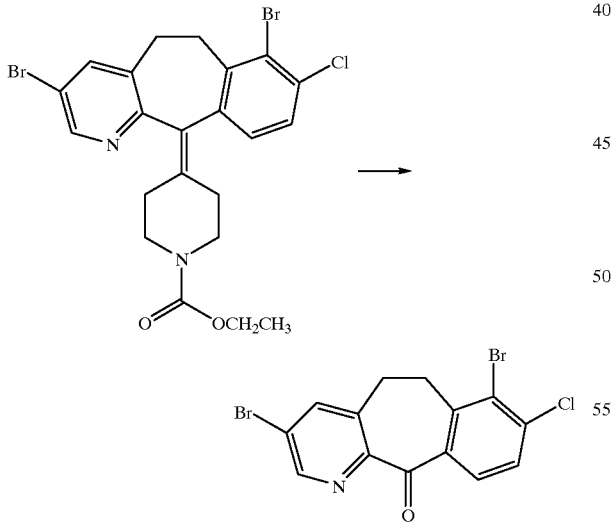

Combine 16.6 g (0.03 mole) of the product of Preparative Example 4, Step D, with a 3:1 solution of CH$_3$CN and water (212.65 mL CH$_3$CN and 70.8 mL of water) and stir the resulting slurry overnight at room temperature. Add 32.833 g (0.153 mole) of NaIO$_4$ and then 0.31 g (2.30 mmol) of RuO$_2$ and stir at room temperature (the addition of RuO$_2$ is accompanied by an exothermic reaction and the temperature climbs from 20° to 30° C.). Stir the mixture for 1.3 hrs. (temperature returned to 25° C. after about 30 min.), then filter to remove the solids and wash the solids with CH$_2$Cl$_2$. Concentrate the filtrate in vacuo to a residue and dissolve the residue in CH$_2$Cl$_2$. Filter to remove insoluble solids and wash the solids with CH$_2$Cl$_2$. Wash the filtrate with water, concentrate to a volume of about 200 mL and wash with bleach, then with water. Extract with 6 N HCl (aqueous). Cool the aqueous extract to 0° C. and slowly add 50% NaOH (aqueous) to adjust to pH=4 while keeping the temperature <30° C. Extract twice with CH$_2$Cl$_2$, dry over MgSO$_4$ and concentrate in vacuo to a residue. Slurry the residue in 20 mL of EtOH and cool to 0° C. Collect the resulting solids by filtration and dry the solids in vacuo to give 7.95 g of the product. $^1$H NMR (CDCl$_3$, 200 MHz): 8.7 (s, 1H); 7.85 (m, 6H); 7.5 (d, 2H); 3.45 (m, 2H); 3.15 (m, 2H).

Preparative Example 7

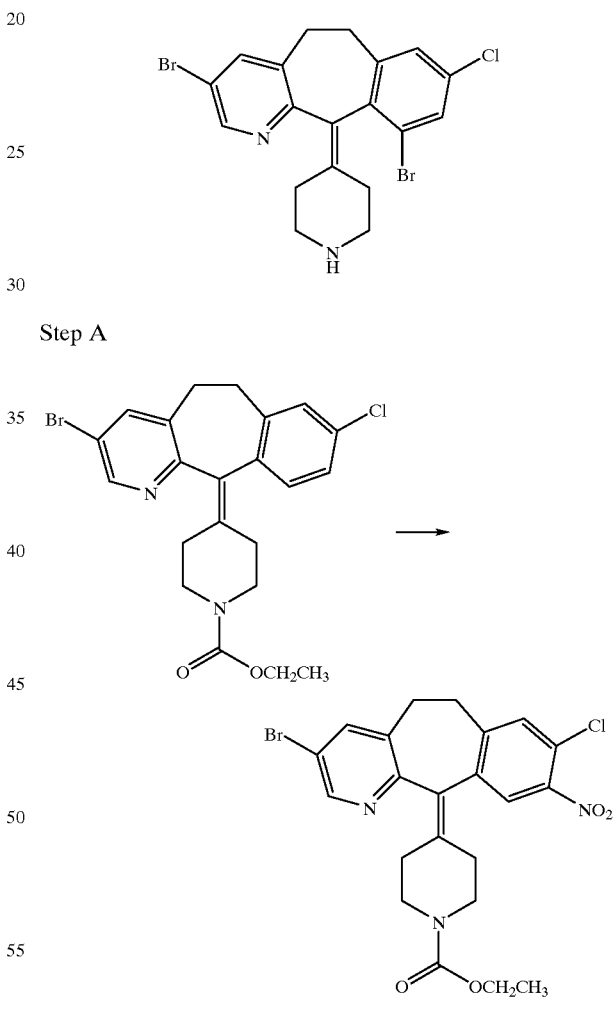

Step A

Combine 15 g (38.5 mmol) of 4-(8-chloro-3-bromo-5,6-dihydro-1 1H-benzo[5,6]cyclohepta[1 ,2-b]pyridin-1 1-ylidene)-1-piperidine-1-carboxylic acid ethyl ester and 150 mL of concentrated H$_2$SO$_4$ at −5° C., then add 3.89 g (38.5 mmol) of KNO$_3$ and stir for 4 hours. Pour the mixture into 3 L of ice and basify with 50% NaOH (aqueous). Extract with CH$_2$Cl$_2$, dry over MgSO$_4$, then filter and concentrate in vacuo to a residue. Recrystallize the residue from acetone to give 6.69 g of the product. $^1$H NMR (CDCl$_3$, 200 MHz): 8.5 (s, 1H); 7.75 (s, 1H); 7.6 (s, 1H); 7.35 (s, 1H); 4.15 (q, 2H); 3.8 (m, 2H); 3.5–3.1 (m, 4H); 3.0–2.8 (m, 2H); 2.6–2.2 (m, 4H); 1.25 (t, 3H). MH⁺=506.

Step B

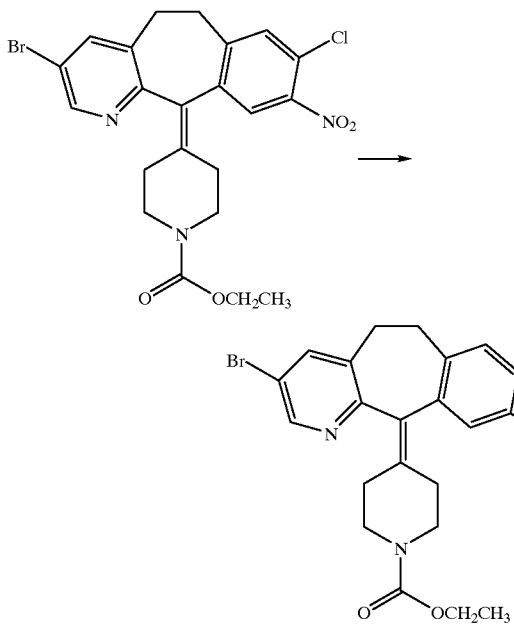

Combine 6.69 g (13.1 mmol) of the product of Step A and 100 mL of 85% EtOH/water, then add 0.66 g (5.9 mmol) of CaCl$_2$ and 6.56 g (117.9 mmol) of Fe and heat the mixture at reflux overnight. Filter the hot reaction mixture through Celite® and rinse the filter cake with hot EtOH. Concentrate the filtrate in vacuo to give 7.72 g of the product. Mass Spec.: MH⁺=476.0.

Step C

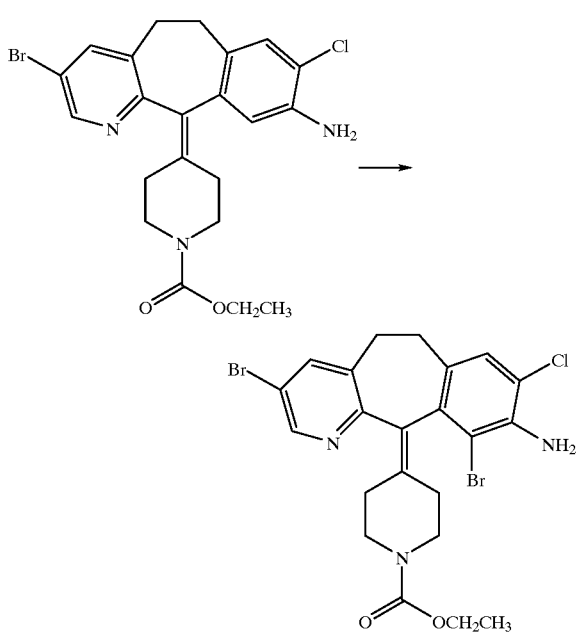

Combine 7.70 g of the product of Step B and 35 mL of HOAc, then add 45 mL of a solution of Br$_2$ in HOAc and stir the mixture at room temperature overnight. Add 300 mL of 1 N NaOH (aqueous), then 75 mL of 50% NaOH (aqueous) and extract with EtOAc. Dry the extract over MgSO$_4$ and concentrate in vacuo to a residue. Chromatograph the residue (silica gel, 20%–30% EtOAc/hexane) to give 3.47 g of the product (along with another 1.28 g of partially purified product). Mass Spec.: MH⁺=554.

$^1$H NMR (CDCl$_3$, 300 MHz): 8.5 (s, 1H); 7.5 (s, 1H); 7.15 (s, 1H); 4.5 (s, 2H); 4.15 (m, 3H); 3.8 (br s, 2H); 3.4–3.1 (m, 4H); 9–2.75 (m, 1H); 2.7–2.5 (m, 2H); 2.4–2.2 (m, 2H); 1.25 (m, 3H).

Step D

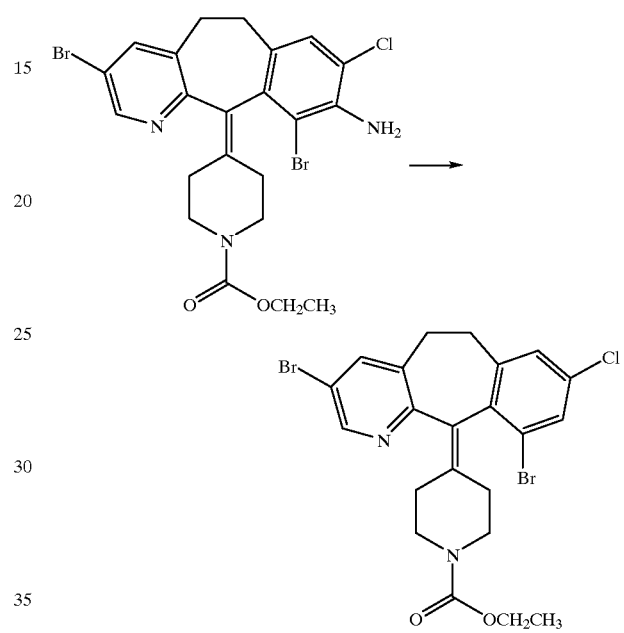

Combine 0.557 g (5.4 mmol) of t-butylnitrite and 3 mL of DMF, and heat the mixture at 60°–70° C. Slowly add (dropwise) a mixture of 2.00 g (3.6 mmol) of the product of Step C and 4 mL of DMF, then cool the mixture to room temperature. Add another 0.64 mL of t-butylnitrite at 40° C. and reheat the mixture to 60°–70° C. for 0.5 hrs. Cool to room temperature and pour the mixture into 150 mL of water. Extract with CH$_2$Cl$_2$, dry the extract over MgSO$_4$ and concentrate in vacuo to a residue. Chromatograph the residue (silica gel, 10%–20% EtOAc/hexane) to give 0.74 g of the product. Mass Spec.: MH⁺=539.0.

$^1$H NMR (CDCl3, 200 MHz): 8.52 (s, 1H); 7.5 (d, 2H); 7.2 (s, 1H); 4.15 (q, 2H); 3.9–3.7 (m, 2H); 3.5–3.1 (m, 4H); 3.0–2.5 (m, 2H); 2.4–2.2 (m, 2H); 2.1–1.9 (m, 2H); 1.26 (t, 3H).

Step E

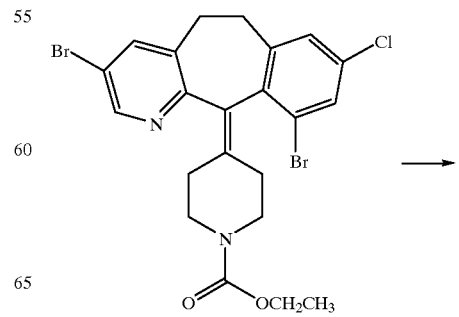

-continued

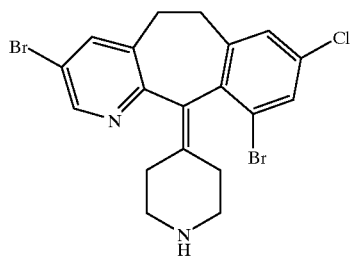

Combine 0.70 g (1.4 mmol) of the product of Step D and 8 mL of concentrated HCl (aqueous) and heat the mixture at reflux overnight. Add 30 mL of 1 N NaOH (aqueous), then 5 mL of 50% NaOH (aqueous) and extract with $CH_2Cl_2$. Dry the extract over $MgSO_4$ and concentrate in vacuo to give 0.59 g of the title compound. Mass Spec.: $MH^+$=467. m.p.=123.9°–124.2° C.

Preparative Example 8

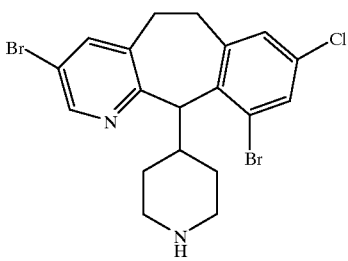

[racemic as well as (+)- and (-)-enantiomers]

Step A

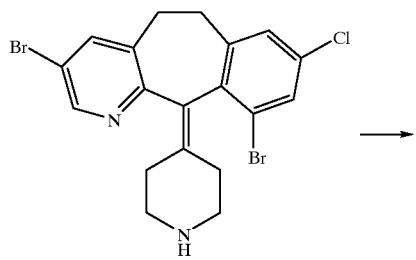

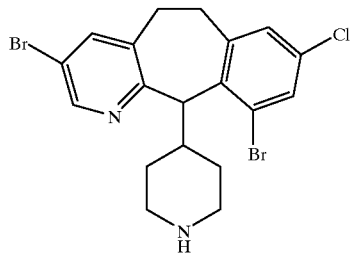

Prepare a solution of 8.1 g of the title compound from Preparative Example 7 in toluene and add 17.3 mL of a 1M solution of DIBAL in toluene. Heat the mixture at reflux and slowly add (dropwise) another 21 mL of 1 M DIBAL/toluene solution over a period of 40 min. Cool the reaction mixture to about 0° C. and add 700 mL of 1 M HCl (aqueous). Separate and discard the organic phase. Wash the aqueous phase with $CH_2Cl_2$, discard the extract, then basify the aqueous phase by adding 50% NaOH (aqueous). Extract with $CH_2Cl_2$, dry the extract over $MgSO_4$ and concentrate in vacuo to give 7.30 g of the title compound, which is a racemic mixture of enantiomers. $MH^+$=469.

Step B—Separation of Enantiomers

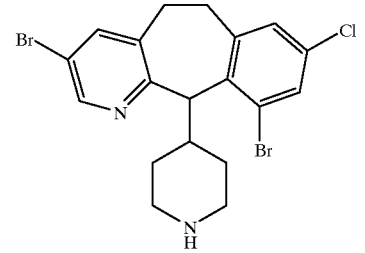

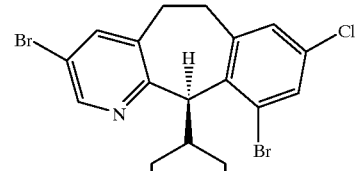

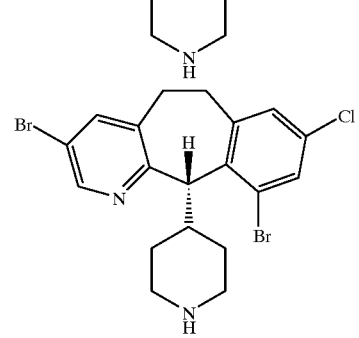

The racemic title compound of Step A is separated by preparative chiral chromatography (Chiralpack AD, 5 cm×50 cm column, using 20% iPrOH/hexane+0.2% diethylamine), to give the (+)-enantiomer and the (-)-enantiomer of the title compound.

Physical chemical data for (+)-enantiomer: m.p.=148.8° C.; Mass Spec. $MH^+$=469; $[\alpha]_D^{25}$=+65.6° (12.93mg/2mL MeOH).

Physical chemical data for (-)-enantiomer: m.p.=112° C.; Mass Spec. $MH^+$=469; $[\alpha]_D^{25}$=-65.2° (3.65mg/2mL MeOH).

Preparative Example 9

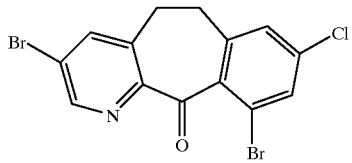

Step A

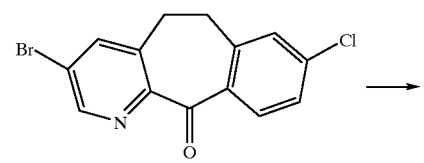

-continued

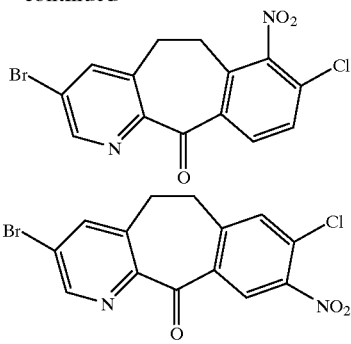

Combine 40.0 g (0.124 mole) of the starting ketone and 200 mL of H₂SO₄ and cool to 0° C. Slowly add 13.78 g (0.136 mole) of KNO₃ over a period of 1.5 hrs., then warm to room temperature and stir overnight. Work up the reaction using substantially the same procedure as described for Preparative Example 4, Step A. Chromatograph (silica gel, 20%, 30%, 40%, 50% EtOAc/hexane, then 100% EtOAc) to give 28 g of the 9-nitro product, along with a smaller quantity of the 7-nitro product and 19 g of a mixture of the 7-nitro and 9-nitro compounds. MH⁺(9-nitro)=367.

Step B

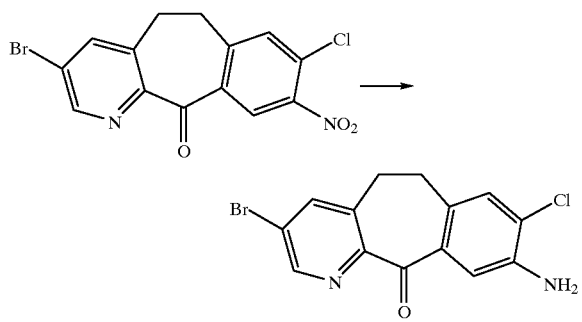

React 28 g (76.2 mmol) of the 9-nitro product of Step A, 400 mL of 85% EtOH/water, 3.8 g (34.3 mmol) of CaCl₂ and 38.28 g (0.685 mole) of Fe using substantially the same procedure as described for Preparative Example 4, Step C, to give 24 g of the product. MH⁺=337.

Step C

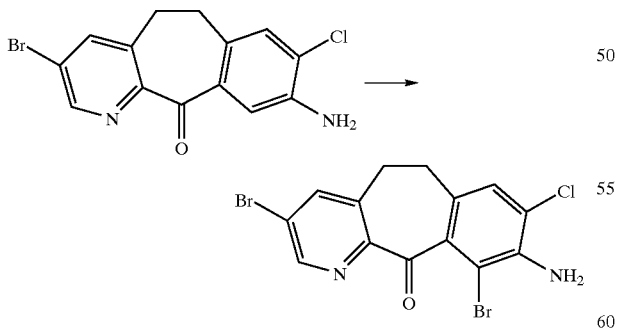

Combine 13 g (38.5 mmol) of the product of Step B, 140 mL of HOAc and slowly add a solution of 2.95 mL (57.8 mmol) of Br₂ in 10 mL of HOAc over a period of 20 min. Stir the reaction mixture at room temperature, then concentrate in vacuo to a residue. Add CH₂Cl₂ and water, then adjust to pH=8–9 with 50% NaOH (aqueous). Wash the organic phase with water, then brine and dry over Na₂SO₄. Concentrate in vacuo to give 11.3 g of the product. ¹H NMR (200 MHZ, CDCl₃): 8.73 (d, 1H); 7.74 (d, 1H); 7.14 (s, 1H); 4.63 (s, 2H); 3.23–3.15 (m, 2H); and 3.07–2.98 (m, 2H).

Step D

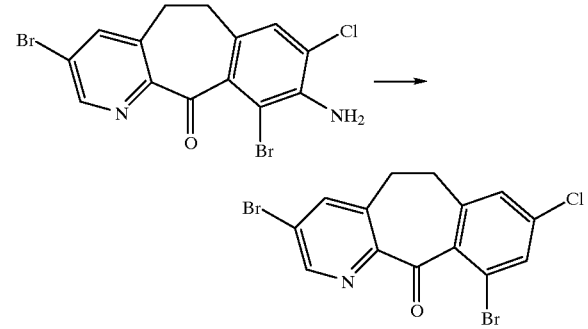

Cool 100 mL of concentrated HCl (aqueous) to 0° C., then add 5.61 g (81.4 mmol) of NaNO₂ and stir for 10 min. Slowly add (in portions) 11.3 g (27.1 mmol) of the product of Step C and stir the mixture at 0°–3° C. for 2.25 hrs. Slowly add (dropwise) 180 mL of 50% H₃PO₂ (aqueous) and allow the mixture to stand at 0° C. overnight. Slowly add (dropwise) 150 mL of 50% NaOH over 30 min., to adjust to pH=9, then extract with CH₂Cl₂. Wash the extract with water, then brine and dry over Na₂SO₄. Concentrate in vacuo to a residue and chromatograph (silica gel, 2% EtOAc/CH₂Cl₂) to give 8.6 g of the product. MH⁺=399.9.

¹H NMR (200 MHZ, CDCl₃): 8.75 (d, 1H); 7.77 (d, 1H); 7.56 (d, 1H); 7.21 (d, 1H); and 3.3–3.0 (m, 4H).

Preparative Example 10

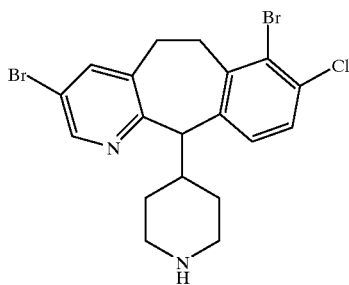

Racemic as well as
(+)- and (-)-enantiomer

Step A

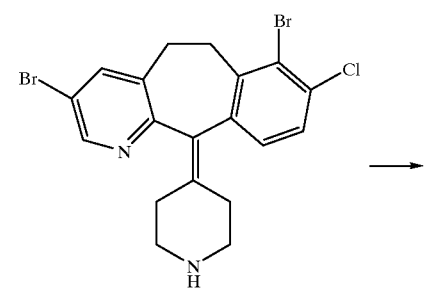

-continued

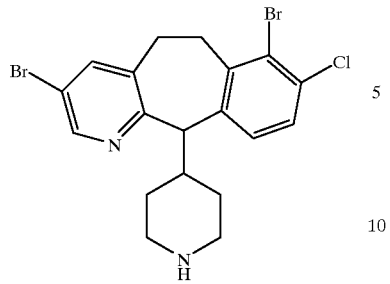

Combine 13 g (33.3 mmol) of the title compound from Preparative Example 4, Step D, and 300 mL of toluene at 20° C., then add 32.5 mL (32.5 mmol) of a 1 M solution of DIBAL in toluene. Heat the mixture at reflux for 1 hr., cool to 20° C., add another 32.5 mL of 1 M DIBAL solution and heat at reflux for 1 hr. Cool the mixture to 20° C. and pour it into a mixture of 400 g of ice, 500 mL of EtOAc and 300 mL of 10% NaOH (aqueous). Extract the aqueous layer with $CH_2Cl_2$ (3×200 mL), dry the organic layers over $MgSO_4$, then concentrate in vacuo to a residue. Chromatograph (silica gel, 12% $MeOH/CH_2Cl_2$+4% $NH_4OH$) to give 10.4 g of the title compound as a racemate. Mass Spec.: $MH^+$=469 (FAB). partial $^1H$ NMR ($CDCl_3$, 400 MHz): 8.38 (s, 1H); 7.57 (s, 1H); 7.27 (d, 1H); 7.06 (d, 1H); 3.95 (d, 1H).

Step B—Separation of Enantiomers

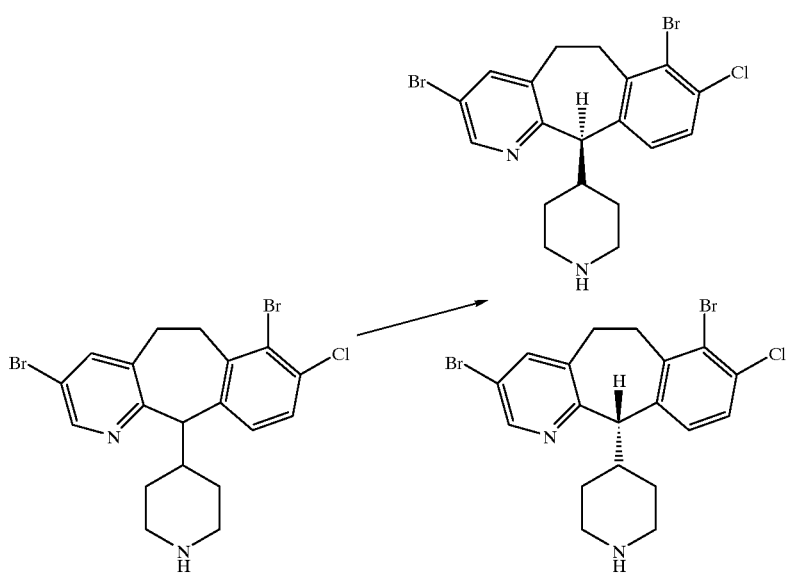

The racemic title compound of Step A is separated by preparative chiral chromatography (Chiralpack AD, 5cm×50 cm column, using 5% iPrOH/hexane+0.2% diethylamine), to give the (+)-enantiomer and the (−)-enantiomer of the title compound.

Physical chemical data for (+)-enantiomer: Mass Spec. $MH^+$=469 (FABS); $[\alpha]_D^{25}$=+43.5° (c=0.402, EtOH); partial $^1H$ NMR ($CDCl_3$, 400 MHz): 8.38 (s, 1H); 7.57 (s, 1H); 7.27 (d, 1H); 7.05 (d, 1H); 3.95 (d, 1H).

Physical chemical data for (−)-enantiomer: Mass Spec. $MH^+$=469 (FAB); $[\alpha]_D^{25}$=−41.80° (c=0.328 EtOH); partial $^1H$ NMR ($CDCl_3$, 400 MHz): 8.38 (s, 1H); 7.57 (s, 1H); 7.27 (d, 1H); 7.05 (d, 1H); 3.95 (d, 1H).

Preparative Example 11

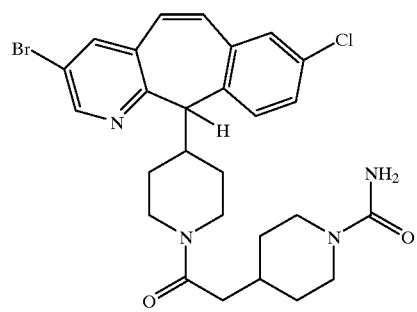

Step A

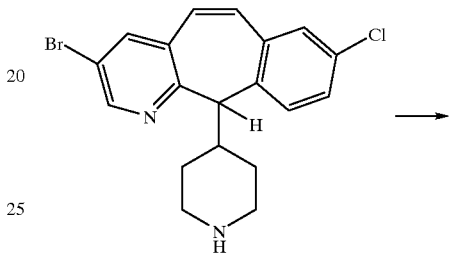

-continued

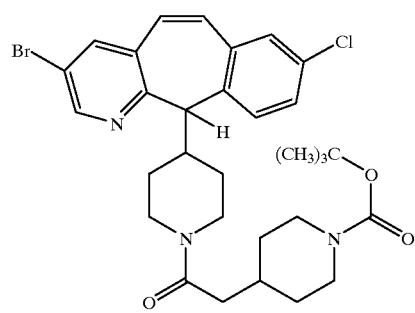

Dissolve 1.160 g (2.98 mmol) of the title compound from Preparative Example 3 in 20 mL of DMF, stir at room temperature, and add 0.3914 g (3.87 mmol) of 4-methylmorpholine, 0.7418 g (3.87 mmol) of DEC, 0.5229 g (3.87 mmol) of HOBT, and 0.8795 g (3.87 mmol) of 1-N-t-butoxycarbonylpiperidinyl-4-acetic acid. Stir the mixture at room temperature for 2 days, then concentrate in vacuo to a residue and partition the residue between $CH_2Cl_2$ and water. Wash the organic phase successively with saturated $NaHCO_3$ (aqueous), 10% $NaH_2PO_4$ (aqueous) and brine. Dry the organic phase over $MgSO_4$, filter and concentrate in vacuo to a residue. Chromatograph the residue (silica gel, 2% $MeOH/CH_2Cl_2$ +$NH_3$) to give 1.72 g of the product. m.p.=94.0–94.5° C., Mass Spec.: $MH^+$=614.

Elemental analysis:

calculated—C, 60.54; H, 6.06; N, 6.83 found—C, 59.93; H, 6.62; N, 7.45.

Step B

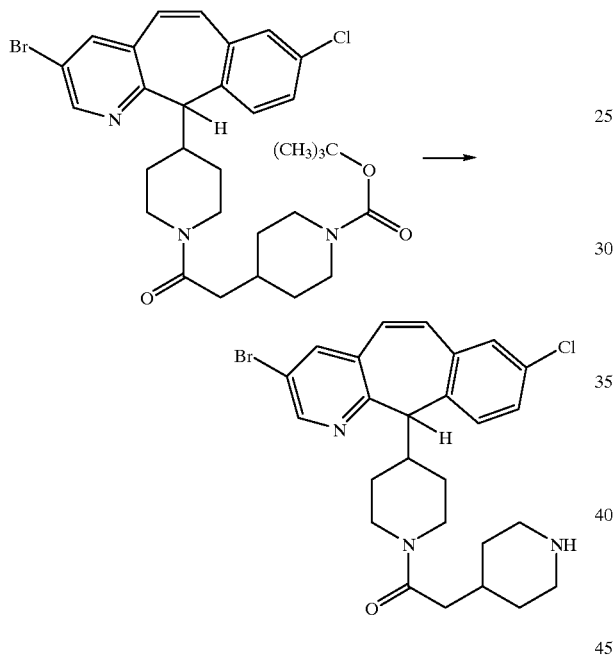

Combine 1.67 g (2.7 mmol) of the product of Step A and 20 mL of $CH_2Cl_2$ and stir at 0° C. Add 20 mL of TFA, stir the mixture for 2 hours, then basify the mixture with 1 N NaOH (aqueous). Extract with $CH_2Cl_2$, dry the organic phase over $MgSO_4$, filter and concentrate in vacuo to give 1.16 g of the product. m.p.=140.2–140.8° C., Mass Spec.: $MH^+$=514.

Step C

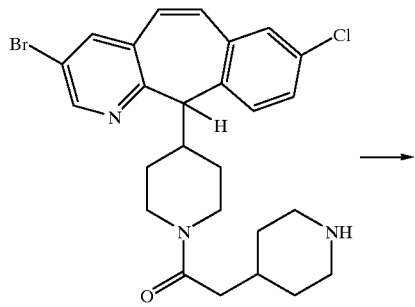

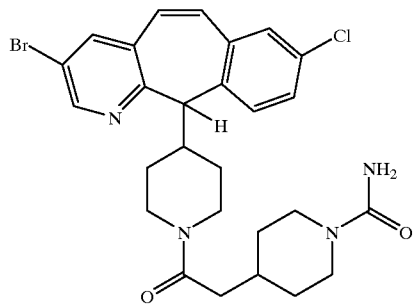

Combine 0.50 g of the product of Step B, 20 mL of $CH_2Cl_2$ and 4.5 equivalents of $(CH_3)_3SiNCO$ and stir at room temperature for 3 hours. Extract the mixture with saturated $NaHCO_3$ (aqueous) and dry the organic phase over $MgSO_4$. Filter and concentrate in vacuo to give 0.8 g of the crude product.

Chromatograph the crude product (silica gel, 5% MeOH/ $CH_2Cl_2$+$NH_3$) to give 0.26 g of the product. m.p.=170.2–170.5° C., Mass Spec.: $MH^+$=557.

Preparative Example 12

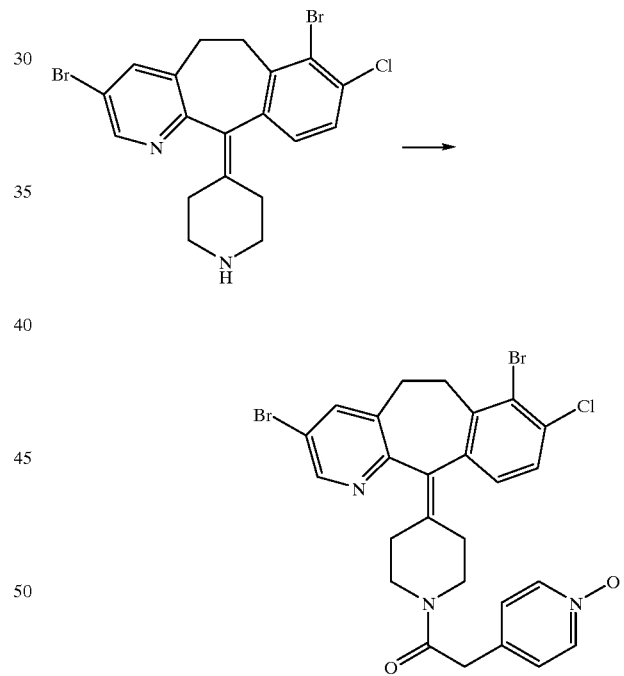

Combine 0.5 g (1.06 mmol) of the title compound of Preparative Example 4, 0.4 g (2.61 mmol) of the title compound of Preparative Example 1, 5 mL of dry DMF, and 0.5 mL (4.53 mmol) of 4-methylmorpholine, at 0° C., then add 0.6 g (3.12 mmol) of DEC and 0.4 g (2.96 mmol) of HOBT and stir the mixture overnight at 20° C. Concentrate in vacuo to a residue and extract the residue with $CH_2Cl_2$ (2×50 mL). Wash the extracts with 25 mL of water, dry over $MgSO_4$, then concentrate in vacuo to a residue and chromatograph (silica gel, 10% MeOH/EtOAc+2% $NH_4OH$ (aqueous)) to give 0.6 g (93.7% yield) of the title compound. Mass Spec.: $MH^+$=602 (FABS); partial $^1H$ NMR ($CDCl_3$, 300 MHz): 8.48 (s, 1H); 8.16 (d, 2H); 7.61 (s, 1H); 7.29 (m, 1H); 7.18 (d, 2H); 7.04 (d, 1H); 3.71 (s, 2H).

Elemental analysis:
calculated—C, 48.81; H, 4.10; N, 6.57
found—C, 49.10; H, 3.79; N, 6.74.

Preparative Example 13

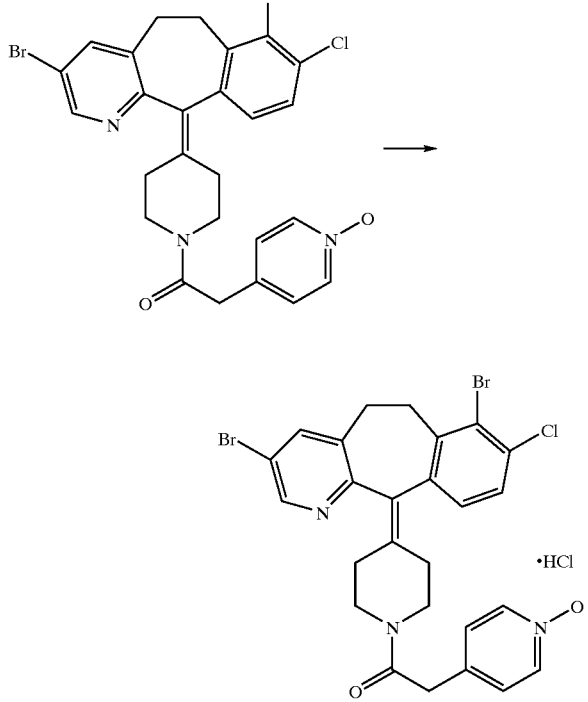

Dissolve 5.9 g (9.78 mmol) of the title compound of Preparative Example 12 in 300 mL of 1:5 CH$_2$Cl$_2$/EtOAc at 0° C. Slowly add (dropwise) 3 mL of 4 N HCl (aqueous) and stir the mixture at 0° C for 5 min. Add 200 mL of Et$_2$O, collect the resulting solids by filtration and wash the solids with 50 mL of Et$_2$O. Dry the solids at 20° C. and 0.2 mm Hg to give 5.9 g (96% yield) of the title compound. Mass Spec.: MH$^+$=602 (FAB). partial $^1$H NMR (DMSO-d$_6$, 300 MHz): δ8.66 (d, 2H); 8.51 (s, 1H); 7.95 (s, 1H); 7.67 (d, 2H); 7.47 (m, 1H); 7.15 (m, 1H); 3.99 (s, 2H).

Elemental analysis:
calculated—C, 48.77; H, 3.62; N, 6.56
found—C, 48.34; H, 3.95; N, 6.84.

Preparative Example 14

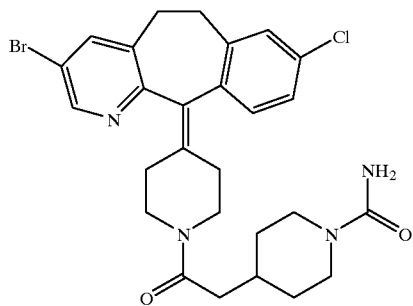

Step A

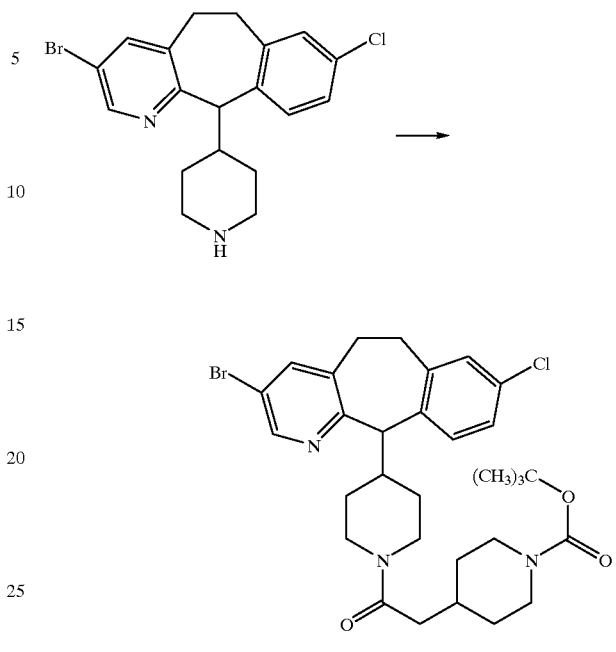

Combine 0.501 g (1.28 mmol) of the compound of Preparative Example 5 and 20 mL of dry DMF, then add 0.405 g (1.664 mmol) of 1-N-t-butoxycarbonylpiperidinyl-4-acetic acid, 0.319 g (1.664 mmol) of DEC, 0.225 g (1.664 mmol) of HOBT, and 0.168 g (1.664 mmol) of 4-methylmorpholine and stir the mixture at room temperature overnight. Concentrate the mixture in vacuo to a residue, then partition the residue between 150 mL of CH$_2$Cl$_2$ and 150 mL of saturated NaHCO$_3$ (aqueous). Extract the aqueous phase with another 150 mL of CH$_2$Cl$_2$. Dry the organic phase over MgSO$_4$, and concentrate in vacuo to a residue. Chromatograph the residue (silica gel, 500 mL hexane, 1 L of 1% MeOH/CH$_2$Cl$_2$+0.1% NH$_4$OH (aqueous), then 1 L of 2% MeOH/CH$_2$Cl$_2$+0.1% NH$_4$OH (aqueous)) to give 0.575 g of the product. m.p.=115°–125° C.; Mass Spec.: MH$^+$=616.

Step B

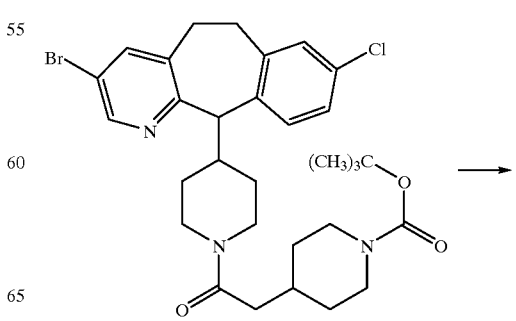

-continued

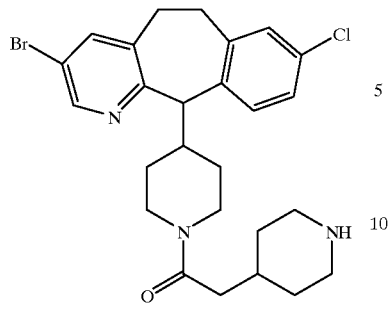

Combine 0.555 g (0.9 mmol) of the product of Step A and 15 mL of CH$_2$Cl$_2$ and cool the mixture to 0° C. Add 15 mL of TFA and stir at 0° C. for 2 hours. Concentrate in vacuo at 40–45° C. to a residue, then partition the residue between 150 mL of CH$_2$Cl$_2$ and 100 mL of saturated NaHCO$_3$ (aqueous). Extract the aqueous layer with 100 mL of CH$_2$Cl$_2$, combine the extracts and dry over MgSO$_4$. Concentrate in vacuo to give 0.47 g of the product. m.p.=140°–150° C.; Mass Spec.: MH$^+$=516.

Step C

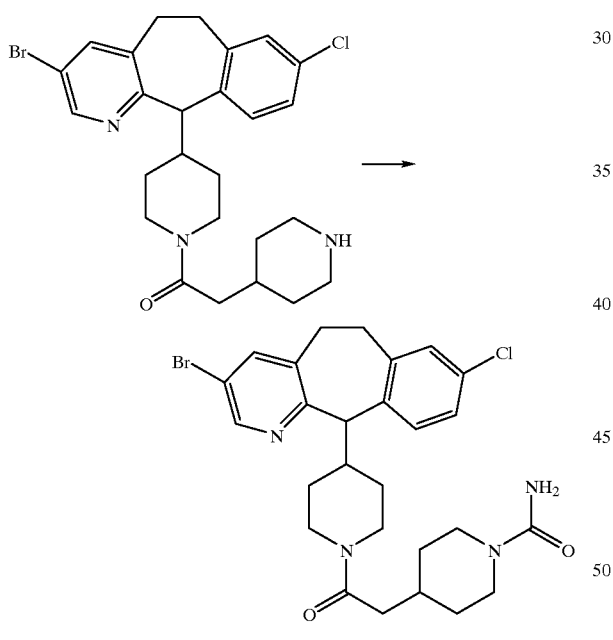

Combine 0.449 g (0.87 mmol) of the product of Step B, 20 mL of CH$_2$Cl$_2$ and 0.501 g (0.59 mmol) of (CH$_3$)$_3$SiNCO and stir at room temperature overnight. Add 50–75 mL of saturated NaHCO$_3$ (aqueous) and stir for 0.5 hours. Dilute with CH$_2$Cl$_2$, separate the layers and extract the aqueous layer with 2×100 mL of CH$_2$Cl$_2$. Dry the combined CH$_2$Cl$_2$ extracts over MgSO$_4$ and concentrate in vacuo to a residue. Chromatograph the residue (silica gel, 500 mL CH$_2$Cl$_2$; 1 L of 1% MeOH/CH$_2$Cl$_2$+0.1% NH$_4$OH; 1 L of 2% MeOH/CH$_2$Cl$_2$+0.2% NE$_4$OH; then with 3% MeOH/CH$_2$Cl$_2$+0.3% NH$_4$OH) to give 0.33 g of the title compound. m.p.=145°–155° C.; Mass Spec.: MH$^+$=559.

Preparative Example 15

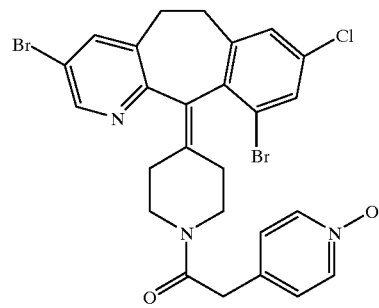

React the title compound of Preparative Example 7 and the title compound of Preparative Example 1 using substantially the same procedure as described for Preparative Example 12, to give 0.25 g of the title compound, which is a racemic mixture of atropisomers. Mass Spec.: MH$^+$=602. m.p.=167.2°–167.8° C.

The HCl salt of the title compound of Preparative Example 15 is prepared by stiffing for 1 hr. with HCl/CH$_2$Cl$_2$, then concentrating in vacuo to give the salt.

Preparative Examples 16A & 16B

Preparative Example 16A

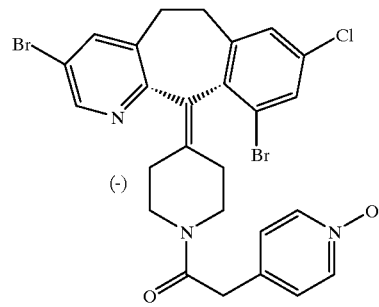

Preparative Example 16B

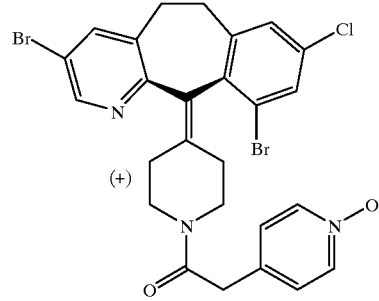

The title compound of Example 15 is a racemic mixture of atropisomers. Those atropisomers are separated by preparative chromatography (HPLC), using an Chiralpack AD column (5 cm×50 cm) and 40% i-PrOH/hexane+0.2% diethylamine as the mobile phase to give the (+)- and (−)-enantiomers, Examples 16B and 16A, respectively.

Physical chemical data for (−)-enantiomer, Example 16A: m.p.=114.2°–114.8° C.; $[\alpha]_D^{25}$=−154.6° (8.73 mg/2 mL, MeOH).

Physical chemical data for (+)-enantiomer, Example 16B: m.p.=112.6°–113.5° C.; $[\alpha]_D^{25}$=+159.70° (10.33 mg/2 mL, MeOH).

Preparative Example 17

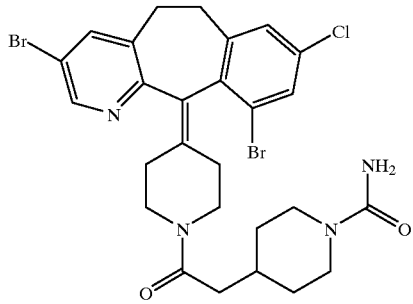

Step A

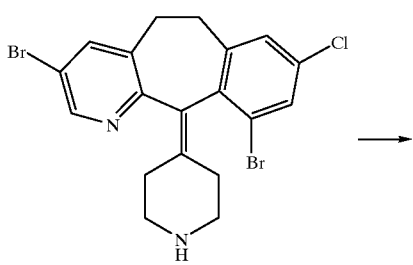

React 6.0 g (12.8 mmol) of the title compound of Preparative Example 7 and with 3.78 g (16.6 mmol) of 1-N-t-butoxycarbonylpiperidinyl-4-acetic acid using substantially the same procedures as described for Preparative Example 14, Step A, to give 8.52 g of the product. Mass Spec.: MH+=692 (FAB). $^1$H NMR (CDCl$_3$, 200 MHz): 8.5 (d, 1H); 7.5 (d, 2H); 7.2 (d, 1H); 4.15–3.9 (m, 3H); 3.8–3.6 (m, 1H); 3.5–3.15 (m, 3H); 2.9 (d, 2H); 2.8–2.5 (m, 4H); 2.4–1.8 (m, 6H); 1.8–1.6 (br d, 2H); 1.4 (s, 9H); 1.25–1.0 (m, 2H).

Step B

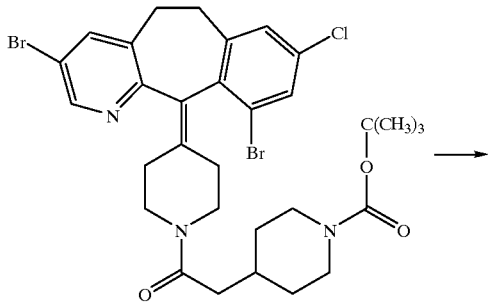

Combine 8.50 g of the product of Step A and 60 mL of CH$_2$Cl$_2$, then cool to 0° C. and add 55 mL of TFA. Stir the mixture for 3 h at 0° C., then add 500 mL of 1 N NaOH (aqueous) followed by 30 mL of 50% NaOH (aqueous). Extract with CH$_2$Cl$_2$, dry over MgSO$_4$ and concentrate in vacuo to give 7.86 g of the product. Mass Spec.: MH+=592 (FAB). $^1$H NMR (CDCl$_3$, 200 MHz): 8.51 (d, 1H); 7.52 (d of d, 2H); 7.20 (d, 1H); 4.1–3.95 (m, 2H); 3.8–3.65 (m, 2H); 3.5–3.05 (m, 5H); 3.0–2.5 (m, 6H); 2.45–1.6 (m, 6H);1.4–1.1 (m, 2H).

Step C

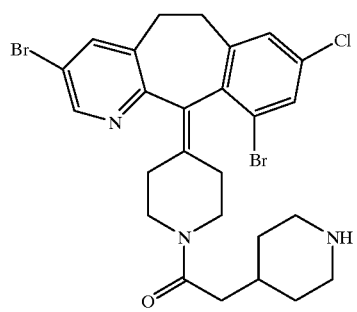

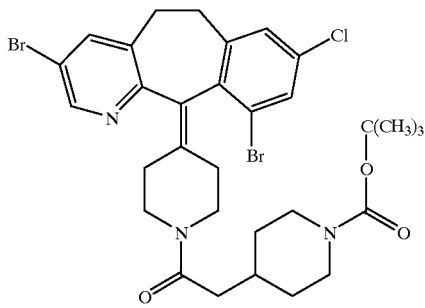

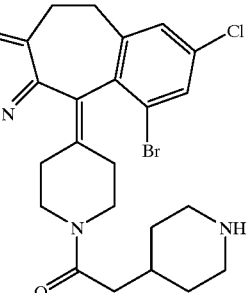

Treat 7.80 g (13.1 mmol) of the product of Step B with 12.1 g (105 mmol) of (CH$_3$)$_3$SiNCO using substantially the same procedure as described for Preparative Example 14, Step C, to give 5.50 g of the title compound, which is a racemic mixture of atropisomers. m.p.=163.6°–164.0° C. Mass spec.: MH+=635 (FAB). $^1$H NMR (CDCl$_3$, 200 MHz): 8.5 (d, 1H); 7.52 (d, 1H); 7.48 (d, 1H); 7.21 (d, 1H); 4.54, (s, 2H); 4.1–3.6 (m, 4H); 3.45–3.15 (m, 4H); 3.0–2.5 (m, 5H); 2.45–1.6 (m, 7H); 1.4–1.0, (m, 2H).

Preparative Examples 18A & 18B

Preparative Example 18A

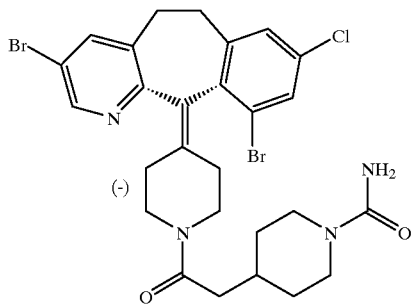

Preparative Example 18B

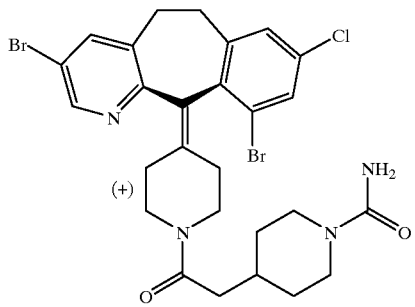

The title compound of Preparative Example 17 is a racemic mixture of atropisomers. Those atropisomers are separated by preparative chromatography (HPLC), using an Chiralpack AD column (5cm×50 cm) and 20% i-PrOH/hexane+0.2% diethylamine as the mobile phase, at a flow rate of 100 mL/min., to give the (+)- and (−)-enantiomers, Examples 18B and 18A, respectively.

Physical chemical data for (−)-enantiomer, Example 18A: m.p.=142.9°–143.5° C.; $[\alpha]_D^{25}$=151.7° (11.06 mg/2 mL, MeOH).

Physical chemical data for (+)-enantiomer, Example 18B: m.p.=126.5°–127.0° C.; $[\alpha]_D^{25}$=+145.60° (8.38 mg/2 mL, MeOH).

Preparative Example 19

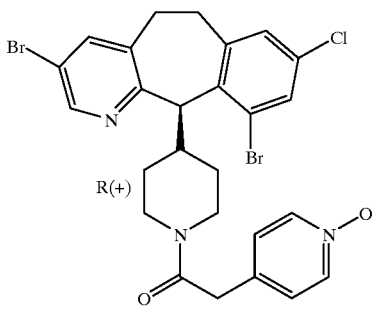

Combine 3.32 g of the (+)-enantiomer of the title compound of Preparative Example 8, Step B, 2.38 g of the title compound of Preparative Example 1, 1.92 g of HOBT, 2.70 g of DEC, 1.56 mL of N-methylmorpholine and 50 mL of dry DMF and stir at 25° C. for 24 hrs. Concentrate in vacuo, then dilute the residue with $CH_2Cl_2$. Wash with 1 N NaOH (aqueous), then with saturated $NaH_2PO_4$ (aqueous) and dry over $MgSO_4$. Concentrate in vacuo to a residue and chromatograph (silica gel, 2% $MeOH/CH_2Cl_2$+$NH_4OH$) to give 3.82 g of the title compound. Mass Spec.: $MH^+$=604 (FAB).

The hydrochloride salt was prepared by dissolution of the title compound from Preparative Example 19 in dichloromethane saturated with hydrogen chloride. Concentration in vacuo provided the title compound from Preparative Example 19 as the HCl salt. m.p.=166.5° C.; $[\alpha]_D^{25}$=+70.80° (9.9mg/2mL MeOH).

Preparative Examples 20A & 20B

Preparative Example 20A

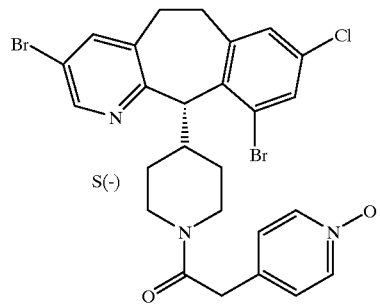

Preparative Example 20B

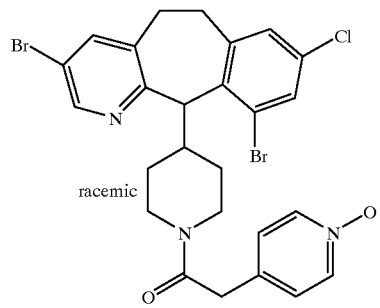

The (−)-enantiomer of the title compound of Preparative Example 8, Step B, (3.38 g) is reacted with 2.20 g of the title compound of Preparative Example 1, via substantially the same procedure as described for Preparative Example 19 to give 3.58 g of the title compound of Preparative Example 20A.

The HCl salt of the title compound of Preparative Example 20A is prepared by dissolving of the title compound in $CH_2Cl_2$, adding 6M HCl (g) in $CH_2Cl_2$, then concentrating in vacuo to give the salt. m.p.=129° C.; $[\alpha]_D^{25}$=−72.3 (3.32mg/2mL MeOH).

The racemic title compound of Preparative Example 8, Step A, is reacted with the title compound of Preparative Example 1, via substantially the same procedure as described for Preparative Example 20A to give the title compound of Preparative Example 20B. m.p.=145.0° C.

Preparative Example 21

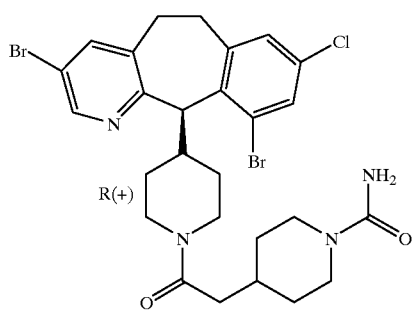

Step A

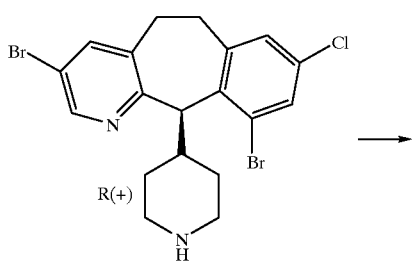

React 1.33 g of the (+)-enantiomer of the title compound of Preparative Example 8, Step B, with 1.37 g of 1-N-t-butoxycarbonylpiperidinyl-4-acetic acid using substantially the same procedures as described for Preparative Example 14, Step A, to give 2.78 g of the product. Mass Spec.: MH$^+$=694.0 (FAB); [α]$_D^{25}$=+34.1° (5.45 mg/2 mL, MeOH).

Step B

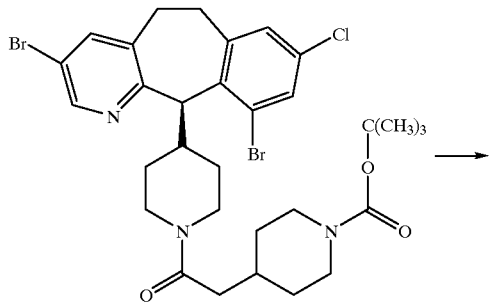

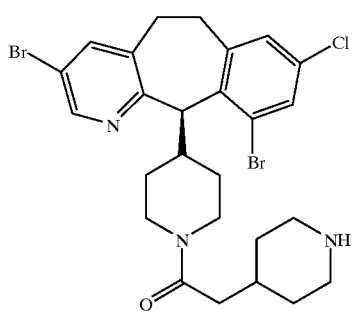

Treat 2.78 g of the product of Step A via substantially the same procedure as described for Preparative Example 17, Step B, to give 1.72 g of the product. m.p.=104.1° C.; Mass Spec.: MH$^+$=594; [α]$_D^{25}$=+53.4° (11.42 mg/2 mL, MeOH).

Step C

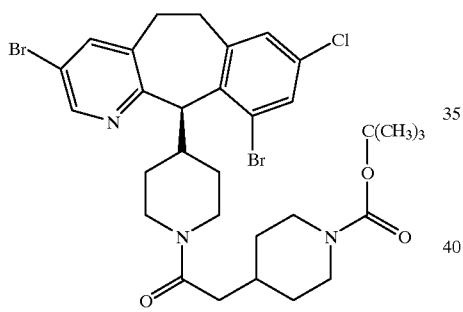

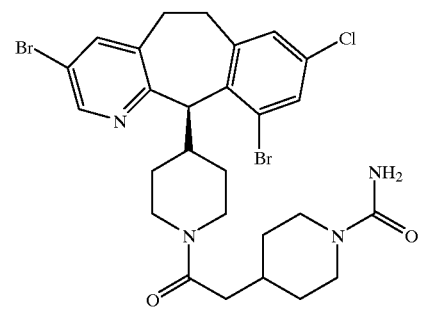

Treat 1.58 g of the product of Step B with 6 mL of (CH$_3$)$_3$SiNCO using substantially the same procedure as described for Preparative Example 14, Step C, to give 1.40 g of the title compound. m.p.=140° C.; Mass spec.: MH$^+$= 637; [α]$_D^{25}$=+49.1° (4.24 mg/2 mL, MeOH).

Recrystallization from acetone provided the title compound as a solid. m.p.=214.5–215.9° C.

Preparative Examples 22A & 22B

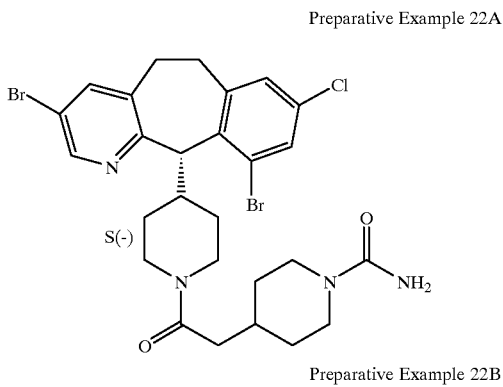

Preparative Example 22A

Preparative Example 22B

The (−)-enantiomer of the title compound of Preparative Example 8, Step B, (3.38 g) is converted to the title compound (Preparative Example 22A) via substantially the same procedure as described for Preparative Example 21, Steps A–C, to give the title compound Preparative Example 22A. m.p.=152° C.; Mass spec.: MH$^+$=637; $[\alpha]_D^{25}$=−62.5° (1,12 mg/2 mL MeOH).

The racemic title compound of Preparative Example 8, Step A, is converted to the title compound (Preparative Example 22B) via substantially the same procedure as described for Preparative Example 10, Steps A–C to give the title compound Preparative Example 22B. m.p.=111.2° C. (dec).

Preparative Example 23

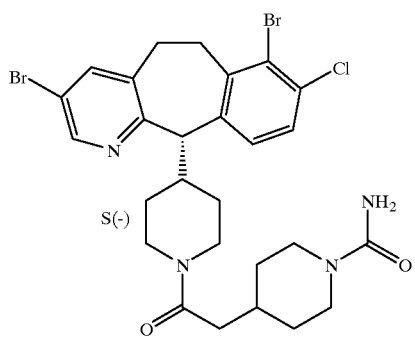

Step A

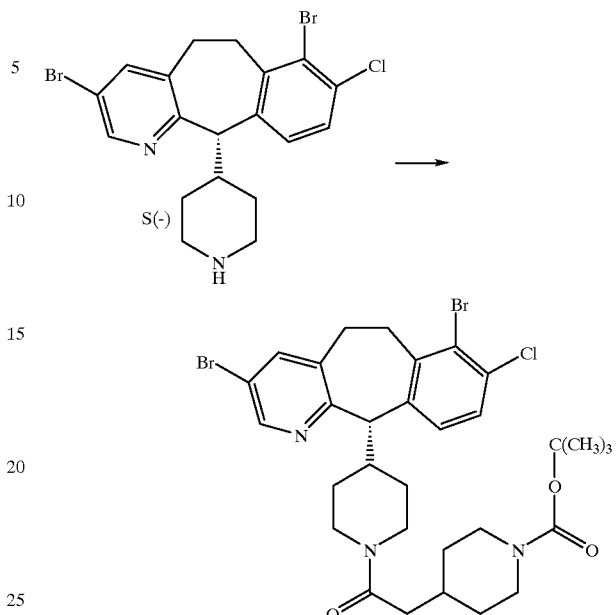

React 1.35 g of the (−)-enantiomer of the title compound of Preparative Example 10, Step B, with 1.4 g of 1-N-t-butoxy-carbonylpiperidinyl-4-acetic acid following substantially the same procedures as described for Preparative Example 14, Step A, to give 2.0 g of the product. Mass Spec.: MH$^+$=694 (FAB). partial $^1$H NMR (CDCl$_3$, 300 MHz): 8.38 (s, 1H); 7.60 (s, 1H); 7.25 (d, 1H); 7.05 (m, 1H); 1.45 (s, 9H).

Step B

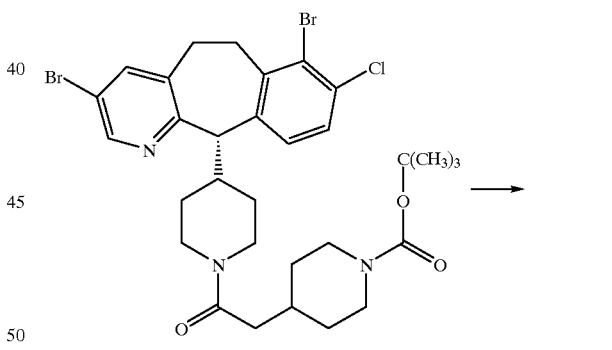

Treat 1.95 g of the product of Step A via substantially the same procedure as described for Preparative Example 17, Step B, to give 1.63 g of the product. Mass Spec. MH$^+$=594

(FAB). Partial ¹H NMR (CDCl₃, 300 MHz): 8.38 (s, 1H); 7.60 (s, 1H); 7.25 (d, 1H); 7.03 (m, 1H); 4.64 (d, 1H); 3.90 (m, 2H).

Step C

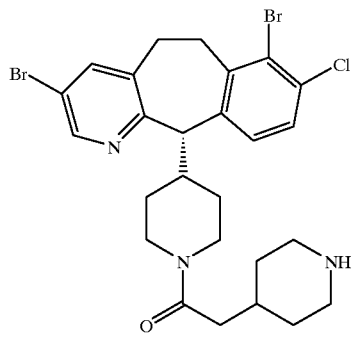

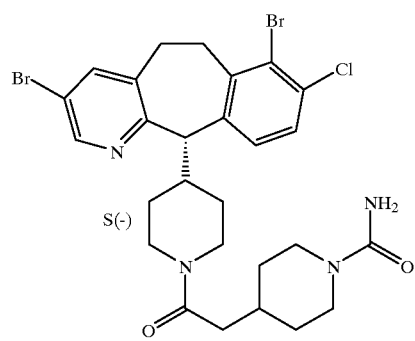

Treat 1.6 g of the product of Step B with 1.3 mL of (CH₃)₃SiNCO using substantially the same procedure as described for Preparative Example 14, Step C, to give 1.27 g of the title compound. Mass spec.: MH⁺=637 (FABS); $[\alpha]_D^{25}$=−33.1° (c=0.58, EtOH). partial ¹H NMR (CDCl₃, 400 MHz): 8.38 (s, 1H); 7.59 (s, 1H); 7.25 (d, 1H); 7.04 (m, 1H); 4.60 (d, 1H); 4.41 (s, 2H).

Preparative Examples 24A & 24B

Preparative Example 24A

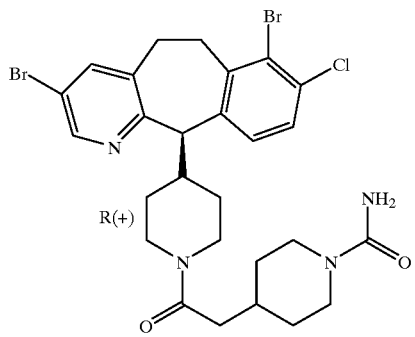

Preparative Example 24B

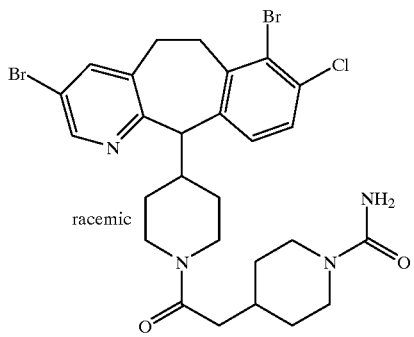

The (+)-enantiomer of the title compound from Preparative Example 10, Step B, (2.1 g) is converted to the title compound via substantially the same procedure as described for Preparative Example 21, Steps A–C, to give the title compound, Preparative Example 24A. Mass spec.: MH⁺=637 (FABS); $[\alpha]_D^{25}$=+32.4° (c=0.57, EtOH). Partial ¹H NMR (CDCl₃, 400 MHz): 8.39 (s, 1H); 7.59 (s, 1H); 7.25 (d, 1H); 7.04 (m, 1H); 4.60 (d, 1H); 4.41 (s, 2H). partial ¹H NMR (DMSO-d₆, 400 MHz): 8.42 (s, 1H); 7.88 (s, 1H); 7.41 (d, 1H); 7.29 (m, 1H); 5.85 (s, 2H); 4.20 (d, 1H).

The racemic title compound from Preparative Example 10, Step A, is converted to the racemic title compound, Preparative Example 24B, in an analogous manner. Partial ¹H NMR (CDCl₃, 400 MHz): 8.38 (s, 1H); 7.59 (s, 1H); 7.25 (d, 1H); 7.04 (m, 1H); 4.60 (d, 1H); 4.41 (s, 2H). partial ¹H NMR (DMSO-d₆, 400 MHz): 8.42 (s, 1H); 7.88 (s, 1H); 7.41 (d, 1H); 7.29 (d, 1H); 5.85 (s, 2H); 4.20 (d, 1H).

Preparative Example 25

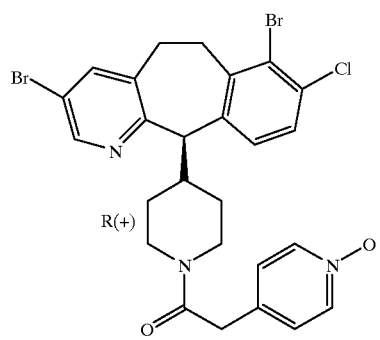

React 2.6 g of the (+)-enantiomer of the title compound of Preparative Example 10, Step B, and 1.68 g of the title compound of Preparative Example 1 following substantially the same procedure as described for Preparative Example 19 to give 2.10 g of the title compound. Mass spec.: MH⁺=604 (FAB); $[\alpha]_D^{25}$=+34.1° (10.98 mg/2 mL, EtOH). partial ¹H NMR (CDCl₃, 400 MHz): 8.38 (s, 1H); 8.15 (d, 2H); 7.58 (s, 1H); 7.26 (d, 1H); 7.15 (d, 2H); 7.03 (d, 1H); 4.57 (d, 1H).

To prepare the HCl salt of the title compound of Preparative Example 25 dissolve 700 mg of the title compound in 4 mL of CH₂Cl₂, add 4 mL of Et₂O, cool to 0° C. and slowly add (dropwise) 1 mL of HCl (g) in dioxane. Add 2 mL of Et₂O and stir at 0° C. for 7 min. Dilute with 30 mL of Et₂O, filter to collect the solid product and wash with 30 mL of Et₂O. Dry the solids in vacuo to give 0.836 g of the HCl salt of Example 14. [α]$_D$=+64.8° (9.94 mg/2 mL, EtOH).

Preparative Example 26A & 26B

Preparative Example 26A

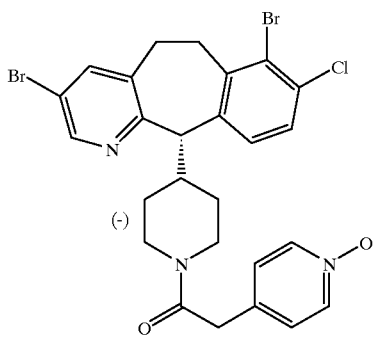
(-)

Preparative Example 26B

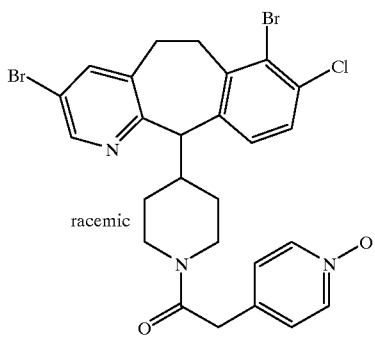
racemic

The (−)-enantiomer of the title compound of Preparative Example 10, Step B, (0.60 g) is reacted with 0.39 g of the title compound of Preparative Example 1, via substantially the same procedure as described for Preparative Example 19 to give 0.705 g of the title compound. Mass spec.: MH⁺=604 (FABS); [α]$_D^{25}$=−41.8° (EtOH). Partial ¹H NMR (CDCl₃, 300 MHz): 8.38 (s, 1H); 8.15 (d, 2H); 7.58 (s, 1H); 7.26 (d, 1H); 7.15 (d, 2H); 7.03 (d, 1H); 4.57 (d, 1H).

The HCl salt of the title compound of Preparative Example 26A is prepared via substantially the same procedure as described for Preparative Example 25. [α]$_D^{25}$=−63.2° (EtOH).

The racemic title compound of Preparative Example 10, Step A, is converted to the racemic title compound of Preparative Example 26B following substantially the same procedure as described for Preparative Example 19. Partial ¹H NMR (CDCl₃, 400 MHz): 8.38 (s, 1H); 8.15 (d, 2H); 7.58 (s, 1H); 7.26 (d, 1H); 7.15 (d, 2H); 7.03 (d, 1H); 4.57 (d, 1H). Partial ¹H NMR (DMSO-d₆, 400 MHz): 8.77 (d, 2H); 8.47 (s, 1H); 7.95 (s, 1H); 7.74 (d, 2H); 7.43 (m, 1H); 7.27 (d, 1H); 4.35 (d, 1H).

Preparative Example 27

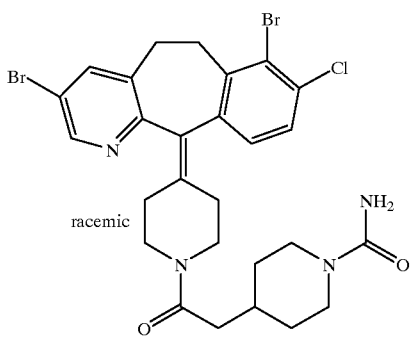
racemic

The title compound of Preparative Example 4 is reacted via substantially the same methods as described for Preparative Example 17, Steps A–C, to give the title compound, which is a racemate. Mass Spec.: MH⁺=635 (FAB). Partial ¹H NMR (CDCl₃): 8.45 (s, 1H); 7.60 (s, 1H); 7.35 (d, 1H); 7.05 (d, 1H); 4.45 (s, 1H).

Preparative Example 28

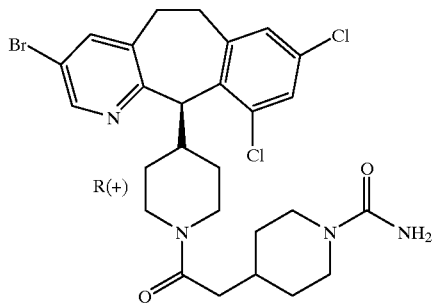
R(+)

Step A

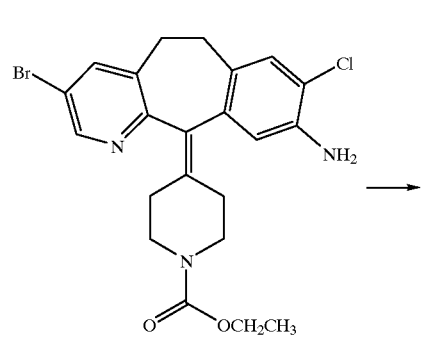

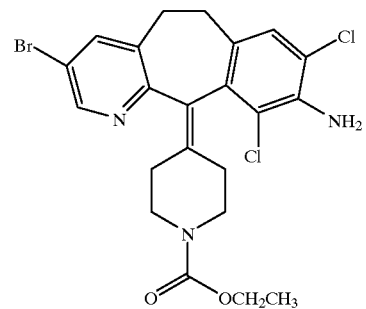

Dissolve 9.90 g (18.9 mmol) of the product of Preparative Example 7, Step B, in 150 mL CH₂Cl₂ and 200 mL of CH$_3$CN and heat to 60° C. Add 2.77 g (20.8 mmol) N-chlorosuccinimide and heat to reflux for 3 h., monitoring the reaction by TCL (30%EtOAc/H$_2$O). Add an additional 2.35 g (10.4 mmol) of N-chlorosuccinimide and reflux an additional 45 min. Cool the reaction mixture to room temperature and extract with 1N NaOH and CH$_2$Cl$_2$. Dry the CH$_2$Cl$_2$ layer over MgSO$_4$, filter and purify by flash chromatography (1200 mL normal phase silica gel, eluting with 30% EtOAc/H$_2$O) to obtain 6.24 g of the desired product. M.p. 193–195.4° C. MH$^+$=510.

Step B

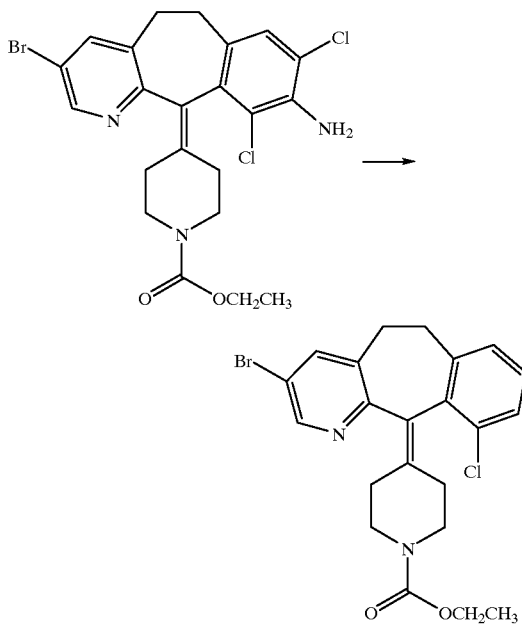

To 160 mL of conc. HCl at −10° C. add 2.07 g (30.1 mmol) NaNO$_2$ and stir for 10 min. Add 5.18 g (10.1 mmol) of the product of Step A and warm the reaction mixture from −10° C. to 0° C. for 2 h. Cool the reaction to −10° C., add 100 mL H$_3$PO$_2$ and let stand overnight. To extract the reaction mixture, pour over crushed ice and basify with 50% NaOH/ CH$_2$Cl$_2$. Dry the organic layer over MgSO$_4$, filter and concentrate to dryness. Purify by flash chromatography (600 mL normal phase silica gel, eluting with 20% EtOAc/ hexane) to obtain 3.98 g of product. Mass spec.: MH$^+$=495.

Step C

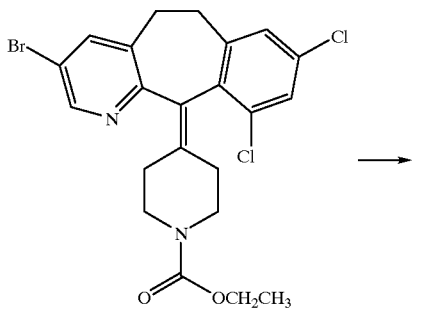

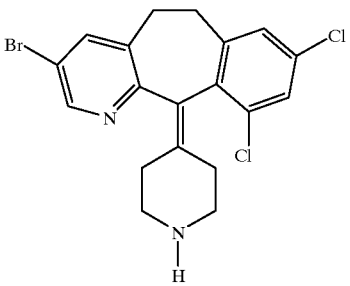

Dissolve 3.9 g of the product of Step B in 100 mL conc. HCl and reflux overnight. Cool the mixture, basify with 50% w/w NaOH and extract the resultant mixture with CH$_2$Cl$_2$. Dry the CH$_2$Cl$_2$ layer over MgSO$_4$, evaporate the solvent and dry under vacuum to obtain 3.09 g of the desired product. Mass spec.: MH$^+$=423.

Step D

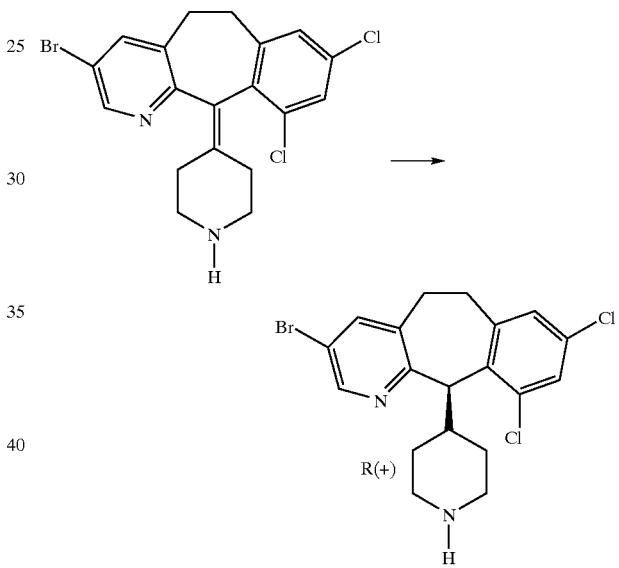

Using a procedure similar to that described in Preparative Example 8, obtain 1.73 g of the desired product, m.p. 169.6–170.1° C.; $[\alpha]_D^{25}$=+48.2° (c=1, MeOH). MH+=425.

Step E

Use a procedure similar to that of Preparative Example 14 with the product of Step D as the starting material to obtain the title compound. M.p. 152.3–153.3° C.; $[\alpha]_D^{25}$=+53.0° (c=1, MeOH). MH$^+$=593.

Preparative Example 29

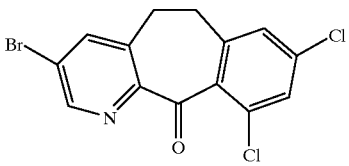

Step A

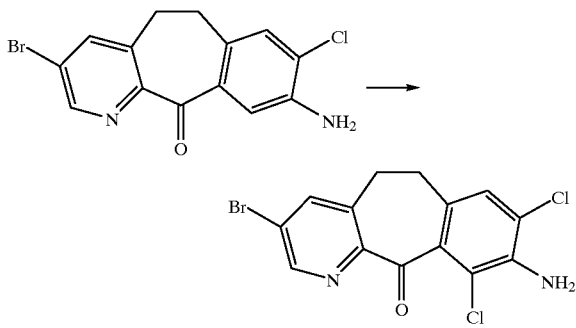

Treat 15.0 g (44.4 mmol) of the product of Preparative Example 9, Step B, with 6.52 g (48.9 mmol) of N-chlorosuccinimide in a manner similar to that described in Preparative Example 28 Step A and extract as described to obtain 16.56 g of the desired product, m.p. 234.7–235.0° C. MH$^+$=370.

Step B

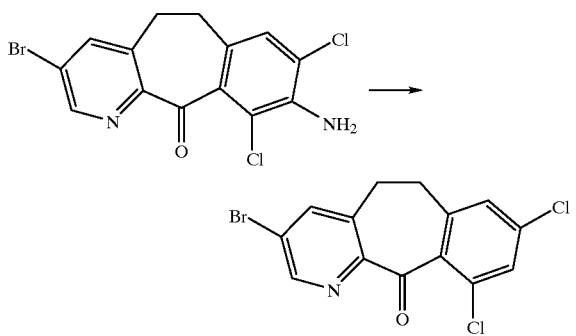

Treat 16.95 g (45.6 mmol) of the product of Step A in the manner described in Preparative Example 28, Step B, to obtain 13.07 g of the desired product, m.p. 191.7–192.1°C. MH$^+$=356.

Preparative Example 30

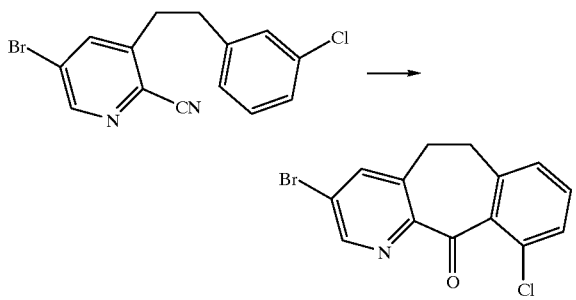

Heat 200 mg of the cyano starting material in 17 g polyphosphoric acid at 190–200° C. for 45 min. Pour the resultant mixture into ice, add 30% HCl and stir for 30 min. Extract with CH$_2$Cl$_2$, wash with brine, dry over Na$_2$SO$_4$, filter and concentrate. Purify by preparative TLC, eluting with EtOAc/hexane to obtain 21 mg of the desired product (also obtained 59 mg of the 10-chloro product).

Preparative Example 31

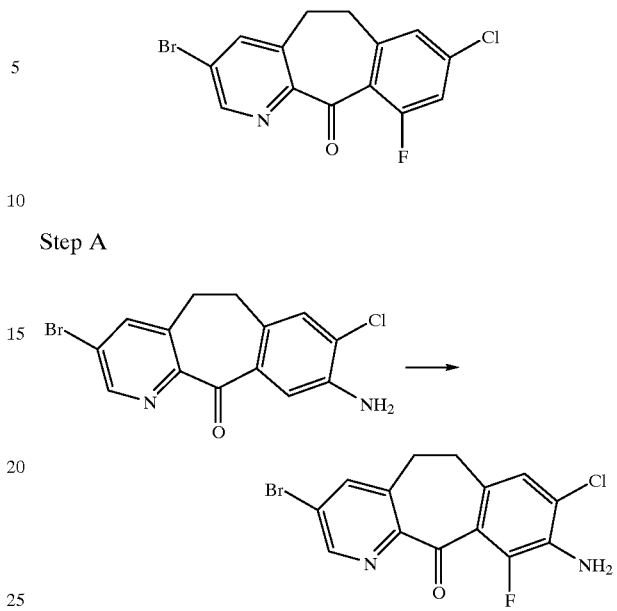

Step A

Dissolve 10.0 g (29.6mmol) of the product of Preparative Example 9, Step B, in 150 mL CH$_2$Cl$_2$ and 200 mL CH$_3$CN at room temperature. Heat the mixture to 60° C., add 10.45 g (32.6 mmol) of 1-fluoro-4-hydroxy-1,4-diazoniabicyclo[2,2,2]octane bis-(tetrafluoroborate) and heat to reflux for 4 h. Cool the mixture to room temperature, extract with CH$_2$Cl$_2$ and 1 N NaOH. Dry the CH$_2$Cl$_2$ layer over MgSO$_4$, filter and concentrate to dryness. Purify the resultant residue by flash chromatography using 1400 mL normal phase silica gel eluted with 10% EtOAc-CH$_2$Cl$_2$+2 drops NH$_4$OH to obtain 2.00 g of product, m.p. 103.2–103.5° C. MH$^+$=355.

Step B

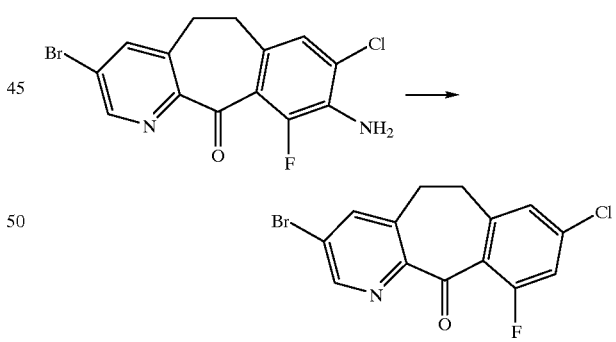

Using a procedure substantially as described in Preparative Example 9, Step D, treat 1.80 g (5.1 mmol) of the product of Step A. Purify the crude product by flash chromatography using 200 mL normal phase silica gel eluted with 20% EtOAc/hexane. Mass spec.: MH$^+$=339.

Preparative Example 32

Using appropriate starting materials and procedures as described above, the following compounds could be made:

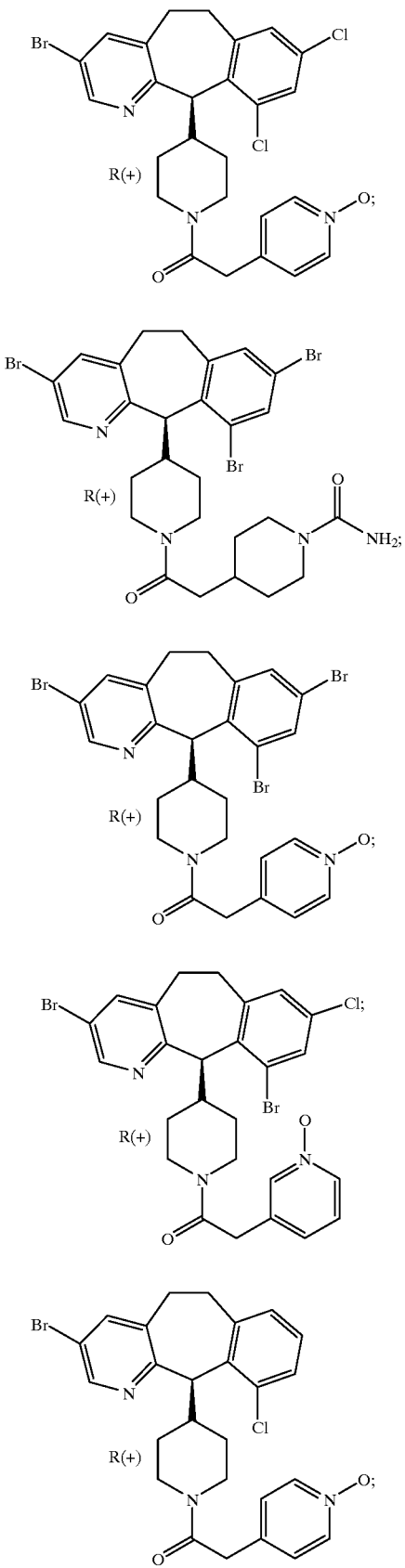
-continued
Preparative Example 33
Step A
3-Bromo-8-chloro-5,6-dihydro-11H-benzo [5,6]cyclohepta[1,2-b]pyridin-11-one N1-oxide
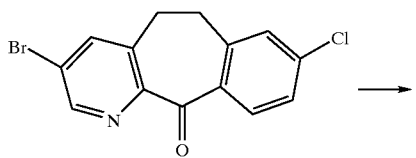

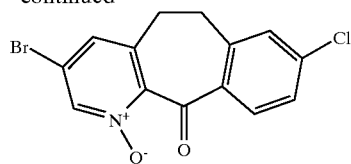

To a solution of 3-bromo-8-chloro-5,6-dihydro-11H-benzo[5,6]cyclohepta[1,2-b]pyridin-11-one (2 g) (6.2 mmoles) in anhydrous dichloromethane (14 ml) at 0° C. and under an argon atmosphere, was added a solution of 3-chloroperbenzoic acid (1.76 g) (10.4 mmoles) in anhydrous dichloromethane (35 ml) dropwise over a period of 30 minutes. The mixture was allowed to warm to room temperature and after 18 h additional 3-chloroperbenzoic acid (0.88 g) (5.2 mmoles) in anhydrous dichloromethane (25 ml) was added and the mixture was stirred for a total of 42 h. The mixture was diluted with dichloromethane and washed with 1N NaOH (200 ml). The aqueous layer was extracted with additional dichloromethane (2X200 ml) and the combined organic layers were dried over magnesium sulfate, filtered and evaporated to dryness. The product was chromatographed on silica gel using 0.25%–0.5%–1% (10% conc. NH$_4$OH in methanol)dichloromethane as the eluant to give the title compound (Yield:1.386 g, 66%): ESIMS; m/z 338.1 (MH$^+$); δ$_c$ (CDCl$_3$) CH$_2$: 30.5, 34.0; CH: 126.9, 127.6, 130.3, 132.5, 140.4; C: 121.0, 135.1, 138.3, 139.7, 141.6, 145.3, 188.0 ppm.

Step B
3-Bromo-8-chloro-6,11-dihydro-11-hydroxy-5H-benzo[5,6]cyclohepta[1,2-b]pyridine N1-oxide

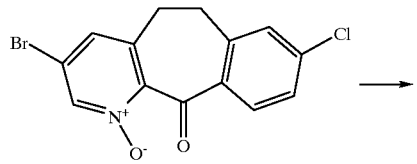

The title compound of Preparative Example 33A (1.3422 g) (3.96 mmoles) was dissolved in methanol (18 ml) and dichloromethane (20 ml) and sodium borohydride (0.219 g) (5.79 mmoles) was added. The mixture was stirred under argon at 0° C. for 1 h and then allowed to warm up to 25° C. over a period of 1 h. The mixture was diluted with dichloromethane (800 ml) and washed with 1N NaOH (150 ml). The aqueous layer was extracted with dichloromethane (2×100 ml) and the combined organic layers were dried over magnesium sulfate, filtered and evaporated to dryness. The product was chromatographed on silica gel using 1% (10% conc. NH$_4$OH in methanol)dichloromethane as the eluant to give the title compound (Yield: 1.24 g, 92%): ESIMS: m/z 340.1 (MH$^+$); δ$_c$ (CDCl$_3$) CH$_2$: 31.2, 32.0; CH: 69.1, 126.8, 129.5, 131.7, 131.7, 136.7; C: 118.3, 134.7, 135.2, 139.7, 141.0, 148.9 ppm.

Step C
3-Bromo-8,11-dichloro-6,11-dihydro-5H-benzo[5,6]cyclohepta[1,2-b]pyridine N1-oxide

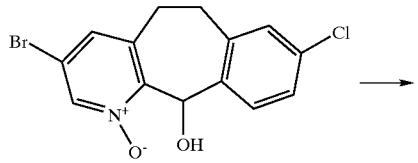

The title compound of Preparative Example 33B (1.19 g) (3.49 mmoles) was dissolved in anhydrous toluene (22.5 ml) and the solution was cooled to 0° C. under argon. Thionyl chloride (0.472 ml) (6.46 mmoles) in anhydrous toluene (5 ml) was added and the mixture was stirred at 0° C. for 1 h. The mixture was allowed to warm to 25° C. over a period of 2.5 h. The solution was poured into a 20% solution of ethyl acetate in dichloromethane (800 ml) and the mixture was washed with 1N NaOH. The aqueous layer was extracted with dichloromethane (2×200 ml) and the combined organic layers were dried over magnesium sulfate, filtered and evaporated to give the product which was used without further purification.

Step D
3-Bromo-8-chloro-6,11-dihydro-11-(1-piperazinyl)-5H-benzo[5,6]cyclohepta[1,2-b]pyridine N1-oxide

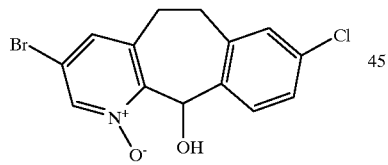

The title compound from Preparative Example 33C (3.49 mmoles) was dissolved in anhydrous THF (10 ml) and a solution of piperazine (1.505 g) (17.47 mmoles) in anhydrous THF (20 ml) was added and the mixture was stirred under argon at 25° C. for 69 h. The mixture was poured into dichloromethane (800 ml) and washed with 1N NaOH (125 ml). The aqueous layer was extracted with dichloromethane (2×200 ml) and the combined organic layers were dried over magnesium sulfate, filtered and evaporated to dryness. The product was chromatographed on silica gel using 5% (10% conc. NH$_4$OH in methanol)dichloromethane as the eluant to give the title compound (Yield: 1.2772 g, 89%): FABMS: m/z 408 (MH$^+$); δ$_c$ (CDCl$_3$) CH$_2$: 30.1, 30.4, 46.2, 46.2, 52.3, 52.3; CH: 64.6, 126.3, 130.3, 130.6, 133.6, 138.5; C: 118.0, 133.9, 134.5, 139.8, 140.8, 148.8 ppm.

Step E (+) 3-Bromo-8-chloro-6,11-dihydro-11R-(1-piperazinyl)-5H-benzo[5,6]cyclohepta[1,2-b]pyridine N1-oxide and (-)3-Bromo-8-chloro-6,11-dihydro-11S-(1-piperazinyl-5H-benzo[5,6]cyclohepta[1,2-b]pyridine N1-oxide

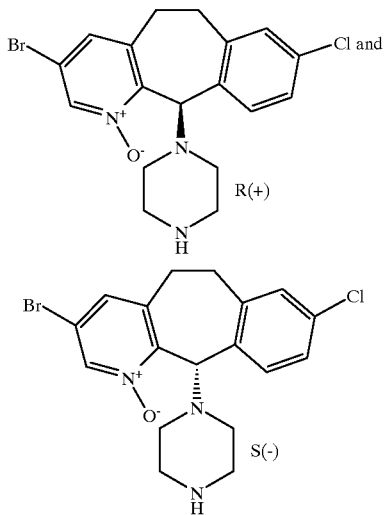

The title racemic compound from Step D above (1 g) was separated on a Chiralpak AD HPLC column (5 cm ID and 50 cm long; particle size 20μ) using 2-propanol:hexane:diethylamine:30:70:02 stepped up to 40:60;0.2 after passage of 2L, as the eluant to give the R(+) enantiomer as the first eluting fraction (0.486 g): FABMS: m/z 408 (MH+), δ$_c$ (CDCl$_3$) CH$_2$: 30.1, 30.4, 46.3, 46.3, 52.5, 52.5; CH: 64.7, 126.2, 130.4, 130.6, 133.6, 138.5; C: 118.0, 133.9, 134.4, 139.8, 140.8, 148.9; [α]$_D^{23°\ C.}$ +90.9° (10.34 mg/2 mL, MeOH), followed by the S(-) enantiomer as the second eluting fraction (0.460 g): FABMS: m/z 408.1 (MH+), δ$_c$ (CDCl$_3$) CH$_2$: 30.1, 30.4, 46.2, 46.2, 52.4, 52.4; CH: 64.6, 126.3, 130.4, 130.6, 133.6, 138.5; C: 118.1, 133.9, 134.4, 139.8, 140.8, 148.8; [α]$_D^{23°\ C.}$ -85.9° (8.61 mg/2 mL, MeOH).

EXAMPLE 1

1-(3-Bromo-8-chloro-6,11-dihydro-5H-benzo[5,6]cyclohepta[1,2-b]pyridin-11-yl)-4-(4-pyridinylacetyl)piperazine N1, N4-dioxide

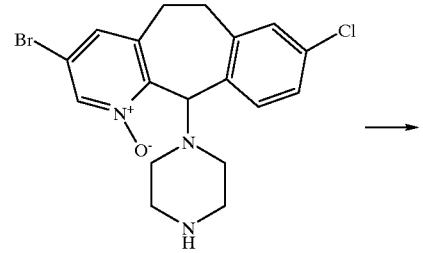

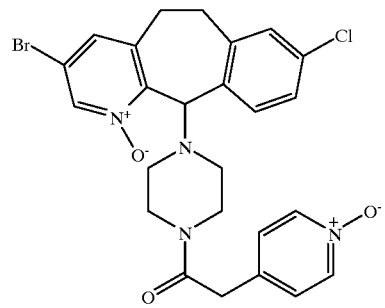

The title compound from Preparative Example 33D (0.4 g) (0.979 mmoles), 4-pyridylacetic acid N1-oxide (0.1948 g) (1.27 mmoles), 1-(3-dimethylaminopropyl)-3-ethylcarbodiimide hydrochloride (0.244 g) (1.27 mmoles), 1-hydroxybenzotriazole (0.172 g) (1.27 mmoles) and 4-methylmorpholine (0.14 ml) (1.27 mmoles) were dissolved in anhydrous DMF (15 ml) and the mixture was stirred at 25° C. for 18 h. The solution was poured into dichloromethane (800 ml) and washed with 1N NaOH. The aqueous layer was extracted with dichloromethane (2×200 ml) and the combined organic layers were evaporated to dryness. The residue was chromatographed on silica gel using 3.5% (10% conc. NH$_4$OH in methanol) dichloromethane as the eluant to give the title compound (Yield: 0.4806 g, 90%): LSIMS: m/z 543 (MH+); δ$_c$(CDCl$_3$) CH$_2$: 30.1, 30.5, 38.4, 42.1, 45.9, 50.4, 50.6; CH: 63.8, 126.5, 126.8, 126.8, 130.4, 130.5, 133.4, 138.4, 139.0, 139.0; C: 118.4, 133.4, 133.9, 134.8, 139.8, 141.0, 148.8, 167.0 ppm. PMR data: δ$_H$ (CDCl$_3$): 5.78 (s,1H,H$_{11}$), 7.14 (d,2H,Ar—H), 7.15 (s,2H,Ar—H), 7.20 (d,1H,Ar—H), 7.22 (d,1H,Ar—H), 8.16 (d,2H,Ar-H), 8.29 (s,1H,Ar—H).

EXAMPLE 2

(+)-4-[2-[4-(3,10-Dibromo-8-chloro-6,11-dihydro-5H-benzo[5,6]cyclohepta[1,2-b]pyridin-11(R)-YL)-1-piperidinyl]-2-oxoethyl]-1-piperidinecarboxamide N-oxide

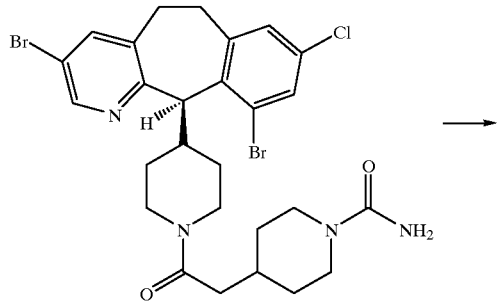

To a dichloromethane solution (50 mL) of the product of Preparative Example 21, Step C, (1.06 g, 1.65 mmol) was added meta-chloroperoxybenzoic acid (0.5 g of 57–86% purity, 1 eq). After stirring at room temperature for 5 hours, an additional 0.23 g of meta-chloroperoxybenzoic acid was added and the resulting mixture was stirred at room temperature overnight. The reaction mixture was washed with a saturated aqueous solution of sodium bicarbonate, dried over anhydrous magnesium sulfate, filtered and concentrated in vacuo to afford a light yellow foam. Purification by flash column chromatography (silica gel) using 5% methanol-dichloromethane saturated with ammonium hydroxide provided the title compound (0.60 g, 56% yield, mp 170.5–175° C.). $[\alpha]_D^{21°\ C.} = +116.20$ (c =0.113, methanol).

EXAMPLE 3

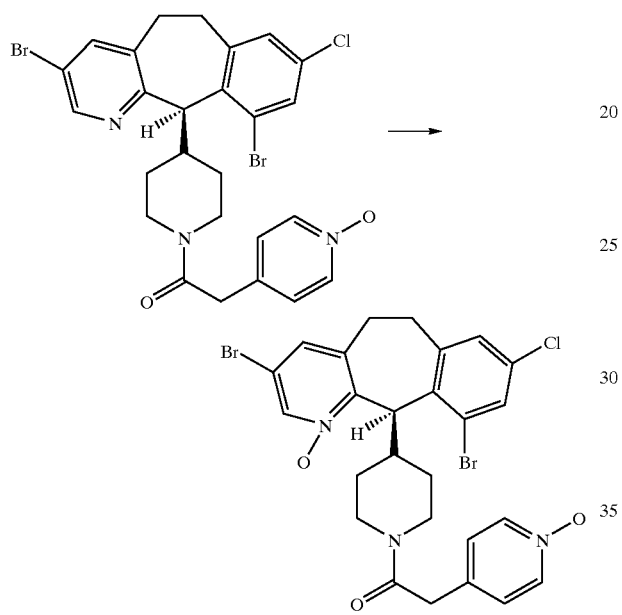

Following the procedure of Example 2, with the exception that the product of Preparative Example 19 was used instead of the product of Preparative Example 21, Step C, gave the product as a white solid, mp =174.2° C.

EXAMPLE 4
(−)-4-(8-Chloro-3,7Dibromo-6,11dihydro-5H-benzo[5,6]cyclohepta [1,2-b]Pyridin-11-yl)-1-(4-Pyridinylacetyl)piperidineN1-Oxide N4-Oxide

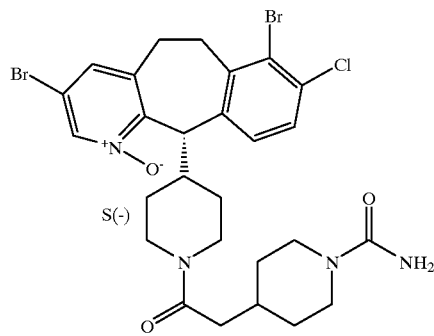

Added m-Chloroperbenzoic acid (50% 1.5 g,4.36 mmol) to a solution of the product from Preparative Example 23, Step C, (1.0 g,1.48 mmol) in methylene chloride (15 ml) at 0° C., then stirred at 0° C. for 5 hours, and room temperature for 3 hours. Water (50 ml), ammonium hydroxide (10 ml, conc) were added, and the mixture was extracted with methylene chloride (2×200 ml). The organic layer was separated, dried over magnesium sulfate, filtered, and solvent evaporated yielding a solid, which chromatographed on silica gel eluting with 10% v/v methanol: methylene chloride containing 2% ammonium hydroxide yielding the title product as a white solid (700 mg, 70%)$[\alpha]_D^{24.°\ C.} = -68.9°$ (c=0.352, ethanol).

MS (FAB, MH,653) HRMS Calc(C27H32N4O3BrCl(81)Br) 655.0509 Measured 655.0518

1H NMR(CDCL3) δ 8 8.31(s,1H), 7.28(s,1H), 7.19(d, 1H), 7.11(d, 1H), 5.37(m,1H), 4.60(d,1H), 4.42(s,2H), 3.86 (m,3H), 3.41(m,3H), 2.89(m,4H), 2.42(m,1H), 2.20(m,3H), 2.04(m,1H), 1.78(m,2H), 1.66(m,1H), 1.48(m,2H), 1.16(m, 3H).

EXAMPLE 5
(−)-4-(8-Chloro-3,7-Dibromo-6,11-Dihydro-5H-Benzo[5,6]Cyclohepta [1,2-b]Pyridin-11-yl)-1-(4-Pyridinylacetyl)Piperidine N1-Oxide, N4-Oxide

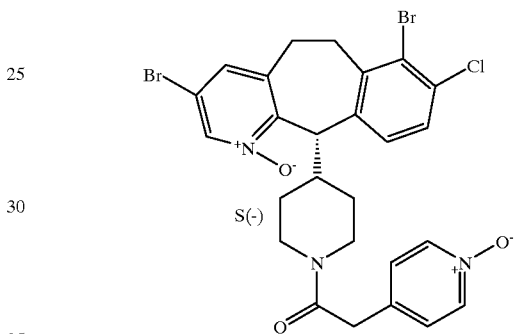

Following the same procedure as in Example 4, with the exception that an equivalent quantity of the product of Preparative Example 26A is used instead of the product from Preparative Example 23, Step C,. the title product was obtained as a white solid (73% yield). $[\alpha]_D^{24.°\ C.} = -76.6°$ (c=0.197, ethanol).

MS (FAB, MH 620) HRMS Calc MH C26H25N3O3BrCl (81)Br (621.9931) Measured 621.9942.

1H NMR(CDCL3)δ 8.32(s,1H), 8.22(d,2H), 7.29(s,1H), 7.19(d,1H), 7.18(d,2H), 7.10(d,1H), 5.37(m,1H), 4.58(d, 1H), ,3.78(d,1H), 3.66(d,2H), 3.41(s,2H), 3.38(m,1H), 2.95 (m,3H), 2.50(m,1H), 2.28(m,1H), 1.63(m,1H), 1.45(m,2H).

EXAMPLE 6
4-(3-Bromo-8-Chloro-11H-Benzo[5.6]Cyclohepta[1,2-b]Pyridi-11-yl) -1-(4-Pyridinylacetyl)Piperidine N1-Oxide, N4-Oxide

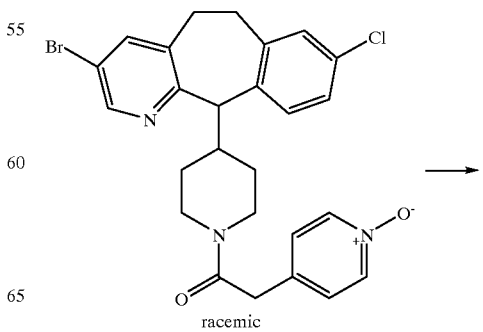

racemic

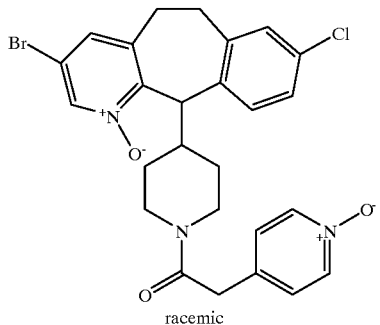

racemic

Following the procedure of Preparative Example 12, except that the product of Preparative Example 3, Step D, is used instead of the compound of Preparative Example 4, the starting reactant is obtained. Following the procedure of Example 4, with the exception that the above reactant was used instead of the product from Preparative Example 23, Step C, yielded the title compound as a white solid (100%).

MS (FAB,MH 540) HRMS Calc MH C26H24N3O3BrCl (540.0690), Measured (540.0691)

1H NMR(CDCL3)δ 8.45(s,1H), 8.14(d,2H), 7.26–7.34 (m,3H), 7.11(d,2H), 7.03,d1H), 6.73(d,1H), 5.55(d,1H), 4.40(m,1H), 3.70(m,2H), 3.59(s,2H), 2.85(m,1H), 2.45(m, 1H), 2.15(m,1H), 1.35(m,1H), 1.15(m,3H).

EXAMPLE 7

(+) 1-(3-Bromo-8-chloro-6,11-dihydro-5H-benzo[5,6]cyclohepta [1,2-b]pyridin-11R-yl)-4-(4-pyridinylacetyl)piperazine N1-oxide

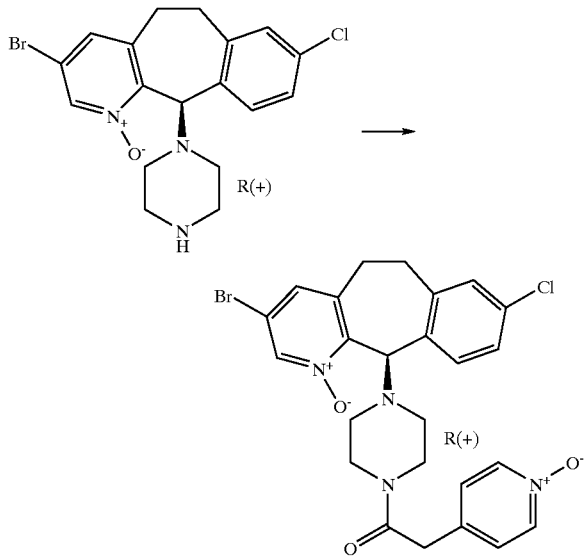

The title compound from Preparative Example 33, Step E, R(+) enantiomer (360.4 mg, 0.882 mmoles), 4-pyridylacetic acid N1-oxide (175.5 mg, 1.146 mmoles), 1-(3-dimethylaminopropyl)-3-ethylcarbodiimide hydrochloride (220 mg, 1.146 mmoles), 1-hydroxybenzotriazole (155 mg, 1.146 mmoles) and 4-methylmorpholine (0.126 mL, 1.146 mmoles) were dissolved in anhydrous DMF 11 mL) and the mixture was stirred at 25° C. for 18 h. The reaction was worked up as described in Example 1 and the product was chromatographed on silica gel using 4% (10% conc. NH$_4$OH in methanol)dichloromethane as the eluant to give the title compound (Yield: 441.1 mg, 92%): LCMS: m/z 543.1 (MH$^+$); δ$_c$ (CDCl$_3$) CH$_2$: 30.1, 30.6, 38.5, 42.1, 46.0, 50.5, 50.9; CH: 63.9, 126.5, 126.9, 126.9, 130.5, 130.6, 133.5, 138.5, 139.0, 139.0,: C: 118.4, 134.0, 134.0, 134.9, 139.9, 141.0, 147.8, 167.1; δ$_H$ (CDCl$_3$): 5.74 (s,1H,H$_{11}$), 7.12 (d,2H,Ar—H), 7.13 (s,2H,Ar—H), 7.19 (d,1H,Ar—H), 7.21 (d,1H,Ar—H), 8.14 (d,2H,Ar—H), 8.27 (s,1H,Ar—H); $[\alpha]_D^{23°\ C.}$ +69.2° (10 mg/2 mL, MeOH).

EXAMPLE 8

(−) 1-(3Bromo-8-chloro-6,11-dihydro-5H-benzo[5,6]cyclohepta [1,2-b]pyridin-11S-yl)-4-(4-pyridinylacetyl)piperazine N1-oxide

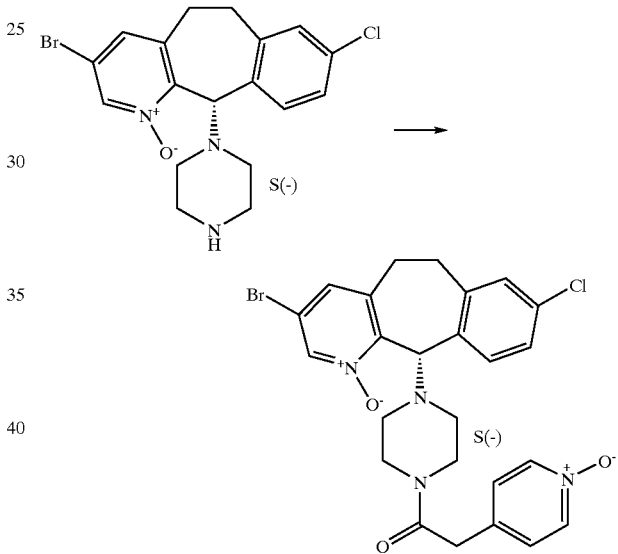

The title compound from Preparative Example 33, Step E, S(−) enantiomer (374.8 mg, 0.917 mmoles), 4-pyridylacetic acid N1-oxide (182.6 mg, 1.192 mmoles), 1-(3-dimethylaminopropyl)3-ethylcarbodiimide hydrochloride (229 mg, 1.192 mmoles), 1-hydroxybenzotriazole (161 mg, 1.192 mmoles) and 4-methylmorpholine (0.131 mL, 1.192 mmoles) were dissolved in anhydrous DMF (11 mL) and the mixture was stirred at 25° C. for 18 h. The reaction was worked up as described in Example 1 and the product was chromatographed on silica gel using 4% (10% conc. NH$_4$OH in methanol)dichloromethane as the eluant to give the title compound (Yield: 467.3 mg, 94%): LCMS: m/z 543.1 (MH$^+$); δ$_c$ (CDCl$_3$) CH$_2$: 30.0, 30.5, 38.4, 42.0, 45.9, 50.4, 50.8; CH: 63.8, 126.5, 126.8, 126.8, 130.4, 130.6, 133.4, 138.4, 138.9, 138.9,: C: 118.4, 134.0, 134.0, 134.8, 139.8, 140.9, 147.7, 167.0; δ$_H$ (CDCl$_3$): 5.76 (s,1H,H$_{11}$), 7.13 (d,2H,Ar—H), 7.15 (s,2H,Ar—H), 7.21 (d,1H,Ar—H), 7.23 (d,1H,Ar—H), 8.16 (d,2H,Ar—H), 8.29 (s,1H,Ar—H); $[\alpha]_D^{23.4°\ C.}$ −65.5° (10.4 mg/2 mL, MeOH).

EXAMPLE 9

(±) 4-[2-[(3-Bromo-8-chloro-6,11-dihydro-5H-benzo[5,6]cyclohepta [1,2-b]pyridin-11-yl)-1-piperazinyl]-2-oxoethyl]-1-piperidinecarboxamide N1-oxide

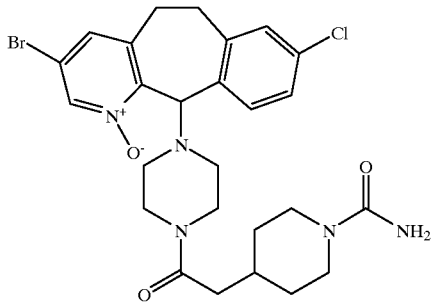

Step A (±) 1,1-Dimethylethyl 4-[[[4-(3-bromo-8-chloro-6,11-dihydro-5H-benzo[5,6]cyclohepta[1,2-b]pyridin-11-yl)-1-piperazinyl]-1-carbonyl]methyl]-1-piperdinecarboxylate N1-oxide

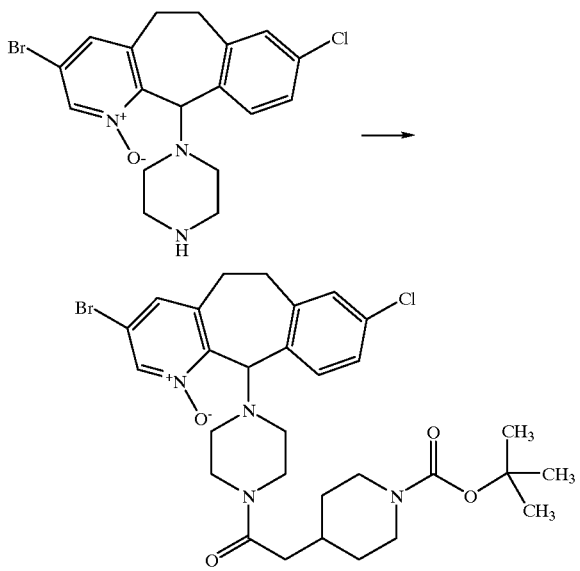

The title compound from Preparative Example 33, Step D, (±) (789.1 mg, 1.93 mmoles), 1-tert-butoxycarbonyl-4-piperidinylacetic acid (610.6 mg, 2.51 mmoles), 1-(3-dimethylaminopropyl) -3-ethylcarbodiimide hydrochloride (481.2 mg, 2.51 mmoles), 1-hydroxybenzotriazole (339.2 mg, 2.51 mmoles) and 4-methylmorpholine (0.276 mL, 2.51 mmoles) were dissolved in anhydrous DMF (30 mL) and the mixture was stirred at 25° C. for 21 h. The reaction was worked up as described in Example 1 and the product was chromatographed on silica gel using 0.5%–1% (10% conc. NH$_4$OH in methanol)dichloromethane as the eluant to give the title compound (Yield: 1.22 g, 100%): FABMS: m/z 633.3 (MH$^+$); δ$_c$ (CDCl$_3$) CH$_3$: 28.5, 28.5, 28.5; CH$_2$: 30.2, 30.5, 32.2, 32.2, 39.5, 41.7, 43.8, 43.8, 45.8, 50.8, 51.2; CH: 33.3, 64.0, 126.5, 130.6, 130.6, 133.5, 138.5; C: 79.3, 118.3, 133.6, 134.8, 139.9, 140.9, 148.1, 154.8, 170.0; δ$_H$ (CDCl$_3$): 1.46 (s,9H,—CMe$_3$), 5.75 (s,1H,H$_{11}$), 7.13 (d,1H,Ar—H), 7.16 (s,1H,Ar—H), 7.19 (s,1H,Ar—H), 7.23 (d,1H,Ar—H), 8.29 (s,1H,Ar—H).

Step B (±) 1-(3-Bromo-8-chloro-6,11dihydro-5H-benzo[5,6]cyclohepta [1,2-b]pyridin-11-yl)-4-(4-piperidinylacetyl)piperazine N1-oxide

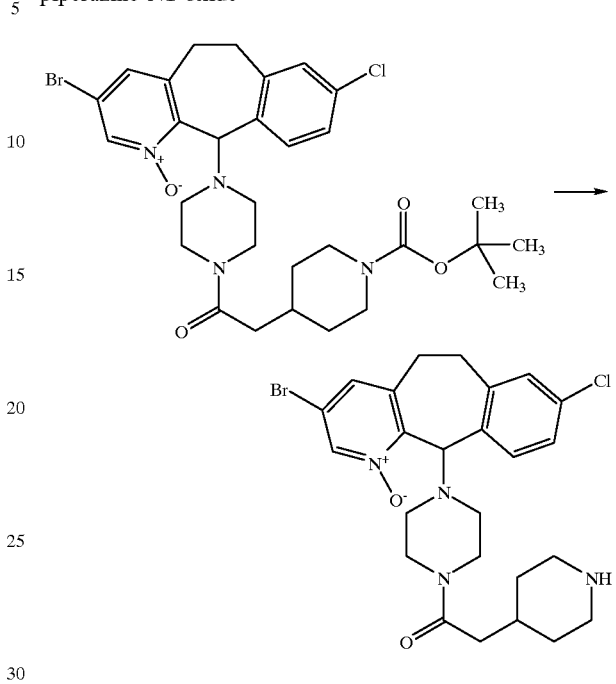

The title compound from Step A above (1.21 g, 1.91 mmoles) was dissolved in methanol (10.6 mL) and 10% (v/v) conc. H$_2$SO$_4$ in dioxane (26 mL) and the mixture was stirred under argon at 25° C. for 1.5 h. The solution was concentrated and diluted with CH$_2$Cl$_2$ and basified with 1N aqueous NaOH. The CH$_2$Cl$_2$ extract, containing only part of the product due to its water solubility, was dried (MgSO$_4$), filtered and evaporated to dryness. The product was chromatographed on silica gel using 10% (10% conc NH$_4$OH in MeOH)dichloromethane as the eluant to give the title compound (Yield: 87.7 mg, 10%): FABMS: m/z 533.1 (MH$^+$), δ$_c$ (CDCl$_3$): CH$_2$: 30.2, 30.4, 32.4, 32.4, 39.6, 41.6, 45.7, 45.9, 45.9, 50.7, 51.2; CH: 32.7, 64.0, 126.5, 130.6, 130.6, 133.5, 138.5; C: 118.3, 133.5, 134.7, 139.9, 140.9, 148.1, 169.8; δ$_H$ (CDCl$_3$): 5.73 (s,1H,H$_{11}$), 7.12 (d,1H,Ar—H), 7.15 (s,1H, Ar—H), 7.18 (s,1H,Ar—H), 7.21 (d,1H,Ar—H), 8.28 (s,1H, Ar—H).

Step C (±) 4-[2-[(3-Bromo-8-chloro-6,11-dihydro-5H-benzo[5,6]cyclo-hepta [1,2-b]pyridin-11-yl)-1-piperazinyl]-2-oxoethyl]-1-piperidinecarboxamide N1-oxide

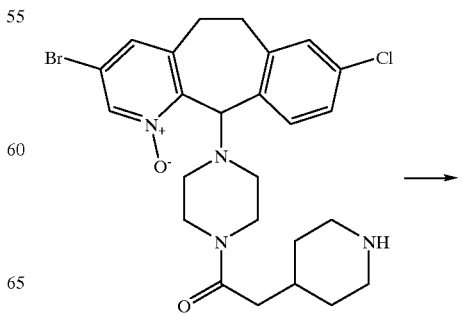

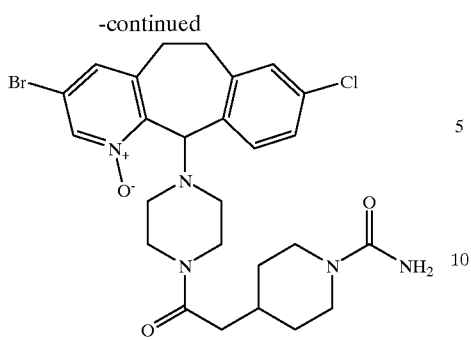
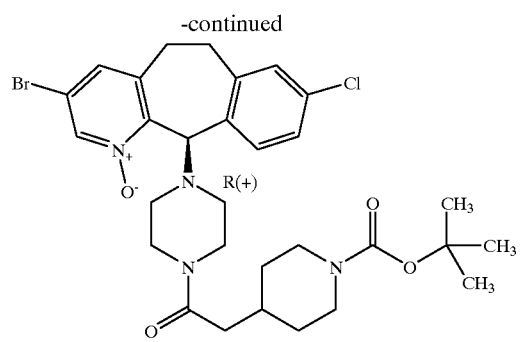

The title compound from Step B above (99.1 mg, 0.189 mmoles) and trimethylsilyl isocyanate (0.384 mL, 2.83 mmoles) were dissolved in anhydrous dichloromethane (3 mL) and the mixture was stirred at 25° C. under argon for 20 h. Additional trimethylsilyl isocyanate (0.0768 mL, 0.567 mmoles) was added and the reaction was allowed to proceed for an additional 5h. The mixture was diluted with dichloromethane and washed with saturated aqueous $NaHCO_3$, dried ($MgSO_4$), filtered and evaporated to dryness. The product was chromatographed on silica gel using 3.5% (10% conc. $NH_4OH$ in methanol)dichloromethane as the eluant to give the title compound (Yield: 80.4 mg, 81%): FABMS: m/z 576.1 ($MH^+$); $\delta_c$ ($CDCl_3$): $CH_2$: 30.1, 30.4, 32.0, 32.0, 39.2, 41.6, 44.4, 44.3, 45.7, 50.7, 51.1; CH: 32.9, 63.9, 126.4, 130.5, 130.6, 133.4, 138.4; C: 118.3, 133.5, 134.7, 139.8, 140.9, 148.0, 169.7; $\delta_H$ ($CDCl_3$): 5.74 (s,1H,$H_{11}$), 7.12 (d,1H,Ar—H), 7.15 (s,1H,Ar—H), 7.19 (s,1H,Ar—H), 7.22 (d,1H,Ar—H), 8.28 (s,1H,Ar—H).

EXAMPLE 10
(+) 4-[2-[(3-Bromo-8-chloro-6,11-dihydro-5H-benzo[5,6]cyclo-hepta [1,2-b]pyridin-11R-yl)-1-piperazinyl]-2-oxoethyl]-1-piperidinecarboxamide N1-oxide

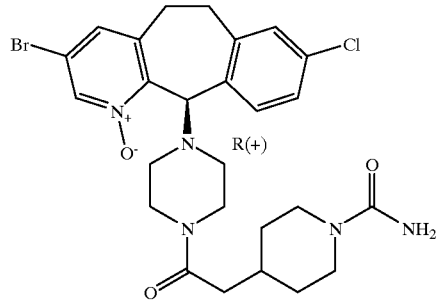

Step A
(+) 1,1-Dimethylethyl 4-[[[4-(3-bromo-8-chloro-6,11-dihydro -5H-benzo[5,6]cyclohepta[1,2-b]pyridin-11R-yl)-1-piperazinyl]-1-carbonyl]methyl]-1-piperidinecarboxylate N1-oxide

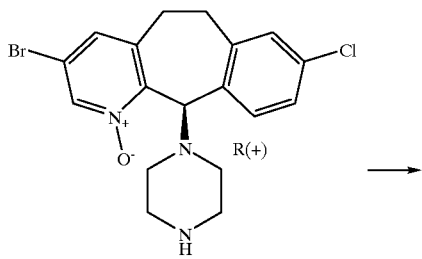

The title compound from Preparative Example 33, Step E, R(+) enantiomer (1 g, 2.45 mmoles), 1-tert-butoxycarbonyl-4-piperidinylacetic acid (487 mg, 3.181 mmoles), 1-(3-dimethylaminopropyl) -3-ethylcarbodiimide hydrochloride (610 mg, 3.181 mmoles), 1-hydroxybenzotriazole (430 mg, 3.181 mmoles) and 4-methylmorpholine (0.35 mL, 3.181 mmoles) were dissolved in anhydrous DMF (30.5 mL) and the mixture was stirred at 25° C. for 66 h. The reaction was worked up as described in Example 1 and the product was chromatographed on silica gel using 1% (10% conc. $NH_4OH$ in methanol)dichloromethane as the eluant to give the title compound (Yield: 1.25 g, 81%): LCMS: m/z 633.1 ($MH^+$); $\delta_c$ ($CDCl_3$) $CH_3$: 28.5, 28.5, 28.5; $CH_2$: 30.2, 30.5, 32.2, 32.2, 39.4, 41.7, 43.6, 43.6, 45.8, 50.7, 51.2; CH: 33.3, 64.0, 126.5, 130.6, 130.6, 133.5, 138.5; C: 79.3, 118.3, 133.6, 134.8, 139.9, 140.9, 148.1, 154.9, 170.0; $\delta_H$ ($CDCl_3$): 1.46 (s,9H,—$CMe_3$), 5.74 (s,1H,$H_{11}$), 7.12 (d,1H,Ar—H), 7.16 (s,1H,Ar—H), 7.19 (s,1H,Ar—H), 7.23 (d,1H,Ar—H), 8.29 (s,1H,Ar—H); $[\alpha]_D^{23.4°\ C.}$ +56.4° (9.05 mg/2 mL, MeOH).

Step B
(+) 1-(3-Bromo-8-chloro-6,11-dihydro-5H-benzo[5,6]cyclo-hepta [1,2-b]pyridin-11R-yl)-4-(4-piperidinylacetyl)piperazine N1-oxide

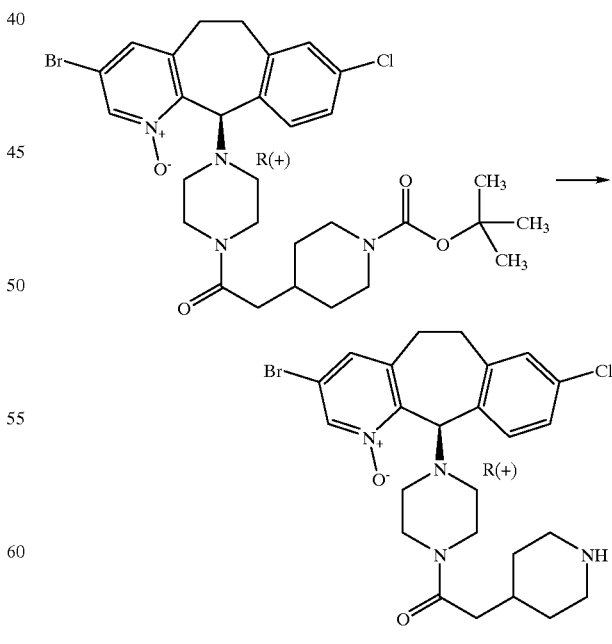

The title compound from Step A above (1.149 g, 1.812 mmoles) was dissolved in methanol (9.5 mL) and 10% (v/v) conc. $H2SO_4$ in dioxane (24.7 mL) and the mixture was stirred under argon at 25° C. for 1 h. The mixture was passed over a bed of BioRad AG1-X8(OH⁻form) ion exchange resin and the resin was washed with methanol. The combined eluates were evaporated to dryness and the product was chromatographed on silica gel using 10% (10% conc NH₄OH in MeOH)dichloromethane as the eluant to give the title compound (Yield: 762.9 mg, 79%):

LSIMS: m/z 533 (MH⁺), δ$_c$ (CDCl₃): CH₂: 30.2, 30.5, 33.2, 33.2, 40.1, 41.7, 45.9, 46.4, 46.4, 50.8, 51.2; CH: 33.4, 64.0, 126.5, 130.6, 130.6, 133.6, 138.6; C: 118.4, 133.6, 134.8, 139.9, 140.9, 148.2, 170.2; δ$_H$ (CDCl₃): 5.73 (s,1H, H$_{11}$), 7.11 (d,1H,Ar—H), 7.14 (s,1H,Ar—H), 7.19 (s,1H, Ar—H), 7.22 (d,1H,Ar—H), 8.28 (s,1H,Ar—H; [α]$_D^{23.2° C.}$ +66.4° (10.90 mg/2 mL, MeOH).

Step C (+) 4-[2-[(3-Bromo-8-chloro-6,11-dihydro-5H-benzo[5,6] cyclohepta [1,2-b]pyridin-11R-yl)-1-piperazinyl]-2-oxoethyl]-1-piperidinecarboxamide N1-oxide

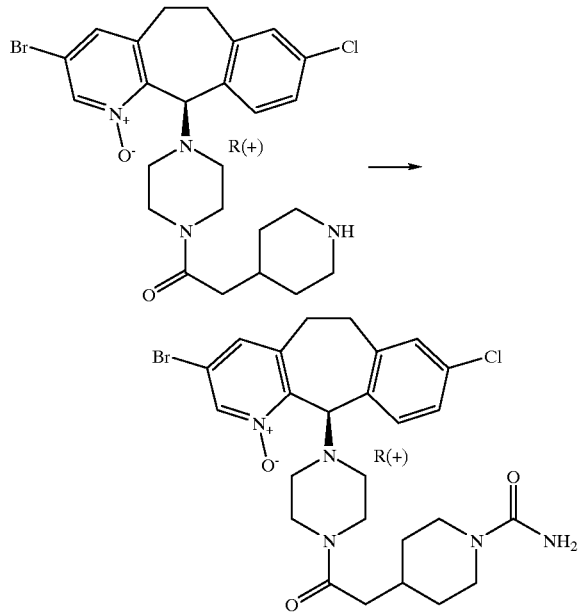

The title compound from Step B above (550 mg, 1.03 mmoles) and trimethylsilyl isocyanate (2.092 mL, 15.45 mmoles) were dissolved in anhydrous dichloromethane (16.4 mL) and the mixture was stirred at 25° C. under argon for 18 h. The mixture was diluted with dichloromethane and washed with saturated aqueous NaHCO₃, dried (MgSO₄), filtered and evaporated to dryness. The product was chromatographed on silica gel using 3.5% (10% conc. NH₄OH in methanol)dichloromethane as the eluant to give the title compound (Yield: 570.3 mg, 99%): FABMS: m/z 576.3 (MH⁺); δ$_c$ (CDCl₃): CH₂: 30.2, 30.5, 32.1, 32.1, 39.3, 41.7, 44.4, 44.5, 45.8, 50.8, 51.2; CH: 33.0, 64.0, 126.5, 130.6, 130.6, 133.5, 138.6; C: 118.4, 133.5, 134.8, 139.9, 141.0, 148.1, 157.9, 169.8; δ$_H$ (CDCl₃): 5.73 (s,1H,H$_{11}$), 7.12 (d,1H,Ar—H), 7.14 (s,1H,Ar—H), 7.19 (s,1H,Ar—H), 7.21 (d,1H,Ar—H), 20 8.28 (s,1H,Ar—H); [α]$_D^{23.4° C.}$ +60.2° (10.28 mg/2 mL, MeOH).

EXAMPLE 11

(−) 4-[2-[(3-Bromo-8-chloro-6,11-dihydro-5H-benzo[5,6] cyclo-hepta [1,2-b]pyridin-11S-yl)-1-piperazinyl]-2-oxoethyl]-1-piperidinecarboxamide N1-oxide

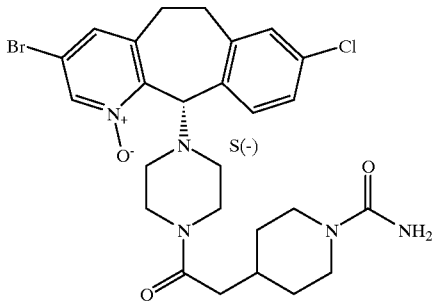

Step A (−) 1,1-Dimethylethyl 4-[[[4-(3-bromo-8-chloro-6,11-dihydro -5H-benzo[5,6]cyclohepta[1,2-b]pyridin-11S-yl)-1-piperazinyl]-1-carbonyl]methyl]-1-piperidinecarboxylate N1-oxide

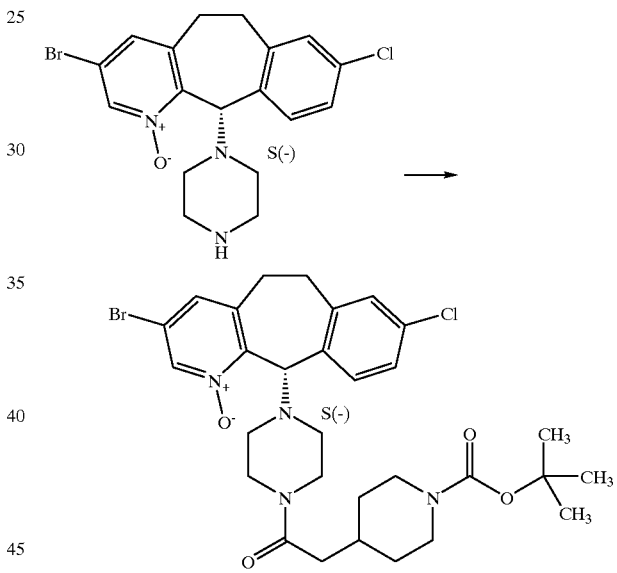

The title compound from Preparative Example 33, Step E, S(−) enantiomer (1 g, 2.45 mmoles), 1-tert-butoxycarbonyl-4-piperidinylacetic acid (487 mg, 3.181 mmoles), 1-(3-dimethyl-aminopropyl) -3-ethylcarbodiimide hydrochloride (610 mg, 3.181 mmoles), 1-hydroxybenzotriazole (430 mg, 3.181 mmoles) and 4-methylmorpholine (0.35 mL, 3.181 mmoles) were dissolved in anhydrous DMF (30.5 mL) and the mixture was stirred at 25° C. for 66 h. The reaction was worked up as described in Example 1 and the product was chromatographed on silica gel using 1% (10% conc. NH₄OH in methanol)dichloromethane as the eluant to give the title compound (Yield: 1.204 g, 78%): LSIMS: m/z 633.5 (MH⁺); δ$_c$ (CDCl₃) CH₃: 28.5, 28.5, 28.5; CH₂: 30.2, 30.5, 32.2, 32.2, 39.4, 41.7, 43.6, 43.6, 45.8, 50.7, 51.2; CH: 33.3, 64.0, 126.5, 130.5, 130.5, 133.6, 138.5; C: 79.3, 118.3, 133.6, 134.8, 139.9, 140.9, 148.1, 154.8, 170.0; δ$_H$ (CDCl₃): 1.46 (s,9H,—CMe₃), 5.74 (s,1H,H$_{11}$), 7.12 (d,1H,Ar—H), 7.15 (s,1H,Ar—H), 7.19 (s,1H,Ar—H), 7.22 (d,1H,Ar—H), 8.28 (s,1H,Ar—H); [α]$_D^{23.7° C.}$ −57.2° (9.09 mg/2 mL, MeOH).

Step B (−) 1-(3-Bromo-8-chloro-6,11-dihydro-5H-benzo[5,6]cyclo-hepta [1,2-b]pyridin-11S-yl)-4-(4-piperidinylacetyl) piperazine N1-oxide

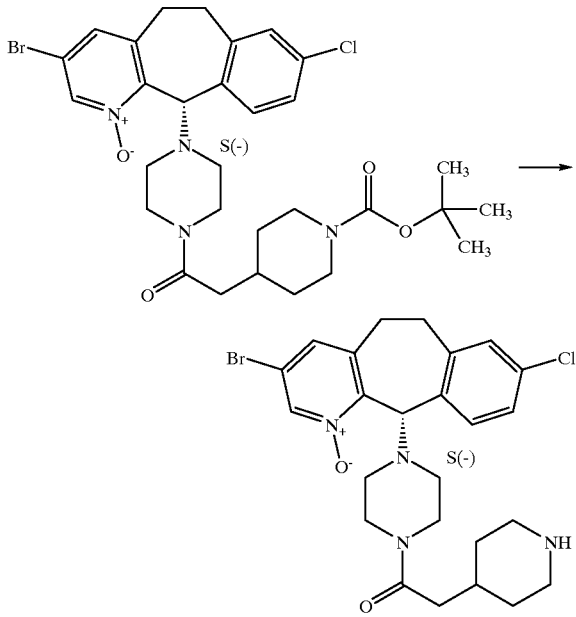

The title compound from Step A above (1.104 g, 1.741 mmoles) was dissolved in methanol (9.13 mL) and 10% (v/v) conc. $H_2SO_4$ in dioxane (23.75 mL) and the mixture was stirred under argon at 25° C. for 1 h. The mixture was passed over a bed of BioRad AG1-X8(OH⁻form) ion exchange resin and the resin was washed with methanol. The combined eluates were evaporated to dryness and the product was chromatographed on silica gel using 10% (10% conc $NH_4OH$ in MeOH)dichloromethane as the eluant to give the title compound (Yield: 771.6 mg, 83%): LSIMS: m/z 533 (MH⁺), $\delta_c$ (CDCl₃): CH₂: 30.3, 30.5, 33.0, 33.0, 40.0, 41.7, 45.8, 46.2, 46.2, 50.8, 51.2; CH: 33.3, 64.0, 126.5, 130.6, 130.6, 133.6, 138.6; C: 118.4, 133.6, 134.8, 139.9, 140.9, 148.2, 170.1; $\delta_H$ (CDCl₃): 5.73 (s,1H,H₁₁), 7.12 (d,1H,Ar—H), 7.14 (s,1H,Ar—H), 7.19 (s,1H,Ar—H), 7.22 (d,1H,Ar—H), 8.28 (s,1H,Ar—H); $[\alpha]_D^{23.1°\ C.}$ −66.9° (10.29 mg/2 mL, MeOH).

Step C (−) 4-[2-[(3-Bromo-8-chloro-6,11-dihydro-5H-benzo[5,6]cyclohepta [1,2-b]pyridin-11S-yl-1-piperazinyl]-2-oxoethyl]-1-piperidinecarboxamide N1-oxide

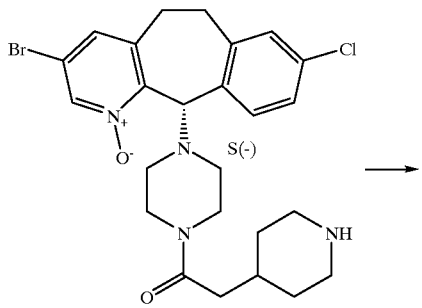

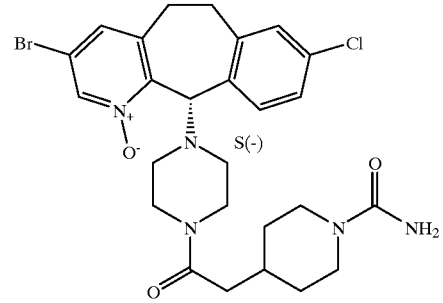

The title compound from Step B above (550 mg, 1.03 mmoles) and trimethylsilyl isocyanate (2.092 mL, 15.45 mmoles) were dissolved in anhydrous dichloromethane (16.4 mL) and the mixture was stirred at 25° C. under argon for 18 h. The mixture was diluted with dichloromethane and washed with saturated aqueous NaHCO₃, dried (MgSO₄), filtered and evaporated to dryness. The product was chromatographed on silica gel using 3.5% (10% conc. $NH_4OH$ in methanol)dichloromethane as the eluant to give the title compound (Yield: 571.5 mg, 99%): FABMS: m/z 576.3 (MH⁺); $\delta_c$ (CDCl₃): CH₂: 30.2, 30.5, 32.0, 32.0, 39.3, 41.7, 44.4, 44.5, 45.7, 50.7, 51.2; CH: 33.0, 64.0, 126.5, 130.6, 130.6, 133.5, 138.5; C: 118.4, 133.6, 134.8, 139.9, 141.0, 148.1, 157.9, 169.8; $\delta_H$ (CDCl₃): 5.73 (s,1H,H₁₁), 7.12 (d,1H,Ar—H), 7.15 (s,1H,Ar—H), 7.20 (s,1H,Ar—H), 7.22 (d,1H,Ar—H), 20 8.28 (s,1H,Ar—H); $[\alpha]_D^{23.1°\ C.}$ 62.5° (9.54 mg/2 mL, MeOH).

EXAMPLE 12

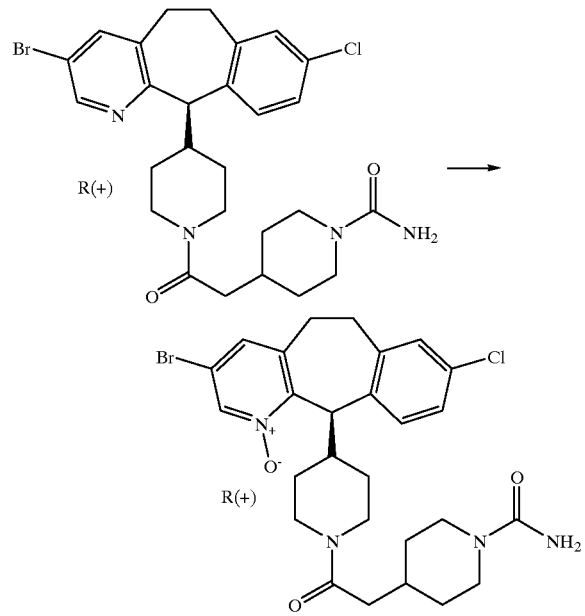

The starting reactant (0.g, 0.18 mmol), was disssolved in $CH_2Cl_2$ (5 mL) and then cooled to −18° C. m-Chloroperoxybenzoic acid (0.18 g, 1.07 mmol) was then added and the reaction mixture was stirred at room temperature overnight. The reaction mixture was partitioned between $CH_2Cl_2$ and saturated NaHCO₃ (aqueous). The aqueous phase was extracted further with $CH_2Cl_2$. Combined $CH_2Cl_2$ fractions were dried over MgSO₄ and concentrated in vacuo to give a residue that was chromatographed on a silica plate eluting with 10% MeOH (saturated NH$_3$)—CH$_2$Cl$_2$ eluent to give the title compound as a white solid (0.013 g, 13% yield, mp=146.8–147.4° C., MH$^+$=577).

The starting reactant is obtained by the procedure of Preparative Example 14, and the chiral chromatography separation procerdures described above.

EXAMPLE 13

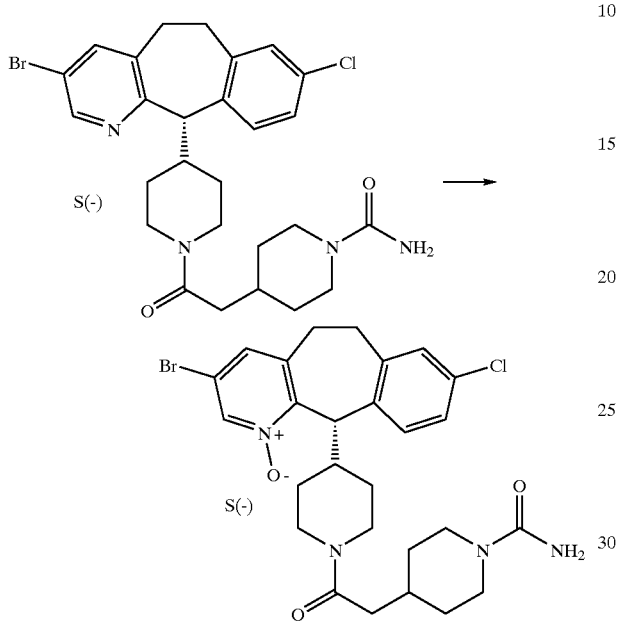

The title compound was prepared by essentially the same procedure as described in Example 12 (mp=120–121° C., MH$^+$=577).

EXAMPLE 14

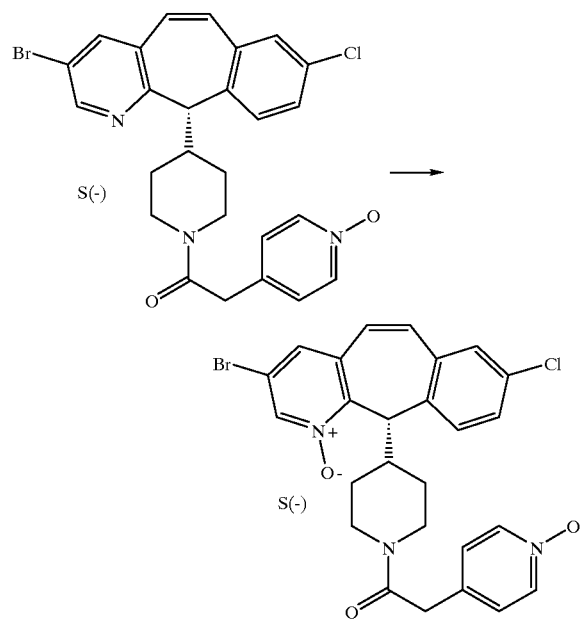

Following essentially the same oxidation procedure as in Example 12, the starting reactant is oxidized with m-chloroperoxybenzoic acid to yield the title compound (mp=109–110° C., MH$^+$=542).

The starting reactant is obtained by reacting the S(–) isomer of the title compound of Preparative Example 3 with title compound of Preparative Example 1 by essentially the same procedure as described in Preparative Example 12. The S(–) isomer of the racemate of Preparative Example 3 is obtained by the chiral chromatography separation procerdures described above.

EXAMPLE 15

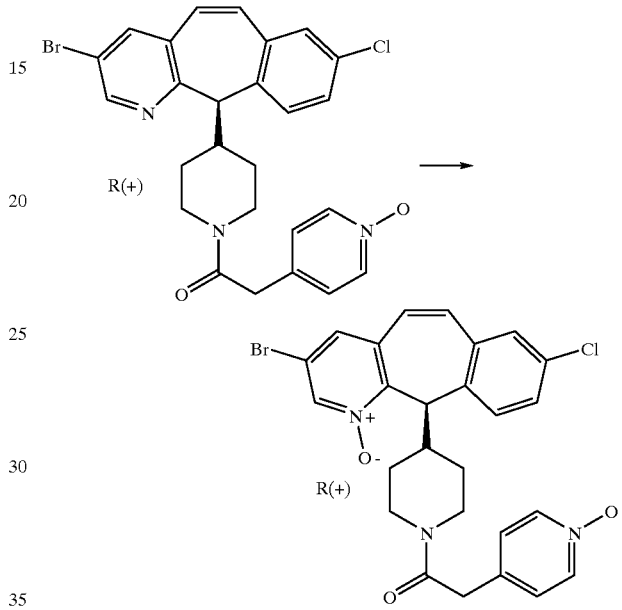

The title compound was prepared by essentially the same procedure as described in Example 14 (mp=125.5–126.3° C., MH$^+$=542).

ASSAYS

FPT IC$_{50}$ (inhibition of farnesyl protein transferase, in vitro enzyme assay) was determined following the assay procedures described in WO 95/10516, published Apr. 20, 1995. GGPT IC$_{50}$ (inhibition of geranylgeranyl protein transferase, in vitro enzyme assay), COS Cell IC$_{50}$ (Cell-Based Assay), Cell Mat Assay, and anti-tumor activity (in vivo anti-tumor studies) could be determined by the assay procedures described in WO 95/10516. The disclosure of WO 95/10516 is incorporated herein by reference thereto.

Additional assays can be carried out by following essentially the same procedure as described above, but with substitution of alternative indicator tumor cell lines in place of the T24-BAG cells. The assays can be conducted using either DLD-1-BAG human colon carcinoma cells expressing an activated K-ras gene or SW620-BAG human colon carcinoma cells expressing an activated K-ras gene. Using other tumor cell lines known in the art, the activity of the compounds of this invention against other types of cancer cells could be demonstrated.

Soft Agar Assay

Anchorage-independent growth is a characteristic of tumorigenic cell lines. Human tumor cells can be suspended in growth medium containing 0.3% agarose and an indicated concentration of a farnesyl transferase inhibitor. The solution can be overlayed onto growth medium solidified with 0.6% agarose containing the same concentration of farnesyl transferase inhibitor as the top layer. After the top layer is solidified, plates can be incubated for 10–16 days at 37° C. under 5% $CO_2$ to allow colony outgrowth. After incubation, the colonies can be stained by overlaying the agar with a solution of MTT (3-[4,5-dimethyl-thiazol-2-yl]-2,5-diphenyltetrazolium bromide, Thiazolyl blue) (1 mg/mL in PBS). Colonies can be counted and the $IC_{50}$'s can be determined.

FPT pM $IC_{50}$ Assay

The enzymatic reaction is performed in 50 mM Tris, 5 $\mu$M $ZnCl_2$, 5 mM $MgCl_2$, 0.01% Triton X-100, 5 mM dithiolthreitol (DTT), pH 7.7 (Buffer R) at 37° C. for 1 hour. The purified human FPT (>95% pure) was derived from a Baculovirus/Sf-9 expression system. The peptide substrate used was biotin-CVLS (SynPep Corp., Dublin, Calif.) and $(1-{}^3H)$-FPP (21.5 Ci/mmol) was obtained from New England Nuclear Life Science Products (Boston, Mass.). Compounds were initially dissolved to a final concentration of 4 mg/ml in 100% DMSO and then to 0.25 $\mu$g/ml in 100% DMSO. Subsequent dilutions of the compound were performed in Buffer R.

The enzymatic reaction is performed in a final volume of 100 $\mu$l. Reactions are carried out in a 96 well plate format. The final concentrations of human FPT, FPP and biotin-CVLS are 30 pM, 176 nM and 100 nM, respectively, in a volume of 100 $\mu$l. A typical reaction involves the prequilibration of FPT and FPP in 40 $\mu$l at room temperature for 15 minutes followed by the addition of 40 $\mu$l of a solution containing test compound. This is further equilibrated for 15 minutes at room temperature. The enzymatic reaction is initiated by adding 20 $\mu$l of the biotin-CVLS peptide substrate and allowed to proceed at 37° C. for 1 hour. The reaction is stopped using 150 $\mu$l of the Stop Solution consisting of 1.3 mg/ml scintillation beads (strepavidin-coated scintillation proximity beads from Amersham (Arlington Heights, Ill.), 250 mM EDTA, pH 8.0 and 0.5% BSA. The radioactivity is measured after 20 minutes at room temperature.

Compounds are evaluated for their ability to inhibit the reaction by measuring the concentration-dependent percent inhibition of the reaction. Compound stocks at 0.25 $\mu$g/ml (DMSO) were diluted into Buffer R and then into the reaction mixture as described above to give a final concentration of 0.01, 0.003, 0.001, 0.0003, 0.0001 and 0.00003 $\mu$g/ml in the reaction mixture. The enzymatic activity was recorded by measuring the CPM/well using a Wallac 1204 Betaplate BS liquid scintillation counter. Control experiments were performed without inhibitors to provide a CPM value for the non-inhibited reaction. In addition, reactions were performed without biotin-CVLS to provide a signal for background CPM values. After correcting the signals for background the percent inhibition would be calculated for each inhibitor concentration and an $IC_{50}$ value would be interpolated from a least squares analysis of the data within the linear region of inhibition.

| Compound of Example No. | FPT $IC_{50}$ |
| --- | --- |
| 1 | 13 |
| 2 | 1.4 |
| 3 | 0.7 |
| 4 | 18 |
| 5 | 28 |
| 6 | 63 |
| 7 | 6.3 |

-continued

| Compound of Example No. | FPT $IC_{50}$ |
| --- | --- |
| 8 | 39% @ 170 |
| 9 | 23 |
| 10 | 12 |
| 11 | 24% @ 160 |
| 12 | 35 |
| 13 | 174 |
| 14 | 25% @ 180 |
| 15 | 19 |

Compound 54.0 had an FPT $IC_{50}$ of 42%@150 nM.

The compound of Example 7 had an FPT pM $IC_{50}$ of 0.44 nM and the compound of Example 10 had an FPT pM $IC_{50}$ of 0.41 nM.

The compound of Example No. 2 had a COS Cell $IC_{50}$ of 9nM and a Soft Agar $IC_{50}$ of 45 nM. The compound of Example No. 3 had a COS Cell $IC_{50}$ of 11.5 nM and a Soft Agar l$C_{50}$ of 25 nM. The compound of Example No. 7 had a COS Cell $IC_{50}$ of 85 nM and a Soft Agar l$C_{50}$ of 183 nM.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range. The following are examples of pharmaceutical dosage forms which contain a compound of the invention. The scope of the invention in its pharmaceutical composition aspect is not to be limited by the examples provided.

Pharmaceutical Dosage Form Examples

EXAMPLE A

Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B

Capsules

| No. | Ingredients | mg/capsule | mg/capsule |
|---|---|---|---|
| 1. | Active compound | 100 | 500 |
| 2. | Lactose USP | 106 | 123 |
| 3. | Corn Starch, Food Grade, | 40 | 70 |
| 4. | Magnesium Stearate NF | 7 | 7 |
| | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound selected from the group consisting of:

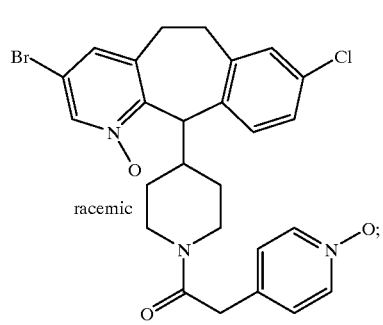

(4.0)

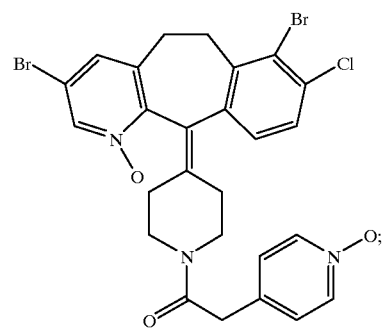

(8.0)

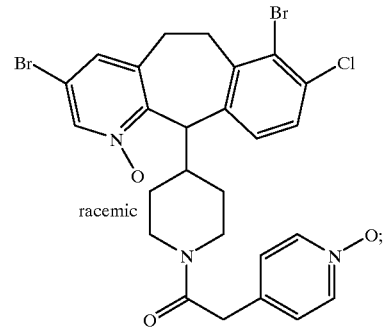

(13.0)

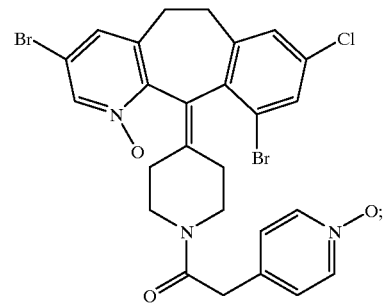

(14.0)

101
-continued
(20.0)
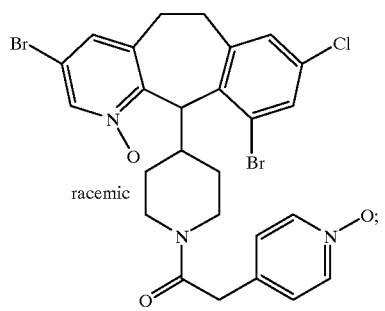
racemic
(33.0)
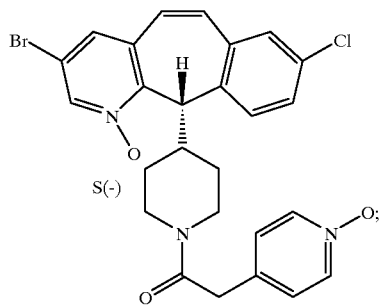
S(-)
(34.0)
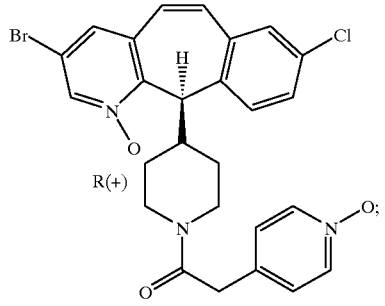
R(+)
(39.0)
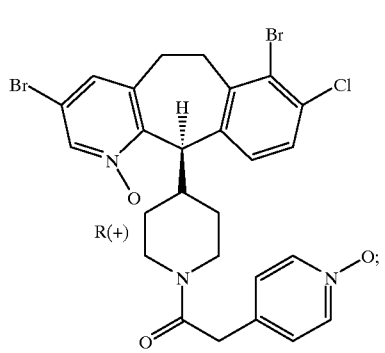
R(+)
(40.0)
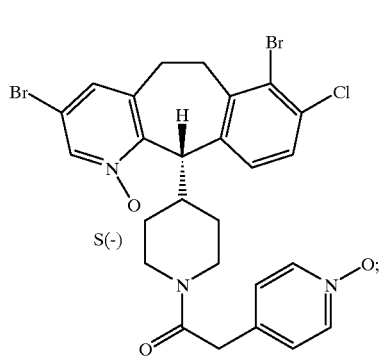
S(-)
102
-continued
(43.0)
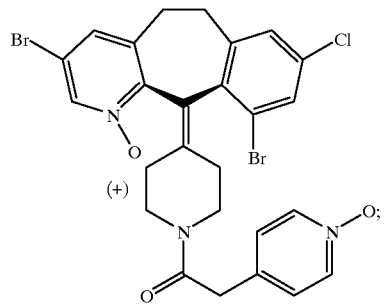
(+)
(44.0)
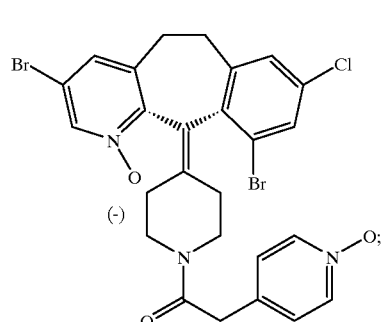
(-)
(51.0)
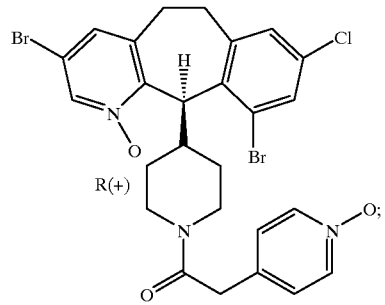
R(+)
(52.0)
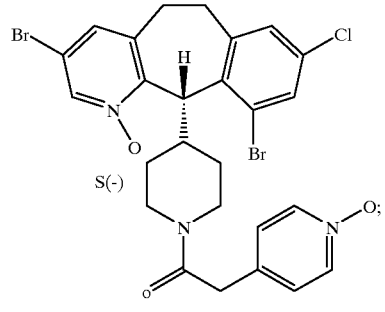
S(-)
(56.0)
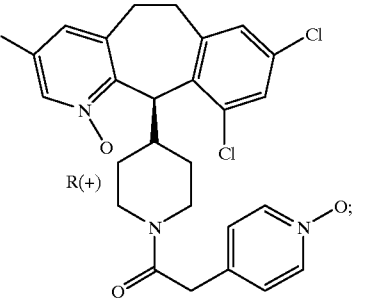
R(+)

-continued
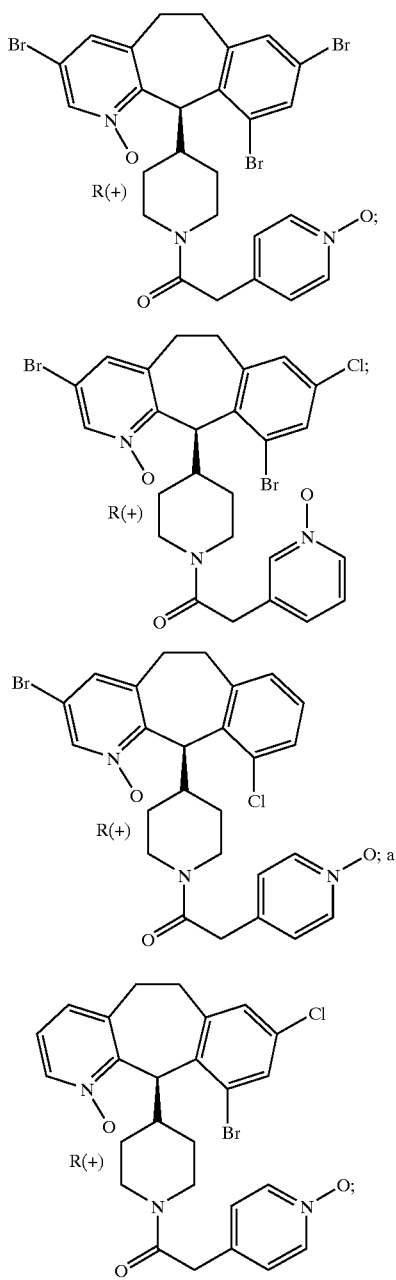
(58.0)
(59.0)
(60.0)
(63.0)
or pharmaceutically acceptable salts or solvates thereof.
2. The compound of claim 1 selected from:
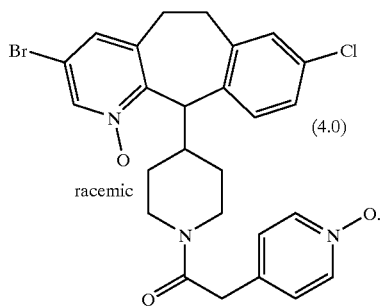
(4.0)
3. The compound of claim 1 selected from the group consisting of:
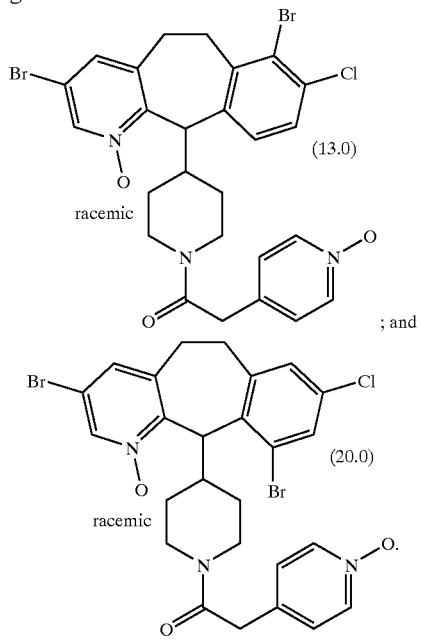
(13.0)
; and
(20.0)
4. The compound of claim 1 selected from the group consisting of:
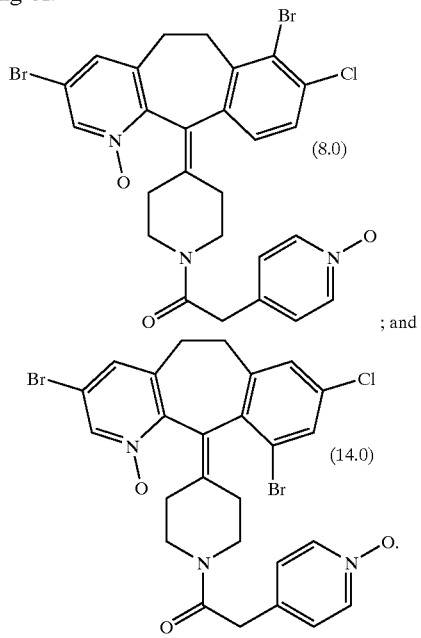
(8.0)
; and
(14.0)
5. The compound of claim 1 selected from the group consisting of:
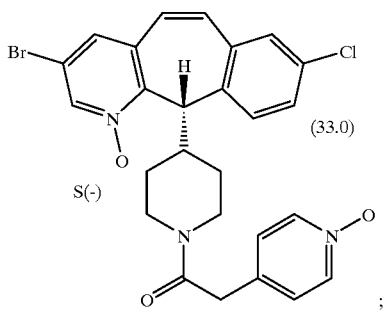
(33.0)
;

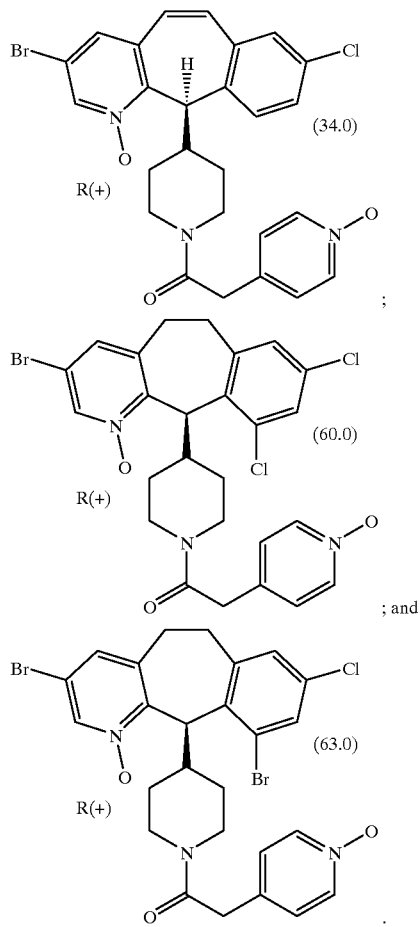
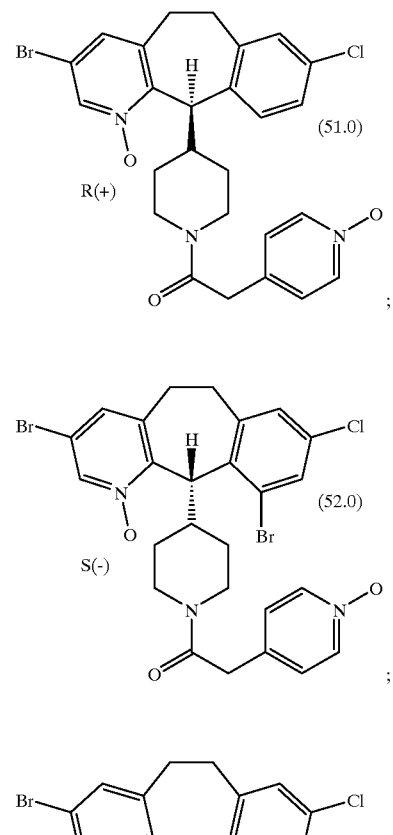
6. The compound of claim 1 selected from the group consisting of:
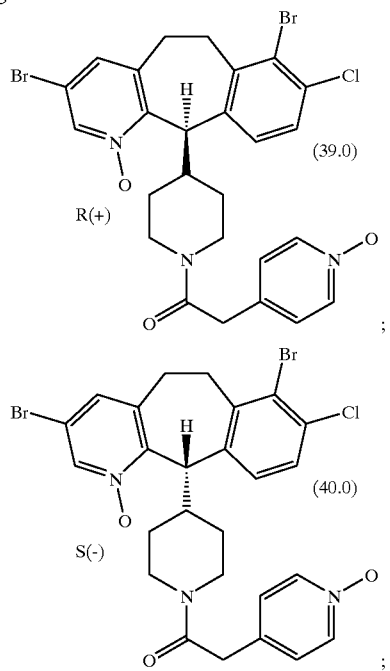
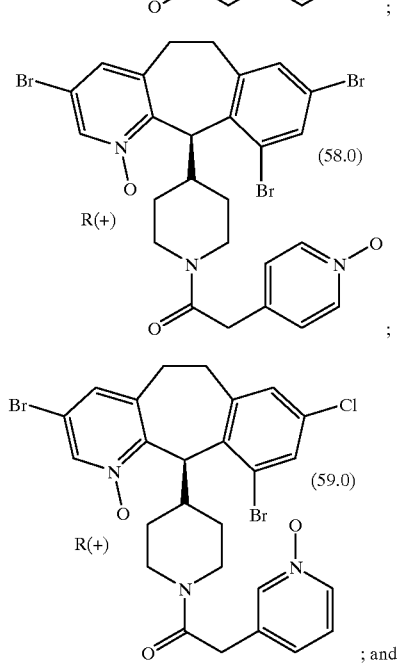

-continued

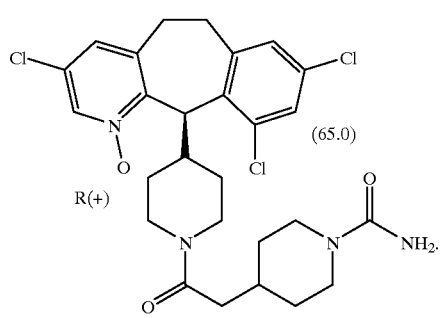
(65.0) R(+)

7. The compound of claim 1 selected from the group consisting of:

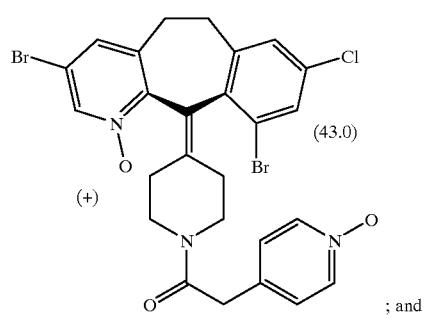
(43.0) (+)

; and

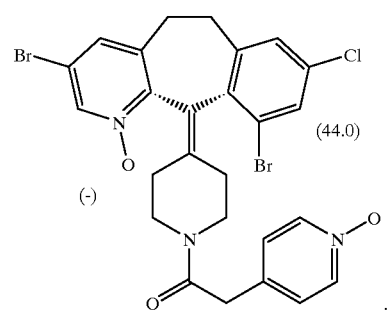
(44.0) (−)

8. The compound of claim 1 selected from the group consisting of:

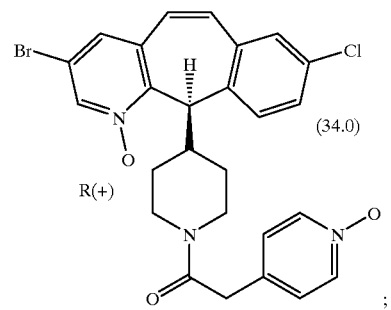
(34.0) R(+)

;

-continued

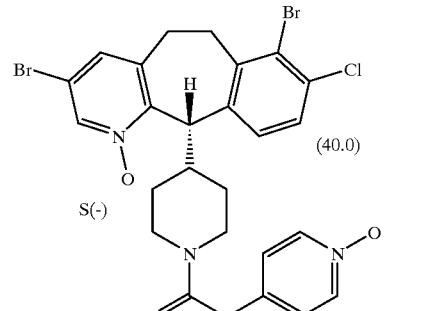
(40.0) S(−)

; and

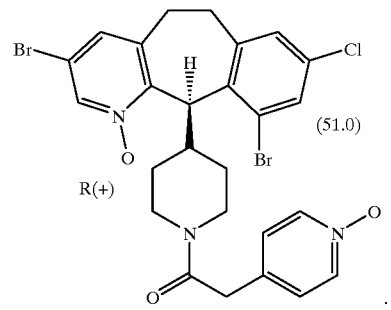
(51.0) R(+)

9. The compound of claim 1 selected from:

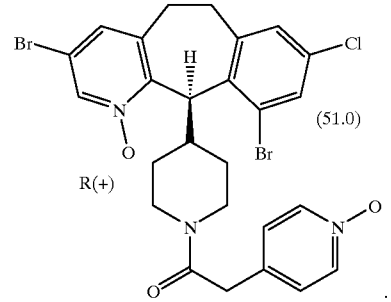
(51.0) R(+)

10. A method for inhibiting the abnormal growth of cells comprising administering an effective amount of a compound of claim 1.

11. The method of claim 10 wherein the cells inhibited are tumor cells expressing an activated ras oncogene.

12. The method of claim 10 wherein the inhibition of the abnormal growth of cells occurs by the inhibition of farnesyl protein transferase.

13. The method of claim 10 wherein the inhibition is of tumor cells wherein the Ras protein is activated as a result of oncogenic mutation in genes other than the Ras gene.

14. A method of inhibiting farnesyl protein transferase in a patient in need of such treatment comprising administering an effective amount of a compound of claim 1.

15. A method of inhibiting farnesyl protein transferase in a patient in need of such treatment comprising administering an effective amount of a compound of claim 9.

16. A method of treating pancreatic cancer, lung cancer, myeloid leukemia, thyroid follicular cancer, myelodysplastic syndrome, epidermal carcinoma, bladder carcinoma, colon cancer, breast cancer or prostate cancer in a patient in need of such treatment comprising administering an effective amount of a compound of claim 1.

17. A method of treating pancreatic cancer, lung cancer, myeloid leukemia, thyroid follicular cancer, myelodysplastic syndrome, epidermal carcinoma, bladder carcinoma, colon cancer, breast cancer or prostate cancer in a patient in need of such treatment comprising administering an effective amount of a compound of claim 9.

18. A pharmaceutical composition comprising an effective amount of a compound of claim 1 in combination with a pharmaceutically acceptable carrier.

19. A pharmaceutical composition comprising an effective amount of a compound of claim 9 in combination with a pharmaceutically acceptable carrier.

* * * * *